US012138299B2

(12) United States Patent
Alenghat

(10) Patent No.: US 12,138,299 B2
(45) Date of Patent: Nov. 12, 2024

(54) ALDEHYDE DEHYDROGENASE PRODUCING BACTERIA AND METHODS OF USING SAME

(71) Applicant: Children's Hospital Medical Center, Cincinnati, OH (US)

(72) Inventor: Theresa Alenghat, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 18/625,448

(22) Filed: Apr. 3, 2024

(65) Prior Publication Data

US 2024/0285733 A1    Aug. 29, 2024

Related U.S. Application Data

(63) Continuation of application No. PCT/US2022/045511, filed on Oct. 3, 2022.

(60) Provisional application No. 63/251,919, filed on Oct. 4, 2021.

(51) Int. Cl.
*A61K 38/44* (2006.01)
*A61P 31/04* (2006.01)
*A61P 37/04* (2006.01)
*C12N 9/02* (2006.01)

(52) U.S. Cl.
CPC .............. *A61K 38/44* (2013.01); *A61P 31/04* (2018.01); *A61P 37/04* (2018.01); *C12N 9/0008* (2013.01); *C12Y 102/01003* (2013.01)

(58) Field of Classification Search
None
See application file for complete search history.

(56) References Cited

FOREIGN PATENT DOCUMENTS

WO    WO 2017/123676 A1    7/2017

OTHER PUBLICATIONS

Abt, M.C., et al. (2014). "Commensal bacteria mediated defenses against pathogens," Curr. Opin. Immunol., 29, 16-22, 7 pgs.
Alenghat, T., et al. (2013). "Histone Deacetylase 3 coordinates commensal bacteria-dependent intestinal homeostasis," Nature 504(7478), 153-157, 17 pgs.
Amatullah, H., et al. (2020). "Epigenome-metabolome-microbiome axis in health and IBD," Curr. Opin. Microbiol. 56, 97-108, 20 pgs.
Ansari, I., et al. (2020). "The microbiota programs DNA methylation to control intestinal homeostasis and inflammation," Nat. Microbiol. 5,610-619, 19 pgs.
Arnold, S.L.M., et al. (2015). "Pharmacological inhibition of ALDH1A in mice decreases all-trans retinoic acid concentrations in a tissue specific manner," Biochem. Pharmacol. 95(3), 177-192, 35 pgs.
Arrowsmith, C.H., et al. (2012). "Epigenetic protein families: A new frontier for drug discovery," Nat Rev Drug Discov, 11:384-400, 17 pgs.
Atarashi, K., et al. (2015). "Th17 Cell Induction by Adhesion of Microbes to Intestinal Epithelial Cells," Cell, 163:367-380, 15 pgs.
Benson, A., et al. (2009). "Gut Commensal Bacteria Direct a Protective Immune Response against *Toxoplasma gondii*," Cell Host Microbe, 6:187-196, 10 pgs.
Benson, M.J., et al. (2007). "All-trans retinoic acid mediates enhanced T reg cell growth, differentiation, and gut homing in the face of high levels of co-stimulation," J Exp Med, 204(8):1765-1774, 10 pgs.
Bhinder, G., et al. (2014). "Intestinal epithelium-specific MyD88 signaling impacts host susceptibility to infectious colitis by promoting protective goblet cell and antimicrobial responses," Infect Immun, 82(9):1-17, 17 pgs.
Biesalski, H.K., et al. (2007). "Conversion of β-Carotene to Retinal Pigment," Vitam. Horm. 75, 117-130, 14 pgs.
Cabrera, G., et al. (2014). "Retinoid levels influence enterohemorrhagic *Escherichia coli* infection and shiga toxin 2 susceptibility in mice," Infect Immun, 82(9):3948-3957, 18 pgs.
Cha, H.-R., et al. (2010). "Downregulation of Th17 Cells in the Small Intestine by Disruption of Gut Flora in the Absence of Retinoic Acid," J Immunol, 184:6799-6806, 8 pgs.
Chang, P.V., et al. (2014). "The microbial metabolite butyrate regulates intestinal macrophage function via histone deacetylase inhibition," PNAS, 111(6):2247-2252, 6 pgs.
Christian, P., et al. (1998). "Interactions between zinc and vitamin A: an update," Am J Clin Nutr, 68(suppl):435S-441S, 7 pgs.
Chung, H., et al. (2012). "Gut Immune Maturation Depends on Colonization with a Host-Specific Microbiota," Cell, 149:1578-1593, 16 pgs.
Creyghton, M.P., et al. (2010). "Histone H3K27ac separates active from poised enhancers and predicts developmental state," PNAS, 107(50):21931-21936, 6 pgs.
Dalile, B., et al. (2019). "The role of short-chain fatty acids in microbiota-gut-brain communication," Nat. Rev. Gastroenterol. Hepatol. 16, 461-478, 18 pgs.
Dibley, M.J., et al. (1996). "Vitamin A Supplementation Fails to Reduce Incidence of Acute Respiratory Illness and Diarrhea in Preschool-Age Indonesian Children," J Nutr, 126:434-442, 9 pgs.
Erkelens, M.N., et al. (2017). "Retinoic Acid and Immune Homeostasis: A Balancing Act," Trends Immunol. 38(3), 168-180, 13 pgs.
Fellows, R., et al. (2018). "Microbiota derived short chain fatty acids promote histone crotonylation in the colon through histone deacetylases," Nat Commun, 9:105, 15 pgs.
Furusawa, Y., et al. (2013). "Commensal microbe-derived butyrate induces the differentiation of colonic regulatory T cells," Nature 504, 446-450, 8 pgs.

(Continued)

*Primary Examiner* — Suzanne M Noakes
*Assistant Examiner* — Jae W Lee
(74) *Attorney, Agent, or Firm* — Frost Brown Todd LLP

(57) ABSTRACT

Disclosed herein are methods for enhancing an immune response in an individual in need thereof. The methods, in certain aspects, may comprise administering bacterial aldehyde dehydrogenase, a bacteria that produces aldehyde dehydrogenase, or combinations thereof to an individual. Further disclosed are compositions, such as nutritional compositions, which may comprise bacterial aldehyde dehydrogenase, a bacteria that produces aldehyde dehydrogenase, or combinations thereof.

18 Claims, 25 Drawing Sheets

Specification includes a Sequence Listing.

(56) References Cited

OTHER PUBLICATIONS

Gallo, R.L., et al. (2012). "Epithelial antimicrobial defence of the skin and intestine," Nat. Rev. Immunol. 12(7), 503-516, 27 pgs.
Ganal, S.C., et al. (2012). "Priming of Natural Killer Cells by Nonmucosal Mononuclear Phagocytes Requires Instructive Signals from Commensal Microbiota," Immunity, 37:171-186, 16 pgs.
Garland, C.D., et al. (1982). "Segmented Filamentous Bacteria in the Rodent Small Intestine: Their Colonization of Growing Animals and Possible Role in Host Resistance to *Salmonella*," Microb. Ecol. 8, 181-190, 10 pgs.
Gattu, S., et al. (2019). "Epithelial retinoic acid receptor β regulates serum amyloid A expression and vitamin A-dependent intestinal immunity," PNAS, 116(22):10911-10916, 6 pgs.
Goto, Y., et al. (2014). "Segmented Filamentous Bacteria Antigens Presented by Intestinal Dendritic Cells Drive Mucosal Th17 Cell Differentiation," Immunity 40:594-607, 16 pgs.
Green, H.N., et al. (1928). "Vitamin A as an Anti-Infective Agent," Br Med J, 2:691-696, 6 pgs.
Grizotte-Lake, M., et al. (2018). "Commensals Suppress Intestinal Epithelial Cell Retinoic Acid Synthesis to Regulate Interleukin-22 Activity and Prevent Microbial Dysbiosis," Immunity, 49:1103-1115.e6, 19 pgs.
Gundra, U.M., et al. (2017). "Vitamin A mediates conversion of monocyte-derived macrophages into tissue-resident macrophages during alternative activation," Nat. Immunol. 18(6), 642-653, 32 pgs.
Hall, J.A., et al. (2011a). "The Role of Retinoic Acid in Tolerance and Immunity," Immunity, 35:13-22, 10 pgs.
Hall, J.A., et al. (2011b). "Essential Role for Retinoic Acid in the Promotion of CD4$^+$ T Cell Effector Responses via Retinoic Acid Receptor Alpha," Immunity, 34:435-447, 13 pgs.
Hantke, K. (2005). "Bacterial zinc uptake and regulators," Curr. Opin. Microbiol. 8, 196-202, 7 pgs.
Heczko, U., et al. (2000). "Segmented Filamentous Bacteria Prevent Colonization of Enteropathogenic *Escherichia coli* O103 in Rabbits," J Infect Dis, 181:1027-1033, 7 pgs.
Hong, S.-H., et al. (2016). "Alternative Biotransformation of Retinal to Retinoic Acid or Retinol by an Aldehyde Dehydrogenase from *Bacillus cereus*," Appl Environ Microbiol, 82(13):3940-3946, 13 pgs.
Huang, D.W., et al. (2009). "Systematic and integrative analysis of large gene lists using DAVID bioinformatics resources," Nat. Protoc. 4(1), 44-57, 14 pgs.
Huang, Z., et al. (2018). "Role of Vitamin A in the Immune System," J Clin Med, 7:258, 16 pgs.
Ivanov, I.I., et al. (2009). "Induction of Intestinal Th17 Cells by Segmented Filamentous Bacteria," Cell, 139:485-498, 14 pgs.
Iyer, N., et al. (2020). "Epithelium intrinsic Vitamin A signaling coordinates pathogen clearance in the gut via IL-18," PLoS Pathog, 16(4):e1008360, 22 pgs.
Jang, H.-J., et al. (2015). "Selective Retinol Production by Modulating the Composition of Retinoids From Metabolically Engineered *E. coli*," Biotechnol. Bioeng. 112, 1604-1612, 9 pgs.
Jang, H.-J., et al. (2011). "Retinoid production using metabolically engineered *Escherichia coli* with a two-phase culture system," Microb Cell Fact, 10:59, 12 pgs.
Jijon, H.B., et al. (2018). "Intestinal epithelial cell-specific RARα depletion results in aberrant epithelial cell homeostasis and underdeveloped immune system," Mucosal Immunol, 11(3):703-715, 13 pgs.
Jonsson, H., et al. (2020). "Genome sequence of segmented filamentous bacteria present in the human intestine," Commun Biol, 3:485, 9 pgs.
Kaiko, G.E., et al. (2016). "The Colonic Crypt Protects Stem Cells from Microbiota-Derived Metabolites," Cell, 165:1708-1720, 15 pgs.
Kamada, N., et al. (2012). "Regulated Virulence Controls the Ability of a Pathogen to Compete with the Gut Microbiota," Science 336(6086), 1325-1329 , 12 pgs.

Kartashov, A.V., et al. (2015). "BioWardrobe: an integrated platform for analysis of epigenomics and transcriptomics data," Genome Biol, 16:158, 7 pgs.
Kelley, L.A., et al. (2015). "The Phyre2 web portal for protein modeling, prediction and analysis," Nat Protoc, 10(6):845-858, 14 pgs.
Kelly, D., et al. (2018). "Microbiota-sensitive epigenetic signature predicts inflammation in Crohn's disease," JCI Insight, 3(18):e122104, 14 pgs.
Kim, M.H., et al. (2015). "Retinoic Acid Differentially Regulates the Migration of Innate Lymphoid Cell Subsets to the Gut," Immunity, 43:107-119, 13 pgs.
Ladinsky, M.S., et al. (2019). "Endocytosis of commensal antigens by intestinal epithelial cells regulates mucosal T cell homeostasis," Science, 363:1058 & eaat4042, 11 pgs.
Laubach, V.E., et al. (1995). "Mice lacking inducible nitric oxide synthase are not resistant to lipopolysaccharide-induced death," PNAS, 92:10688-10692, 5 pgs.
Lavelle, A., et al. (2020). "Gut microbiota-derived metabolites as key actors in inflammatory bowel disease," Nat. Rev. Gastroenterol. Hepatol. 17, 223-237, 15 pgs.
Lewis, J.D., et al. (2015). "Inflammation, Antibiotics, and Diet as Environmental Stressors of the Gut Microbiome in Pediatric Crohn's Disease," Cell Host Microbe, 18:489-500, 14 pgs.
Long, K.Z., et al. (2007). "Vitamin A Supplementation has Divergent Effects on Norovirus Infections and Clinical Symptoms among Mexican Children," J Infect Dis. 196:978-985, 8 pgs.
Madison, B.B., et al. (2002). "cis Elements of the Villin Gene Control Expression in Restricted Domains of the Vertical (Crypt) and Horizontal (Duodenum, Cecum) Axes of the Intestine," J Biol Chem, 277(36):33275-33283, 9 pgs.
Matsumoto, M., et al. (2018). "Free D-amino acids produced by commensal bacteria in the colonic lumen," Sci Rep, 8:17915, 7 pgs.
McCarville, J.L., et al. (2020). "Microbiota Metabolites in Health and Disease," Annu Rev Immunol, 38:147-170, 24 pgs.
McDaniel, et al. (2015). "Vitamin A-Deficient Hosts Become Nonsymptomatic Reservoirs of *Escherichia coli*-Like Enteric Infections," Infect Immun, 83(7):2984-2991, 15 pgs.
McDevitt, C.A., et al. (2011). "A molecular mechanism for bacterial susceptibility to Zinc," PLoS Pathog, 7(11):e1002357, 9 pgs.
Metzler, M.A., et al. (2018). "RDH10-mediated retinol metabolism and RARa-mediated retinoic acid signaling are required for submandibular salivary gland initiation," Dev, 145:dev164822, 13 pgs.
Mielke, L.A., et al. (2013). "Retinoic acid expression associates with enhanced IL-22 production by γδ T cells and innate lymphoid cells and attenuation of intestinal inflammation," J Exp Med, 210(6):1117-1124, 8 pgs.
Mucida, D., et al. (Jun. 14, 2007). "Reciprocal $T_H17$ and Regulatory T cell Differentiation Mediated by Retinoic Acid," Science. 317, 256-260; Correction Jun. 18, 2007, Science DOI:10.1126/science.1145697; Supporting Online Material Jun. 14, 2007, DOI: 10.1126/science.1145697, 33 pgs.
Mundy, R., et al. (2005). "*Citrobacter rodentium* of mice and man," Cell Microbiol, 7(12):1697-1706, 10 pgs.
Navabi, N., et al. (2017). "Epithelial Histone Deacetylase 3 Instructs Intestinal Immunity by Coordinating Local Lymphocyte Activation," Cell Rep, 19:1165-1175, 12 pgs.
Omenetti, S., et al. (2019). "The Intestine Harbors Functionally Distinct Homeostatic Tissue-Resident and Inflammatory Th17 Cells," Immunity, 51:77-89, 20 pgs.
Osbelt, L., et al. (2020). "Variations in microbiota composition of laboratory mice influence *Citrobacter rodentium* infection via variable short-chain fatty acid production," PLoS Pathog, 16(3):e1008448, 27 pgs.
Paik, J., et al. (2014). "Inhibition of Retinoic Acid Biosynthesis by the Bisdichloroacetyldiamine WIN 18,446 Markedly Suppresses Spermatogenesis and Alters Retinoid Metabolism in Mice," J Biol Chem, 289(21):15104-15117, 14 pgs.
Peterson, L. W., et al. (2014). "Intestinal epithelial cells: regulators of barrier function and immune homeostasis," Nat. Rev. Immunol. 14, 141-153, 13 pgs.

(56) References Cited

OTHER PUBLICATIONS

Price, A.E., et al. (2018). "A Map of Toll-like Receptor Expression in the Intestinal Epithelium Reveals Distinct Spatial, Cell Type-Specific, and Temporal Patterns," Immunity, 49:560-575, 23 pgs.

Rada-Iglesias, A., et al. (2011). "A unique chromatin signature uncovers early developmental enhancers in humans," Nature 470(7333), 279-283, 17 pgs.

Rahman, M.M., et al. (2002). "Synergistic effect of zinc and vitamin A on the biochemical indexes of vitamin A nutrition in children," Am J Clin Nutr, 75:92-98, 7 pgs.

Rajaii, F., et al. (2008). "Expression of the dominant negative retinoid receptor, RAR403, alters telencephalic progenitor proliferation, survival, and cell fate specification," Dev Biol, 316:371-382, 12 pgs.

Ramanan, D., et al. (2016). "Intrinsic Defense Mechanisms of the Intestinal Epithelium," Cell Host Microbe, 19:434-441, 8 pgs.

Rooks, M.G., et al. (2016). "Gut microbiota, metabolites and host immunity," Nat. Rev. Immunol. 16(6), 341-352, 28 pgs.

Sano, T., et al. (2015). "An IL-23R/IL-22 Circuit Regulates Epithelial Serum Amyloid A to Promote Local Effector Th17 Responses," Cell, 163:381-393, 16 pgs.

Seamons, A., et al. (2020). "Protective Effects of ALDH1A Enzyme Inhibition on *Helicobacter*-Induced Colitis in Smad3−/− Mice are Associated with Altered α4β7 Integrin Expression on Activated T Cells," Nutrients, 12:2927, 13 pgs.

Semba, R.D. (1999). "Vitamin A and immunity to viral, bacterial and protozoan infections," Proc Nutr Soc, 58:719-727, 10 pgs.

Shi, Z., et al. (2019). "Segmented Filamentous Bacteria Prevent and Cure Rotavirus Infection," Cell, 179:644-658.e13, 29 pgs.

Smith, J.C. (1980). "The Vitamin A-Zinc Connection: A Review," Ann. N. Y. Acad. Sci. 355, 62-75, 14 pgs.

Snyder, L.M., et al. (2019). "Retinoic Acid Mediated Clearance of *Citrobacter rodentium* in Vitamin A Deficient Mice Requires CD11b+ and T Cells," Front Immunol, 9:3090, 13 pgs.

Sommer, A. (2008). "Vitamin A Deficiency and Clinical Disease: An Historical Overview," J Nutr, 138: 1835-1839, 5 pgs.

Spaans, S.K., et al. (2015). "NADPH-generating systems in bacteria and archaea," Front Microbiol, 6:742, 27 pgs.

Sporer, A.J., et al. (2017). "Redox-based regulation of bacterial development and behavior," Annu Rev Biochem 86:777-797, 21 pgs.

Symonds, E.L., et al. (2009). "Involvement of T helper type 17 and regulatory T cell activity in Citrobacter rodentium invasion and inflammatory damage," Clin Exp Immunol, 157:148-154, 7 pgs.

Takahashi, H., et al. (2012). "TGF-β and retinoic acid induce miR-10a, which targets Bcl-6 and constrains helper T cell plasticity," Nat. Immunol. 13(6), 587-595, 25 pgs.

Takahashi, K., et al. (2009). "Epigenetic Regulation of TLR4 Gene Expression in Intestinal Epithelial Cells for the Maintenance of Intestinal Homeostasis," J Immunol, 183:6522-6529, 8 pgs.

Uematsu, S., et al. (2008). "Regulation of humoral and cellular gut immunity by lamina propria dendritic cells expressing Toll-like receptor 5," Nat. Immunol. 9(7), 769-776, 8 pgs.

Vallance, B.A., et al. (2002). "Modulation of Inducible Nitric Oxide Synthase Expression by the Attaching and Effacing Bacterial Pathogen *Citrobacter rodentium* in Infected Mice," Infect Immun, 2002, 70(11):6424-6435, 12 pgs.

Wang, C., et al. (2010). "Retinoic Acid Determines the Precise Tissue Tropism of Inflammatory Th17 Cells in the Intestine," J Immunol, 184:5519-5526, 8 pgs.

Wikoff, W.R., et al. (2009). "Metabolomics analysis reveals large effects of gut microflora on mammalian blood metabolites," PNAS, 106(10):3698-3703, 6 pgs.

Woo, V., et al. (2017). "Host-microbiota interactions: Epigenomic regulation," Curr. Opin. Immunol. 44, 52-60, 16 pgs.

Woo, V., et al. (2019). "Microbiota Inhibit Epithelial Pathogen Adherence by Epigenetically Regulating C-Type Lectin Expression," Front Immunol, 10:928, 10 pgs.

Woo, V., et al., "Commensal segmented filamentous bacteria-derived retinoic acid primes host defense to intestinal infection," Cell Host & Mircobe, Elsevier, NL, 2021, 29(12):1744, XP086892280.

World Health Organization (2009). "Global prevalence of vitamin A deficiency in populations at risk 1995-2005: WHO Global Database on Vitamin A Deficiency," WHO, Geneva, Switzerland, 68 pgs.

Wu, S., et al. (2020). Microbiota-derived metabolite promotes HDAC3 activity in the gut, Nature 586(7827), 108-112, 31 pgs.

Yang, W., et al. (2020). "Intestinal microbiota-derived short-chain fatty acids regulation of immune cell IL-22 production and gut immunity," Nat Commun, 11:4457, 18 pgs.

Zambelli, F., et al. (2013). "PscanChIP: finding over-represented transcription factor-binding site motifs and their correlations in sequences from ChIP-Seq experiments," Nucleic Acids Res, 41:W535-W543, 9 pgs.

Zeng, R., et al. (2016). "Generation and transcriptional programming of intestinal dendritic cells: Essential role of retinoic acid," Mucosal Immunol, 9(1):183-193, 11 pgs.

International Search Report and Written Opinion dated Jan. 30, 2023 for Application No. PCT/US2022/045511, 8 pgs.

ALDEHYDE DEHYDROGENASE PRODUCING BACTERIA AND METHODS OF USING SAME

CROSS-REFERENCE TO RELATED APPLICATIONS

This application claims priority to and benefit of International Patent Application No. PCT/US22/45511, filed Oct. 3, 2022, which claims priority to and benefit of U.S. Provisional Application Ser. No. 63/251,919 filed Oct. 4, 2021, the contents of which are incorporated in their entirety for all purposes.

STATEMENT REGARDING FEDERALLY-SPONSORED RESEARCH

This invention was made with government support under DK116868 awarded by the National Institutes of Health. The government has certain rights in the invention.

REFERENCE TO SEQUENCE LISTING

A Sequence Listing submitted as an ST.26 XML file via Patent Center is hereby incorporated by reference. The name of the XML file for the Sequence Listing is "CHMC_2021-0903_SeqList_0776671.xml", the date of the creation of the XML file is May 10, 2024, and the size of the XML file is 5,553 bytes.

BACKGROUND

"Microbiome" refers to the collection of genomes from all micro-organisms in a given environment, which may be used interchangeably with the term "microbiota". The human intestinal microbiota normally comprises bacteria, archaea, viruses, fungi, and multicellular parasites, and is believed to be a highly evolved and complex ecosystem that plays an important role in the development and maintenance of homeostasis. (Quigley EMM, Gajula P. Recent advances in modulating the microbiome. F1000Res. 2020 Jan. 27; 9:F1000 Faculty Rev-46. doi: 10.12688/f1000research.20204.1. PMID: 32047611; PMCID: PMC6993818.) Prevention, treatment, and reducing risk of various disease states may be impacted by the state of the gut microbiome. The human gut is relatively sterile at birth and acquires its commensal gut microbiome during birth from the mother's birth canal and thereafter from its oral intake and immediate environment. Id. Microbial diversity rapidly increases over the first three years of life and then stabilizes at a composition that resembles that of an adult. Id. While traditional disease treatment and prevention measures generally involve administration of actives that are affected via the blood stream, modulation of the microbiome in a manner that protects or improves health has not been well established to date. Microbiome-based strategies designed to deliver beneficial microbes, their genes, or the products produced by the microbiome is warranted to improve health and protect against disease. As such, the instant disclosure addresses one or more of the aforementioned needs in the art.

BRIEF SUMMARY

Disclosed herein are methods for enhancing an immune response in an individual in need thereof. The methods, in certain aspects, may comprise administering bacterial aldehyde dehydrogenase, a bacteria that produces aldehyde dehydrogenase, or combinations thereof to an individual. Further disclosed are compositions, such as nutritional compositions, which may comprise bacterial aldehyde dehydrogenase, a bacteria that produces aldehyde dehydrogenase, or combinations thereof.

Disclosed herein are methods for enhancing an immune response in an individual in need thereof. The methods, in certain aspects, may comprise administering bacterial aldehyde dehydrogenase, a bacteria that produces aldehyde dehydrogenase, or combinations thereof to an individual. Further disclosed are compositions, such as nutritional compositions, which may comprise bacterial aldehyde dehydrogenase, a bacteria that produces aldehyde dehydrogenase, or combinations thereof.

BRIEF DESCRIPTION OF THE DRAWINGS

This application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

DETAILED DESCRIPTION

Definitions

Figure 1:
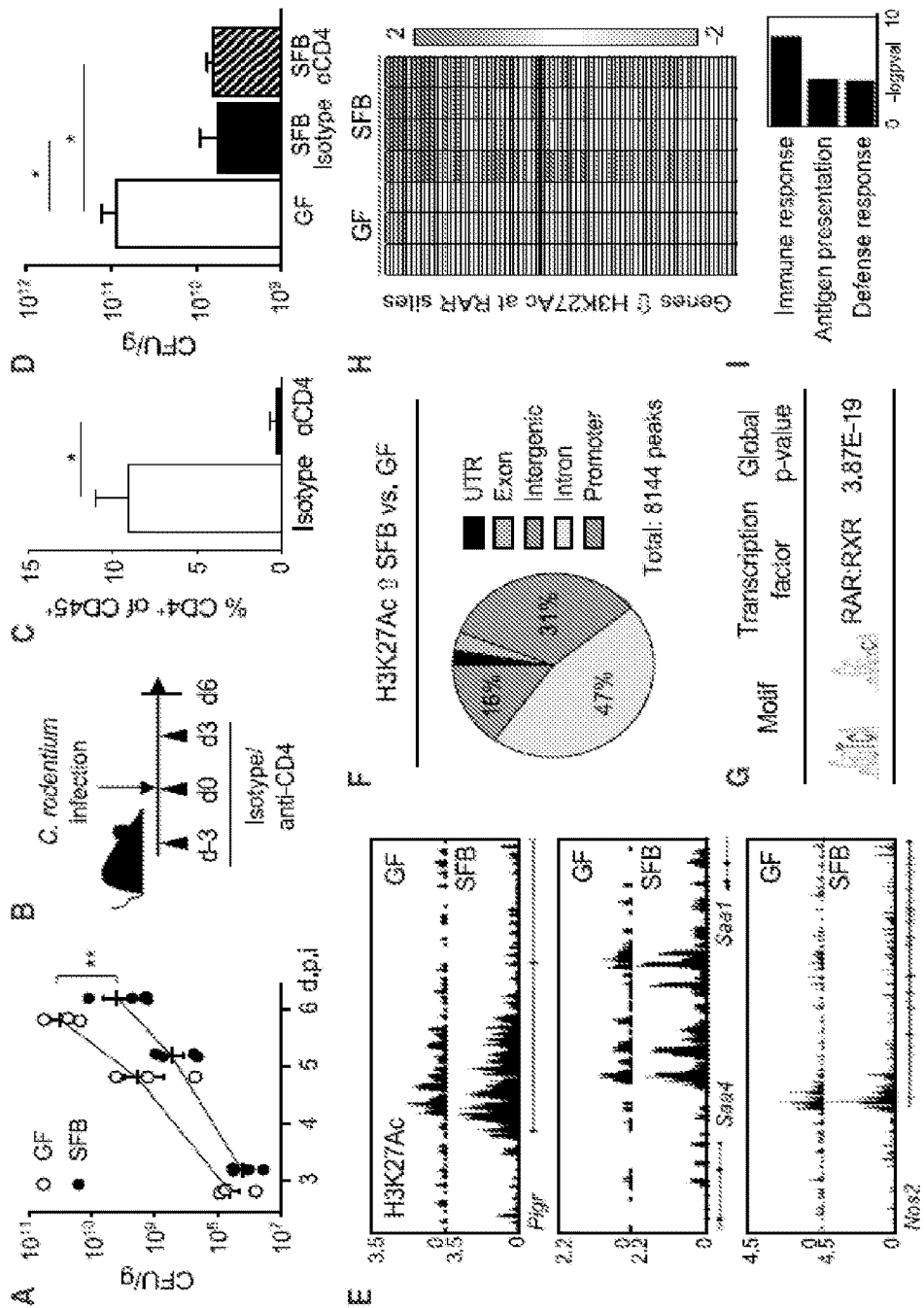
FIG. 1: Commensal SFB primes the intestinal epithelium at retinoic acid receptor sites. (A) Colony-forming units (CFUs) of C. rodentium in stool of infected germ-free (GF) and SFB-monoassociated mice, normalized to sample weight, days 3-6 post-infection (p.i.). (B) Experimental approach. (C) Percent CD4+ T cells in colon from isotype and anti-CD4 treated mice (n=3). Gated on CD45+ cells. (D) C. rodentium CFUs in stool, normalized to sample weight, day 6 p.i. (n=3). (E) Representative sequence tracks for H3K27Ac ChIP-seq from IECs isolated from ileum of GF and SFB-monoassociated mice, normalized to reads per million mapped reads. (F) Genomic distribution of H3K27Ac peaks increased in IECs of SFB versus GF mice, shown as percent of total number of differential peaks. (G) Motif enrichment of retinoic acid receptor (RAR) binding elements at SFB-induced H3K27Ac sites using JASPAR. (H) Heatmap of relative mRNA expression in ileal epithelium harvested from C. rodentium-infected GF and SFB mice at day 6 p.i., represented as relative fold change. (I) Gene ontology for RAR targets that are differentially induced in SFB-infected vs GF-infected from (H). Results are mean±SEM. Data are representative of at least two independent experiments. *p<0.05, **p<0.01.

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, or up to 10%, or up to 5%, or up to 1% of a given value. Alternatively, particularly with respect to biological systems or processes, the term may mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some aspects, the terms refer to humans. In further aspects, the terms may refer to children.

The terms "nutritional composition" or "supplement" as used herein refer to nutritional products intended for ingestion by an individual, including mammals in general such as for veterinary purposes, for generally maintaining or improving the health of that individual. Nutritional compositions may be in the form of a medicine-like product, such as a capsule, tablet, chewable soft gel, syrup, or elixir, or in the form of a nutritional food or beverage product, such as a meal replacement beverage, protein beverage, milk- or soy-based beverage, energy drink, hydration beverage, enhanced water, or mix-in powder for a beverage. Components or ingredients used in a nutritional composition may include flavors, colorants, and excipients, and may include macronutrients (e.g., protein, carbohydrate, or fat) or other optional ingredients (e.g., vitamins or minerals). The terms "pathogen" and "pathogenic" in reference to a bacterium or any other organism or entity includes any such organism or entity that is capable of causing or affecting a disease, disorder or condition of a host organism containing the organism or entity "Sequence identity" as used herein indicates a nucleic acid sequence that has the same nucleic acid sequence as a reference sequence, or has a specified percentage of nucleotides that are the same at the corresponding location within a reference sequence when the two sequences are optimally aligned. For example a nucleic acid sequence may have at least 50%, 60%, 70%, 75%, 80%, 85%, 90%, 95%, 96%, 97%, 98%, 99%, or 100% identity to the reference nucleic acid sequence. The length of comparison sequences will generally be at least 5 contiguous nucleotides, preferably at least 10, 11, 12, 13, 14, 15, 16, 17, 18, 19, 20, 21, 22, 23, 24, or 25 contiguous nucleotides, and most preferably the full length nucleotide sequence. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

The nutritional compositions and methods may comprise, consist of, or consist essentially of the essential elements of the compositions and methods as described herein, as well as any additional or optional element described herein or otherwise useful in nutritional product applications.

Intestinal microbiota are known to influence the development and balance of the host immune system, and have been implicated in prevention of damage induced by opportunistic microbes, in repair of damage to the mucosal barrier, and in influencing systemic autoimmune diseases. Modulation of intestinal microbiota may have certain benefits (see, e.g., US Patent Publication 2015/0224152). The instant application seeks to address this need in the art.

In one aspect, a method of enhancing an immune response in an individual in need thereof is disclosed. In this aspect, the method may comprise administering one or more of the following: bacterial aldehyde dehydrogenase, a bacteria that produces aldehyde dehydrogenase, or a combinations thereof. The method may include administration of one or both of vitamin A and retinol. The administration may be simultaneous with, before, or after the administration of the bacterial aldehyde dehydrogenase and the bacteria that produces aldehyde dehydrogenase. In one aspect, the vitamin A and/or retinol may be administered at a concentration of from about 0.5 to 10 micromolar, or from about 0.75 to about 7.7 micromolar, or from about 1 to about 5 micromolar.

In one aspect, the bacteria that produces aldehyde dehydrogenase may be selected from one or more of Segmented Filamentous Bacteria (SFB), *Candidatus Arthromitus*, *Bifidobacterium bifidum*, *Bacillus bifidum*, *Bacillus cereus*, *Enterococcus faecalis*, *Bacillus subtilis*, *Clostridium perfringes*, *Escherichia Coli* K-12, *Staphylococcus warni*, *Lactobacillus acidophilus*, *Bifidobacterium* sp., *Tissierellia bacterium*, *Bacteroidales bacterium*, *Caloranaerobacter azorensis*, *Keratinibaculum paraultunense*, *Aneurinibacillus* sp., *Bacteroidetes bacterium*, *Tissierella* sp., *Thermohalobacter berrensis*, *Clostridium* sp., *Syntrophomonadaceae bacterium*, *Clostridiales bacterium*, *Bacteroidales bacterium*, *Tenericutes bacterium*, *Paenibacillus assamensis*, *Bacillus kexueae*, *Saliterribacillus persicus*, *Margalitia camelliae*, *Senegalia massiliensis*, *Aquisalibacillus elongatus*, *Sporanaerobacter*, *Syntrophomonadaceae bacterium*, *Aquibacillus sediminis*, *Paludibacteraceae bacterium*, *Cytobacillus oceanisediminis*, *Robertmurraya spiralis*, *Peribacillus saganii*, *Gottschalkia purinilytica*, *Anaerostipes faecalis*, *Lederbergia citrisecundus*, *Cytobacillus firmus*, *Paenibacillus alvei*, *Margalitia shackletonii*, *Sporotomaculum syntrophicum*, *Paenibacillus arenosi*, *Tenericutes bacterium zrk29*, *Neobacillus mesonae*, *Romboutsia* sp., *Flavobacteriaceae bacterium Ap0902*, *Romboutsia*, *Neobacillus mesonae*, *Cytobacillus*, *oceanisediminis*, *Lederbergia citrisecundus*, *Neobacillus bataviensis*, *Halolactibacillus*, *alkaliphilus*, *Alkalihalobacillus wakoensis*, *Neobacillus massiliamazoniensis*, *Piscibacillus halophilus*, *Romboutsia*, *Bacillus dafuensis*, *Piscibacillus halophilus*, *Paenibacillus alvei*, *Gallicola* sp., *Saliterribacillus persicus*, *zArthrobacter citreus*, *Neobacillus vireti*, *Cytophagales bacterium*, *Anaerosalibacter massiliensis*, *Mollicutes bacterium*, *Neobacillus novalis*, *Methanosarcinaceae archaeon*, and combinations thereof.

In one aspect, the bacteria that produces aldehyde dehydrogenase may be genetically modified to produce aldehyde dehydrogenase. In certain aspects, the bacteria that is genetically modified may be selected from *Escherichia coli*, *Lactobacillus* (Lactic acid bacteria), *Bifidobacterium*, and combinations thereof. The genetic modification may comprise insertion of an aldehyde dehydrogenase gene into the bacteria such that the bacteria expresses aldehyde dehydrogenase. In certain aspects, the gene which may be introduced into the bacteria may have at least 90% sequence homology to SEQ ID NO: 1 or SEQ ID NO: 2. The bacteria may have the gene inserted into the bacterial genome, or, in other instances, provided exogenously to the bacterial genome but sufficient for the bacteria to stably express aldehyde dehydrogenase. In one aspect, the aldehyde dehydrogenase gene may be that of SFB (WP_007440235.1) (SEQ ID NO:1), wherein SEQ ID NO: 1 is msiksifysq keffneeatl pinfrmvnli klkkellkne neiytalyed lgkskedafi sefshclnei nyfiknlrsl skpkkvktsf infkskayiy kkpygvclii scwnyplyls lmpligaias gntcilklhp lshntnklie kilreifekc yifstygden elnelldlnf dyifgtgnpn fgkliyekss knlipitlel ggknpcivhd dckidvsckr ivhgkflnsg qtclapdiiy inhkikdefi rkiifyiehf ysedplnfkh yskii-nephf mrlikilenh rdniifgges skeklkiapt iidkneiipc eifgpilqik tydilddiiy slkctpppla ylfttnkti inrflnvpfg ggcindtivh vcennlpfgg lknsgigayh grysfdtfth kksiliksvk vdiksrypns knynlkfikp lfsknk. (SEQ ID NO:1)

In one aspect, the aldehyde dehydrogenase gene may be that of *B. bifidum* ((WP_013390136.1) (SEQ ID NO:2), wherein SEQ ID NO: 2 is mttketaaat ttkqaaarqr afaqldatfr sgvtrplrwr kaqldamarm lrqnatviar avradlgkpa aetalmeigl vldeirfikp rlgrwaarhp kpmhyllqpa vgwtvaepkg valiispwny pvllsfepma daiaagncvc mkpselspht sgvmadliar ymdpqafrvv qggpqettkl leqpfnhify tgggkvgsiv maaaakhltp vtlelggksp vfvdrtanld vaarriawgr finagqtcva pdyvlatsdv ieplagkiak aitrffgsdp qhsdsfgrii narhfdrlta llpdpknpan grtvcggntr rdg-lyiaptv llgvkpdapv mqeeifgpil pilevadaka avefinarpr plaayaftgs krvrrmfere vscgalgfnl plghlissrl pfggvgasgm gsyhgkagfl efshvktvvg kpavpdtlsl vyppydglkk ilisavshtp rvr. (SEQ ID NO:2)

The sequence of the ALDH gene may be modified, provided the modification does not destroy ALDH activity. For example, it is known that conserved catalytic region residues 200-260 (glutamate[E] and cysteine [C]) are required for activity; changing glutamate [E] at amino acid position 209 (SFB ALDH) and 224 (*B. bifidum* ALDH) results in loss of ALDH activity.

In one aspect, the administration of the aforementioned aldehyde dehydrogenase, or bacteria (genetically modified or otherwise) increases retinoic acid in the intestine of said individual. The bacterial aldehyde dehydrogenase, bacterial that produces aldehyde dehydrogenase, or combination thereof may be administered in an amount sufficient to increase retinoic acid (RA) levels in the treated individual. The administration may be sufficient to regulate retinoic-acid sensitive genes in the intestine and liver. In one aspect, the administration may enhance the immune response via a decrease in susceptibility to a pathogenic infection, a decrease in pathogen activity following infection, a shortened period of infection by a pathogen, or combinations thereof. In certain aspects, the pathogenic infection may be one which is caused by an intestinal pathogen. For example, the pathogen may be selected from *Cirobacter* (for example *C. freundii*, *C. koseri*, and *C. braakii*), *Escherichia*, or a combination thereof. *E. coli* strains that may be treated using the disclosed methods may include zoonotic intestinal pathogenic *E. coli* (IPEC) or extraintestinal pathogenic *E. coli* (ExPEC), including the diarrheagenic *E. coli* (DEC) groups such as enteropathogenic *E. coli* (EPEC), enterotoxigenic *E. coli* (ETEC), enteroinvasive *E. coli* (EIEC), enteroaggregative *E. coli* (EAggEC), diffusely adherent *E. coli* (DAEC), enterohemorrhagic *E. coli* (EHEC) and Vero cytotoxin-producing *E. coli* (VTEC) or Shiga toxin-producing *E. coli* (STEC).

The individual being administered the disclosed agents and compositions may be an adult, less than 18 years of age, or less than 16, 15, 14, 13, 12, 11, 10, 9, 8, 7, 6, 5, 4, 3, 2, or 1 year of age, or a neonate. In certain aspects, the individual may be a pregnant mammal, preferably a pregnant human. Administration of the compositions to the pregnant individual may provide one or more benefits as disclosed herein to the fetus. In certain aspects the individual may be an individual who has been treated with an antibiotic.

The method may comprise administering the bacteria as a unit dose. The unit dose may comprise from about $10^3$ colony forming units to about $10^8$ colony forming units. In one aspect, the unit dose comprises about $10^3$ colony forming units, wherein the unit dose is formulated for administration to a neonate. In one aspect, the unit dose comprises about $10^8$ colony forming units, wherein the unit dose is formulated for administration to an adult. In other aspects, the bacteria may be administered in a food product, such as a nutritional composition.

Nutritional Compositions

In one aspect, a nutritional composition comprising bacterial aldehyde dehydrogenase, a bacterial that produces aldehyde dehydrogenase, or combinations thereof is disclosed. The nutritional composition may comprise one or both of vitamin A and retinol. The vitamin A and/or retinol may be present in the nutritional composition at a concentration of from about 0.5 to 10 micromolar, or from about 0.75 to about 7.7 micromolar, or from about 1 to about 5 micromolar. The composition may comprise any combination of the aforementioned bacteria as disclosed herein. The nutritional composition may be formulated for enteral administration, for example, oral administration, and may, in certain aspects, provide a unit dose of from about $10^3$ colony forming units to about $10^8$ colony forming units. In certain aspects, the nutritional composition may provide a unit dose of about $10^3$ colony forming units and be formulated for a child (under 18, or pre-pubescent), or a unit dose of about $10^8$ colony forming units and be formulated for an adult.

The nutritional compositions may comprise a carbohydrate. Non-limiting examples of suitable carbohydrates or sources thereof in the nutritional compositions may be selected from the group of maltodextrin, hydrolyzed or modified starch or cornstarch, glucose polymers, corn syrup, corn syrup solids, rice-derived carbohydrates, sucrose, glucose, fructose, lactose, high fructose corn syrup, honey, sugar alcohols (e.g., maltitol, erythritol, or sorbitol), and combinations thereof. A nutritional composition may comprise a carbohydrate concentration of from about 5 wt % to about 70 wt %, including from about 7 wt % to about 60 wt %, including from about 10 wt % to about 55 wt %, by weight of the nutritional composition.

The nutritional compositions may comprise a fat. Non-limiting examples of suitable fats in the nutritional compositions described herein may be selected from the group of coconut oil, fractionated coconut oil, soy oil, corn oil, olive oil, safflower oil, high oleic safflower oil, medium chain triglyceride oil, sunflower oil, high oleic sunflower oil, palm and palm kernel oils, palm olein, canola oil, walnut oil, flaxseed oil, marine oils, cottonseed oil, borage oil, algal oils, fungal oils, and combinations thereof. Fat concentrations may range from about 0.5 wt % to about 35 wt %, including from about 0.75 wt % to about 30 wt %, including from about 1 wt % to about 28 wt %, and also including from about 2 wt % to about 5 wt %, by weight of the nutritional composition.

The nutritional compositions may comprise a protein. Non-limiting examples of suitable protein or sources thereof in the nutritional compositions may be selected from the group of partially hydrolyzed or non-hydrolyzed proteins derived from any suitable source, such as milk (e.g., casein or whey), animal (e.g., meat or fish), cereal (e.g., rice or wheat), vegetable (e.g., pea, potato, or bean), or combinations thereof. Non-limiting examples of such proteins include whole cow's milk, partially or completely defatted milk, milk protein isolates, milk protein concentrates, casemates, casein protein isolates, whey protein, whey protein concentrates, soy protein isolates, soy protein concentrates, pea protein isolates, pea protein concentrates, hydrolyzed yeast, potato, rice, wheat, canola, animal collagen, gelatin, bovine colostrum, human colostrum, glycomacropeptides, mycoproteins, amino acids, and combinations thereof. Protein concentrations may range from about 1 wt % to about 85 wt %, from about 5 wt % to about 50 wt %, from about 7 wt % to about 32 wt %, or from about 8 wt % to about 30 wt %, by weight of the nutritional composition.

The supplements may also include one or more masking agents to reduce or otherwise obscure unappealing flavors and/or after taste. Suitable masking agents may include natural and artificial sweeteners, sodium sources such as sodium chloride, and hydrocolloids, such as guar gum, xanthan gum, carrageenan, gellan gum, and combinations thereof. The amount of masking agent in the supplement may vary depending upon the particular masking agent selected, other ingredients in the nutritional composition formulation, and other supplement or product target variables. Exemplary amounts may range from at least 0.1 wt %, including from about 0.15 wt % to about 3.0 wt %, and also including from about 0.18 wt % to about 2.5 wt %, by weight of the nutritional composition formulation.

The compositions provided herein may be formulated into liquid preparations such as suspensions, syrups, elixirs, and the like. Unit dosage forms for oral administration may include tablets and capsules, and may be configured for administration once a day, twice a day, or more. For enteral administration (including oral), the compositions may be provided as a tablet, aqueous or oil suspension, dispersible powder or granule, emulsion, hard or soft capsule, syrup or elixir. The compositions may include one or more of the following agents: sweeteners, flavoring agents, coloring agents and preservatives.

Tablets may be uncoated or coated by known methods to delay disintegration and absorption in the gastrointestinal tract and thereby provide a sustained action over a longer period of time. For example, a time delay material such as glyceryl monostearate may be used. When administered in solid form, such as tablet form, the solid form typically comprises from about 0.001 wt. % or less to about 50 wt. % or more of active ingredient(s), for example, from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Tablets may contain the active ingredients in admixture with non-toxic pharmaceutically acceptable excipients including inert materials. For example, a tablet may be prepared by compression or molding, optionally, with one or more additional ingredients. Compressed tablets may be prepared by compressing in a suitable machine the active ingredients in a free-flowing form such as powder or granules, optionally mixed with a binder, lubricant, inert diluent, surface active or dispersing agent. Molded tablets may be made by molding, in a suitable machine, a mixture of the powdered active agent moistened with an inert liquid diluent.

Controlled release formulations may be employed wherein the active agent or analog(s) thereof is incorporated into an inert matrix that permits release by either diffusion or leaching mechanisms. Slowly degenerating matrices may also be incorporated into the formulation. Other delivery systems may include timed release, delayed release, or sustained release delivery systems.

Coatings may be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments may be added for identification or to characterize different combinations of active agent doses.

In some aspects, the compositions provided herein may be provided to an administering physician or other health care professional in the form of a kit. The kit is a package which houses a container which contains the active agent(s) in a suitable pharmaceutical composition, and instructions for administering the pharmaceutical composition to a subject. The kit may optionally also contain one or more additional therapeutic agents currently employed for treating a disease state as described herein. For example, a kit containing one or more compositions comprising active agents provided herein in combination with one or more additional active agents may be provided, or separate pharmaceutical compositions containing an active agent as provided herein and additional therapeutic agents may be provided. The kit may also contain separate doses of a active agent provided herein for serial or sequential administration. The kit may optionally contain one or more diagnostic tools and instructions for use. The kit may contain suitable delivery devices, e.g., syringes, and the like, along with instructions for administering the active agent(s) and any other therapeutic agent. The kit may optionally contain instructions for storage, reconstitution (if applicable), and administration of any or all therapeutic agents included. The kits may include a plurality of containers reflecting the number of administrations to be given to a subject.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus may be considered to constitute examples of modes for its practice. However, those of skill in the art should, in light of the present disclosure, appreciate that many changes may be made in the specific embodiments that are disclosed and still obtain a like or similar result without departing from the spirit and scope of the invention.

Example 1. Applicant has found that intestinal epithelial cell (IEC)-associated commensal bacteria, segmented filamentous bacteria (SFB) promote early protection against the pathogen *Citrobacter rodentium*, independent of CD4+ T cells. SFB induced histone modifications in IECs at sites enriched for retinoic acid receptor motifs, suggesting that SFB may enhance defense through retinoic acid (RA). Consistent with this, inhibiting RA signaling suppressed SFB-induced protection. Intestinal RA levels were elevated in SFB mice, despite the inhibition of mammalian RA production, indicating that SFB directly modulate RA. Interestingly, RA was produced by intestinal bacteria, and the loss of bacterial-intrinsic aldehyde dehydrogenase activity decreased the RA levels and increased infection. These data reveal RA as an unexpected microbiota-derived metabolite that primes innate defense and suggests that pre- and probiotic approaches to elevate RA could prevent or combat infections.

The mammalian intestine is inhabited by trillions of commensal microbes, collectively referred to as the microbiota. In addition to innocuous commensals, the gastrointestinal tract is constantly at risk of invasion and infection by pathogenic microbes. Interactions between the intestinal microbiota and the mammalian host are essential for effective defense against pathogens, as loss of the microbiota in germ-free and antibiotic-treated animals leads to increased susceptibility to enteric and non-enteric infection (Abt and Pamer, 2014; Benson et al., 2009; Ganal et al., 2012; Ivanov et al., 2009).

Intestinal epithelial cells (IECs) reside at the direct interface between the host and commensal microbes and, therefore, carry the potential to critically respond to signals from the microbiota. Besides functioning as a physical barrier, these cells actively respond to microbial challenges by secreting antimicrobial peptides, mucins, chemokines and cytokines that prime and regulate innate and adaptive immunity (Gallo and Hooper, 2012; *Peterson and Artis,* 2014; Ramanan and Cadwell, 2016). IECs are also equipped to sense microbial stimuli through various membrane and cytoplasmic pattern-recognition receptors (Price et al., 2018).

In addition to canonical microbial sensing pathways, epigenetic mechanisms enable environmental signals to instruct cellular responses and represent another interface by which microbiota can impact mammalian cells (Amatullah and Jeffrey, 2020; Woo and Alenghat, 2017). Consistent with this, epigenetic-modifying enzymes in IECs integrate microbiota-derived signals to regulate intestinal homeostasis and immunity (Ansari et al., 2020; Navabi et al., 2017; Takahashi et al., 2009; Wu et al., 2020). Epigenetic-modifying enzymes mediate covalent chromatin modifications that alter DNA accessibility and gene expression. Thus, epigenetic modifications that are sensitive to the microbiota may identify regulatory pathways that can enhance host defense to infection (Arrowsmith et al., 2012; Kelly et al., 2018). Increasing evidence highlights that microbiota-derived metabolites mediate the host-microbiota relationship (Lavelle and Sokol, 2020; McCarville et al., 2020; Rooks and Garrett, 2016). Commensal bacteria generate a variety of metabolites through either direct synthesis or breakdown of dietary components that can be absorbed in the intestine and potentially travel systemically (Matsumoto et al., 2018; Wikoff et al., 2009). For example, well-characterized bacterial-derived short-chain fatty acids that are produced by bacteria in the intestine can regulate local cells as well as distant tissues (Chang et al., 2014; Dalile et al., 2019; Fellows et al., 2018; Furusawa et al., 2013; Kaiko et al., 2016; Yang et al., 2020). However, despite the appreciation that commensal bacteria prime enhanced innate defenses, the underlying pathways and microbiota-derived cues that decrease host susceptibility to pathogenic infection remain poorly defined.

*Citrobacter rodentium* is a well-characterized murine bacterial pathogen that causes similar pathology to human enteropathogenic *Escherichia coli* (Mundy et al., 2005). *C. rodentium* initiates intestinal infection by adhering to the apical surface of IECs in the large intestine. Defense against *C. rodentium* requires signals from commensal microbes, as microbiota-depleted animals exhibit higher *C. rodentium* levels and impaired ability to clear the infection compared to microbiota-replete counterparts (Kamada et al., 2012; Osbelt et al., 2020; Woo et al., 2019). Segmented Filamentous Bacteria (SFB) are commensal bacteria (Jonsson et al., 2020) that protect against enteric pathogens such as *C. rodentium* (Chung et al., 2012; Garland et al., 1982; Heczko et al., 2000; Ivanov et al., 2009; Shi et al., 2019). Unlike the majority of commensal bacteria that are spatially separated from the epithelium, SFB directly binds to IECs in the distal small intestine (Atarashi et al., 2015; Ivanov et al., 2009; Ladinsky et al., 2019). SFB protects against *C. rodentium* infection, despite colonizing a distinct anatomical region of the intestine. Therefore, SFB likely modulates mammalian pathways rather than directly competing with *C. rodentium*, as has been shown for commensal *E. coli* and *Bacteroides thetaiotaomicron* (Kamada et al., 2012). Previous studies have described that decreased *C. rodentium* infection in mice colonized with SFB were associated with SFB-induced expansion of CD4+ Th17 cells that produce IL-17 and IL-22 (Goto et al., 2014; Ivanov et al., 2009). Here, Applicant discovered that SFB also decreases initial susceptibility to *C. rodentium* infection prior to regulation by CD4+ T cells. ChIP-seq analyses in uninfected mice revealed that SFB colonization induced epigenetic modifications in IECs at retinoic acid receptor (RAR) motifs. Consistent with enhanced transcriptional potential, IECs from SFB-colonized mice exhibited greater induction of RAR targets relative to IECs from germ-free mice post-*C. rodentium* infection, suggesting that SFB may enhance innate defense through the RAR ligand, retinoic acid (RA). Interestingly, intestinal RA levels were increased in mice colonized with SFB and inhibiting RA signaling in SFB-colonized mice increased pathogen burden. However, SFB-dependent RA accumulation was not dependent on mammalian RA production. Instead, SFB and other commensal bacteria expressed dehydrogenase genes homologous to a microbial enzyme that converts vitamin A to RA. Remarkably, these enzymes are highly prevalent in the human microbiota, and their enzymatic activity alters RA levels and their enzymatic activity alters RA levels and host regulation in the intestine.

Results

Commensal SFB Protects Against Early Infection Independently of CD4+ T Cells

*C. rodentium* is an enteric pathogen that follows a similar pathogenesis to human enteropathogenic *E. coli* and establishes initial colonization within 2-3 days, reaching peak of infection around days 8-10 post-infection (Symonds et al., 2009). The presence of SFB in the intestinal microbiota protects against *C. rodentium* infection (Ivanov et al., 2009). Furthermore, Applicant found that colonizing germ-free (GF) mice with SFB alone was sufficient to significantly lower pathogen burdens compared to GF mice (FIG. 1A). Interestingly, *C. rodentium* protection in SFB-colonized mice was already evident within the early phase of infection (days 3-6), suggesting that SFB may promote innate responses that decrease *C. rodentium* burden. SFB-colonization has previously been shown to induce CD4+ Th7 differentiation. In mice, Th17 cells activated during the peak of *C. rodentium* infection (day 10-14) mediate clearance of the pathogen by producing IL-22 and IL-17 (Ivanov et al., 2009; Omenetti et al., 2019). However, it is unclear whether Th17 cells are involved in SFB-dependent defense against *C. rodentium* during initial stages of infection. To test the involvement of Th17 cells and other CD4+ T helper cell populations in SFB-dependent protection against early phase *C. rodentium* infection, anti-IL-17A or anti-CD4 depleting antibodies were administered prior and during infection (FIG. 1B). Mice receiving IL-17A blocking antibodies exhibited similar pathogen levels early post-infection (FIG. S1A). Anti-CD4 treatment effectively depleted CD4+ T cells systemically (FIG. S1B) as well as in the colon where *C. rodentium* infects (FIG. 1C). Interestingly, SFB colonization led to decreased *C. rodentium* burden even when mice lacked CD4+ T cells (FIG. 1D), indicating that CD4+ T cells are not required for initial SFB-dependent protection.

Intestinal epithelium is transcriptionally primed by SFB at retinoic acid receptor motifs Given that enhanced initial defense against *C. rodentium* was not reliant on SFB-induced CD4+ T cells (FIG. 1D), Applicant hypothesized that IECs may be important mediators of SFB-driven defense. IECs are critically poised to respond to the microbiota and pathogens and thus play an important role in innate defense. To investigate whether SFB alters the transcriptional state of IECs, Applicant first performed chromatin-immunoprecipitation sequencing (ChIP-seq) on primary IECs isolated from ileum of GF and SFB-monoassociated mice for the histone modification H3 lysine 27 acetylation (H3K27Ac) that characterizes primed and active chromatin (Creyghton et al., 2010). These global analyses revealed many genes that exhibit increased levels of histone H3K27Ac in response to SFB colonization, as indicated by differential peaks at multiple representative genes (FIG. 1E). The majority of the sites with differential H3K27Ac in IECs from SFB-colonized mice occurred in regulatory gene elements (FIG. 1F), consistent with the known link between H3K27Ac and transcriptionally primed genes (Creyghton et al., 2010; Rada-Iglesias et al., 2011).

To determine whether regions of increased histone acetylation were regulated by a shared transcription factor and/or pathway, motif enrichment analyses were performed. Sites with elevated H3K27Ac in IECs of SFB-colonized mice were significantly enriched for retinoic acid receptor (RAR) motifs (FIG. 1G). RARs are a family of nuclear hormone receptors that regulate chromatin accessibility and gene expression by recruiting epigenetic modifiers and cofactors. Interestingly, expression of a large proportion of RAR targets with increased H3K27Ac were significantly upregulated in IECs from SFB mice during *C. rodentium* infection, compared to IECs from infected GF mice (FIG. 1H). Pathway analyses further revealed that the majority of the SFB-sensitive epigenetically primed RAR targets were enriched in host defense pathways (FIG. 1I). These data demonstrate that commensal SFB modifies the epigenetic and transcriptional state of the intestinal epithelium and suggest that SFB-dependent regulation of RAR in IECs may prime innate defense against infection.

Figure 2:
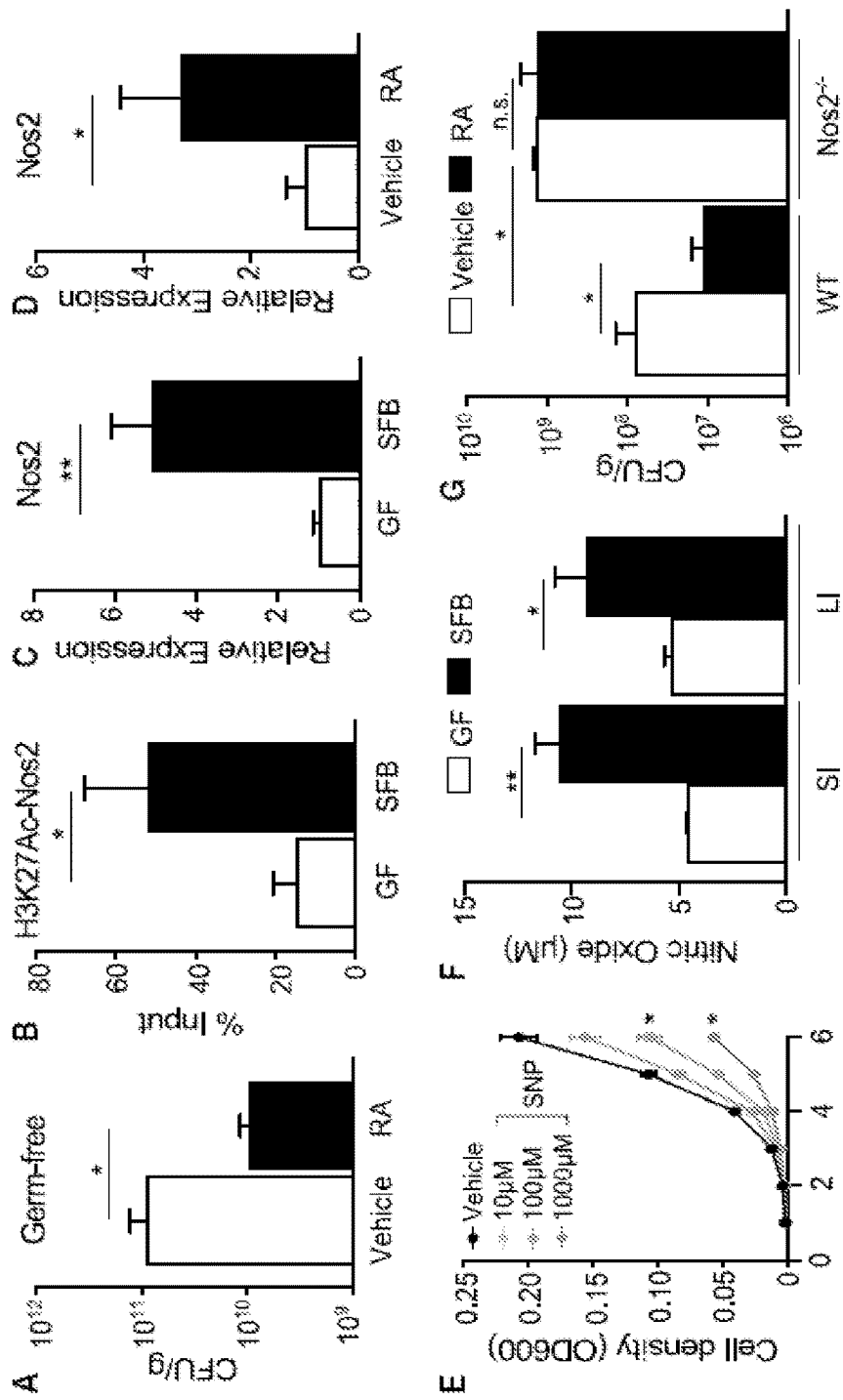
FIG. 2: Retinoic acid improves C. rodentium defense through Nos2 regulation. (A) C. rodentium CFUs in stool of GF mice treated with all-trans retinoic acid (RA), day 6 p.i. (n=3-4). (B) ChIP-qPCR for H3K27Ac at Nos2 RAR site, shown as percent of input (n=3). (C, D) mRNA expression levels in ileal epithelium, normalized to GF or vehicle-treated mice (n=3-4). (E) Bacterial cell density of C. rodentium (n=3). (F) Nitric oxide levels (NO3-+NO2-) in lumen of small (SI) and large (LI) intestine (n=3). (G) C. rodentium CFUs in stool, normalized to sample weight, day 6 p.i. (n=3). Results are mean±SEM. Data are representative of three independent experiments. *p<0.05, **p<0.01. n.s., not significant.

Retinoic acid improves *C. rodentium* defense through Nos2 regulation. RARs are a family of transcription factors that bind as heterodimers with retinoid X receptors to retinoic acid response elements in the DNA. These receptors are activated by binding to the vitamin A metabolite, retinoic acid (RA). Ligand binding results in recruitment of molecular machinery that modifies local chromatin and promotes active transcription. RA and vitamin A availability can modulate *C. rodentium* and *E. coli* infection in mice and humans, respectively (Cabrera et al., 2014; McDaniel et al., 2015), provoking the hypothesis that RA may mediate the SFB-induced decrease in *C. rodentium*. Therefore, to first test whether RA is protective against *C. rodentium* in an SFB-deficient context, GF mice were treated with exogenous RA prior to and throughout the duration of infection. Administration of RA to GF mice was sufficient to protect GF mice against *C. rodentium* (FIG. 2A), similar to protective effects described for RA-treated microbiota-sufficient mice (Snyder et al., 2019). *C. rodentium* growth and viability was not directly impaired by RA in vitro (FIG. S2A), indicating that decreased *C. rodentium* infection from RA Nitric oxide synthase 2 (Nos2, iNOS) is an enzyme that is highly expressed in the intestinal pithelium and generates nitric oxide (NO), which has potent antimicrobial activity against *C. rodentium* (Vallance et al., 2002). SFB significantly increased histone H3K27Ac at an RAR site within the Nos2 gene (FIG. 2B). This epigenetic alteration was localized to the small intestine where SFB colonizes (FIG. S2B). SFB also induced ileal epithelial Nos2 expression in relation to GF mice (FIG. 2C) and similar induction of Nos2 mRNA occurred in IECs harvested from GF mice following treatment with exogenous RA (FIG. 2D). Consistent with previous work (Vallance et al., 2002), *C. rodentium* survival in vitro was impaired with the NO-donor sodium nitroprusside (SNP) (FIG. 2E). Furthermore, SFB colonization increased luminal NO levels in the small and large intestine (FIG. 2F). These data collectively provoked the hypothesis that Nos2 functions downstream of RA to decrease *C. rodentium* levels. To test this mechanism, *C. rodentium* infection levels were compared in mice lacking Nos2 (Nos2−/−) and WT mice in the absence or presence of exogenous RA. As expected, Nos2−/− mice exhibited elevated infection relative to WT mice (FIG. 2G). Interestingly, RA administration decreased *C. rodentium* infection in WT mice but did not alter pathogen levels in Nos2−/− mice (FIG. 2G). Collectively, these data highlight Nos2 as an SFB-sensitive, epigenetically regulated RAR target in IECs that mediates RA-induced protection against *C. rodentium*

Figure 3:
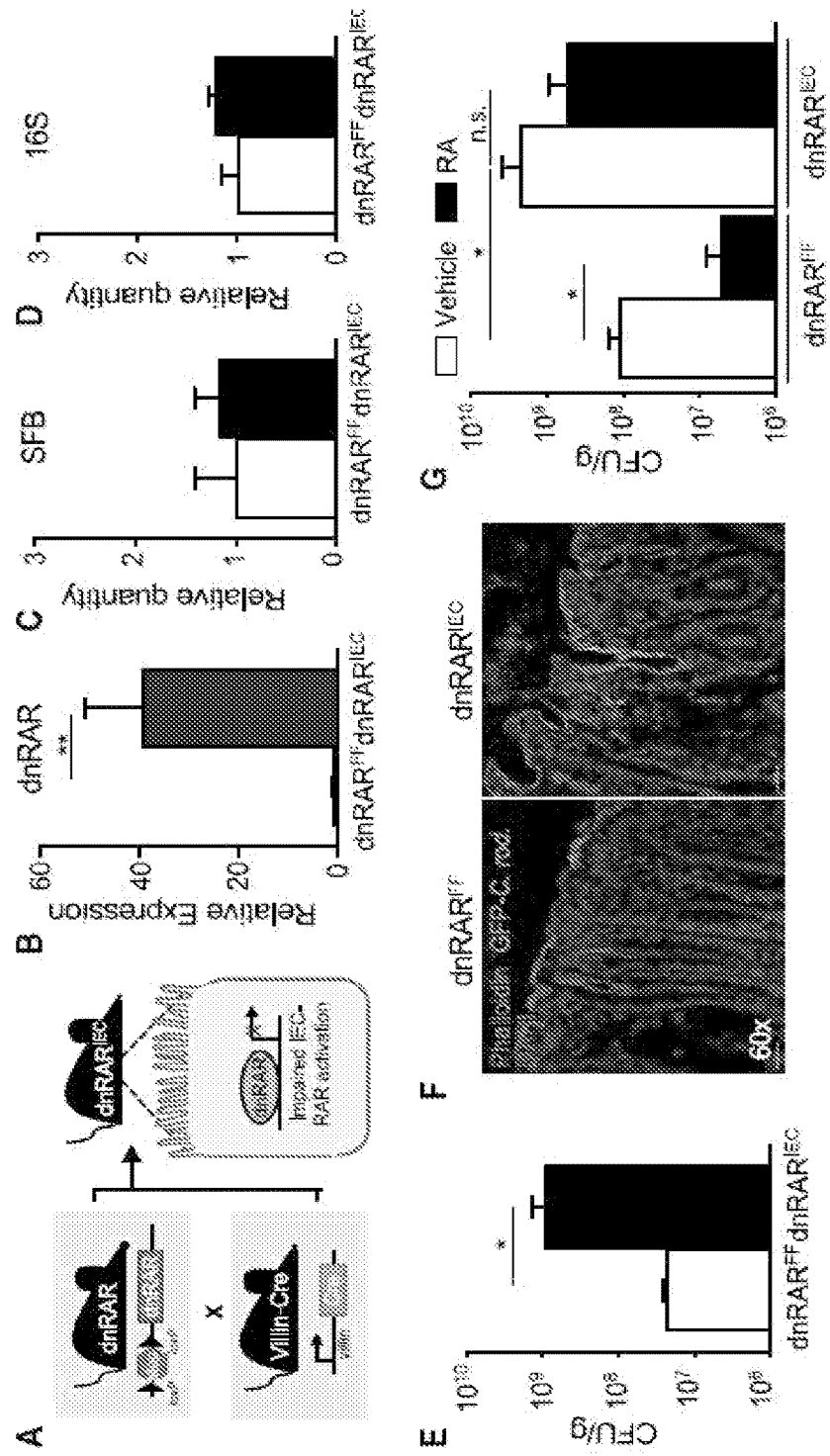
FIG. 3: IEC-intrinsic RAR activation enhances defense against C. rodentium. (A) Control mice with a floxed stop-codon upstream of a dominant-negative RAR (dnRAR$^{F/F}$) were crossed to mice expressing IEC specific villin-cre recombinase to generate IEC-specific dnRAR expressing mice (dnRAR$^{IEC}$). (B) dnRAR mRNA expression in IECs of dnRAR$^{FF}$ and dnRAR$^{IEC}$ mice (n=3-4), normalized to dnRAR$^{FF}$. (C, D) Relative level of (C) SFB and (D) 16S rRNA DNA by qPCR in feces from dnRAR$^{FF}$ and dnRAR$^{IEC}$ mice (n=4), normalized to dnRAR$^{FF}$. (E) *C. rodentium* CFUs in stool, normalized to sample weight, day 6 p.i. (n=3-4). (F) Immunofluorescent staining of distal large intestine from dnRAR$^{FF}$ and dnRAR$^{IEC}$ mice infected with GFP-expressing *C. rodentium* (Green: GFP-*C. rodentium*, red: Phalloidin, blue: DAPI). (G) *C. rodentium* CFUs in stool, normalized to sample weight, day 6 p.i. (n=5-6). Results are mean±SEM. Data are representative of three independent experiments. *p<0.05, **p<0.01. n.s., not significant.

IEC-intrinsic RAR activation enhances defense against *C. rodentium*. The role of RA in infection has been extensively investigated in immune cells (Hall et al., 2011a) and recent studies demonstrated that loss of RAR expression or impaired RAR responsiveness in IECs alters intestinal development and defense (Gattu et al., 2019; Iyer et al., 2020; Jijon et al., 2018). To test whether IEC-intrinsic RA signaling specifically contributes to RA mediated protection against *C. rodentium* infection, Applicant generated an IEC-specific dominant-negative RAR (dnRAR) transgenic mouse (FIG. 3A) that expresses non-responsive RAR specifically in IECs (dnRAR$^{IEC}$) (FIG. 3B). Mice expressing dnRAR did not exhibit significant differences in intestinal length (FIGS. S3A and S3B), histology (FIGS. S3C and S3D) or barrier function (FIG. S3E). Furthermore, SFB and 16S DNA levels were similar in dnRAR$^{FF}$ and dnRAR$^{IEC}$ mice (FIGS. 3C and 3D). Interestingly, dnRAR$^{EC}$ mice exhibited significantly higher *C. rodentium* infection compared with floxed controls (dnRAR$^{FF}$) (FIGS. 3E and 3F), similar to the effect previously described for *Salmonella Typhimurium* infection (Gattu et al., 2019; Iyer et al., 2020). To next decipher whether RA-driven protection requires epithelial RAR activation, control and dnRAR$^{IEC}$ mice were treated with RA and infected with *C. rodentium*. As described above, RA-treatment decreased infection in control dnRAR$^{FF}$ mice (FIG. 3G); however, this RA-induced protection was greatly reduced in dnRAR$^{IEC}$ mice (FIG. 3G), indicating that epithelial-intrinsic RAR activity significantly contributes to RA-dependent defense against *C. rodentium*.

Figure 4:
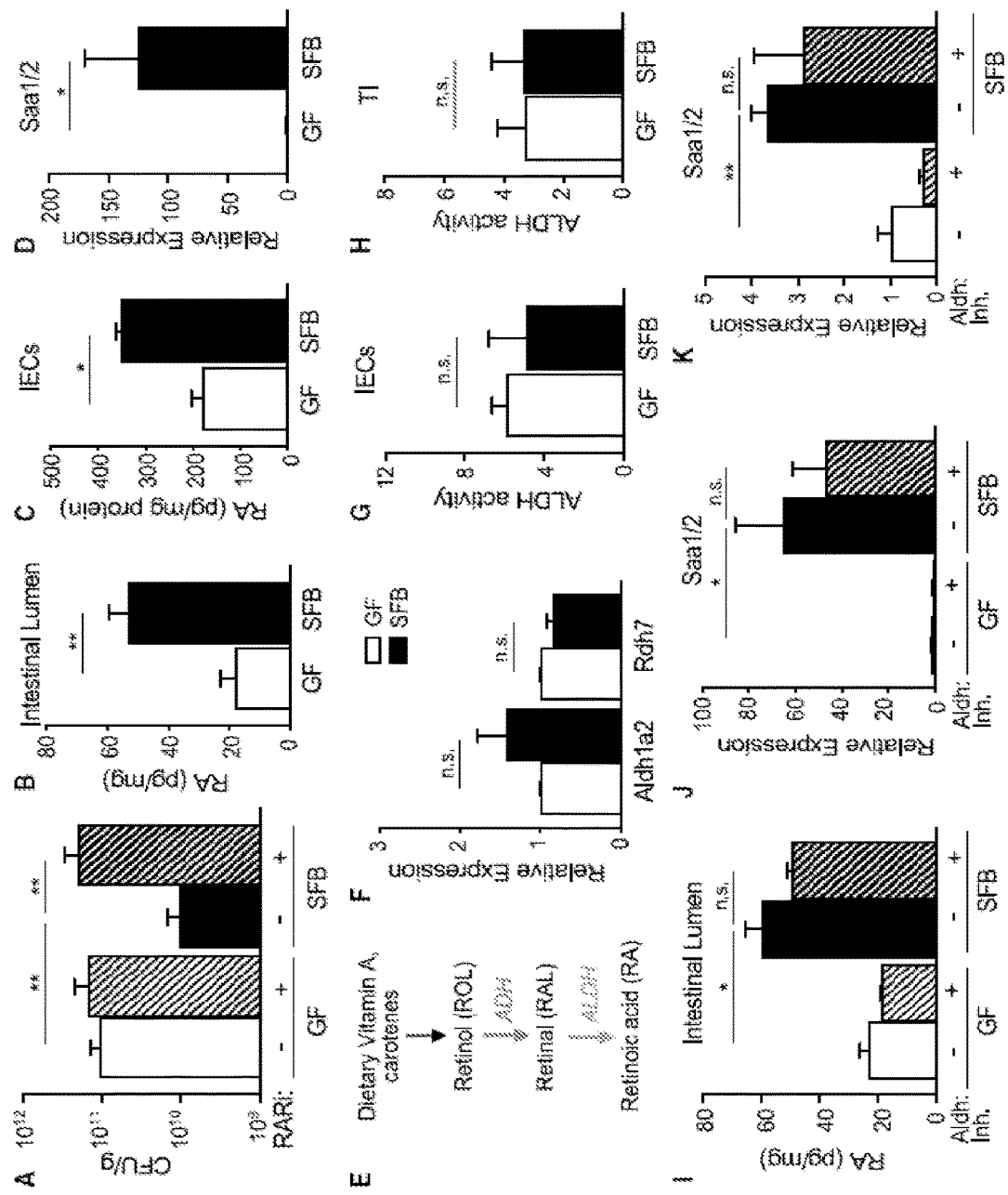
FIG. 4: SFB increases intestinal retinoic acid levels despite inhibition of host production. (A) *C. rodentium* CFUs in stool of GF and SFB mice−/+ RAR inhibitor (RARi; BMS493), normalized to sample weight, day 6 p.i. (n=4-6). (B, C) Retinoic acid concentration in (B) fecal samples and (C) IECs collected from GF and SFB mice (n=4), normalized to sample weight. (D) mRNA expression in IECs of GF and SFB mice (n=4), normalized to GF. (E) Schematic of mammalian vitamin A metabolism to retinoic acid. (F) mRNA expression in IECs of GF and SFB mice (n=4), relative to GF. (G, H) ALDH activity in (G) IECs and (H) terminal ileum (TI) tissue (n=3). (I) Retinoic acid concentration in stool of GF and SFB mice treated with Aldh1a2 inhibitor, normalized to sample weight (n=4). (J, K) mRNA expression in (J) IECs (n=4) or (K) intestinal organoids (n=4-6). Results are mean±SEM. Data are representative of three independent experiments. *p<0.05, **p<0.01. n.s., not significant.

SFB increases intestinal retinoic acid levels despite inhibition of host production. Our initial findings demonstrated that SFB increased histone acetylation at RAR target genes in IECs (FIGS. 1E-1G) and that the timing and magnitude of RA-induced protection against *C. rodentium* parallels the phenotype observed with SFB colonization (FIGS. 1A and 2A). Thus, Applicant hypothesized that RA may mediate SFB-dependent defense against this pathogen. To test whether SFB promotes protection from infection by activating RAR, GF and SFB-colonized mice were treated with an RAR-inverse agonist (RARi: BMS493) that blocks RA-RAR activation (Metzler et al., 2018). RARi treatment did not alter SFB colonization (FIG. S4A). Remarkably, impaired RA-RAR activation abrogated the protective effect of SFB against *C. rodentium*, whereas pathogen levels in GF mice were largely unaffected (FIG. 4A). Given that RARs are activated by their RA ligand, intestinal levels of RA were compared between GF and SFB-colonized mice. Interestingly, SFB mice exhibited significantly elevated RA in intestinal contents and IECs compared to GF mice (FIGS. 4B and 4C). Consistent with increased local RA, expression of the RA-sensitive gene Serum amyloid A-1/2 (Saa1/2) was increased in IECs from SFB-colonized mice (FIG. 4D.)

RA is generated from the vitamin A-derivative retinol in a two-step oxidation reaction involving retinol dehydrogenases (ADH, RDH) and retinaldehyde dehydrogenases (ALDH, RALDH) (FIG. 4E). IECs are equipped to generate RA, and it was recently reported that microbiota modulates intestinal tissue RA levels by regulating expression of Rdh7 in IECs (Grizotte-Lake et al., 2018). However, Applicant found that expression of key enzymes involved in the conversion of vitamin A to RA (Aldh1a2 and Rdh7) were similarly expressed in IECs of GF and SFB mice (FIG. 4F). Furthermore, ALDH activity was similar in IECs and ileal tissue of GF and SFB-colonized mice (FIGS. 4G and 4H), suggesting that host-intrinsic enzymes required for RA production in the intestine are not primarily impacted by SFB alone. To further investigate the contribution of host RA synthesis on intestinal RA levels in SFB colonized mice, mice were treated with an Aldh1a2 inhibitor, WIN18446, that blocks mammalian RA production (Arnold et al., 2015; Paik et al., 2014; Seamons et al., 2020). As predicted, administration of WIN18446 decreased mammalian ALDH enzymatic activity (FIG. S4B) and downstream gene expression (FIG. S4C). However, despite host ALDH inhibition, RA levels and IEC-expression of Saa1/2 remained elevated in SFB colonized mice (FIGS. 4I and 4J). SFB levels in the intestine were similar following WIN18446 administration (FIG. S4D). To directly interrogate the epithelial Saa1/2 response to SFB without other cellular contributions, intestinal organoids were examined in the absence or presence of SFB. As expected, inhibition of mammalian Aldh1a2 decreased basal Saa1/2 expression in intestinal organoids (FIG. 4K). However, consistent with our findings in vivo, SFB-exposure induced Saa1/2 expression in intestinal organoids despite pharmacological inhibition of mammalian Aldh1a2 (FIG. 4K). Taken together, these findings suggest that the SFB-dependent increase in intestinal RA and regulation of epithelial responses is largely bacterial-dependent.

Figure 5:
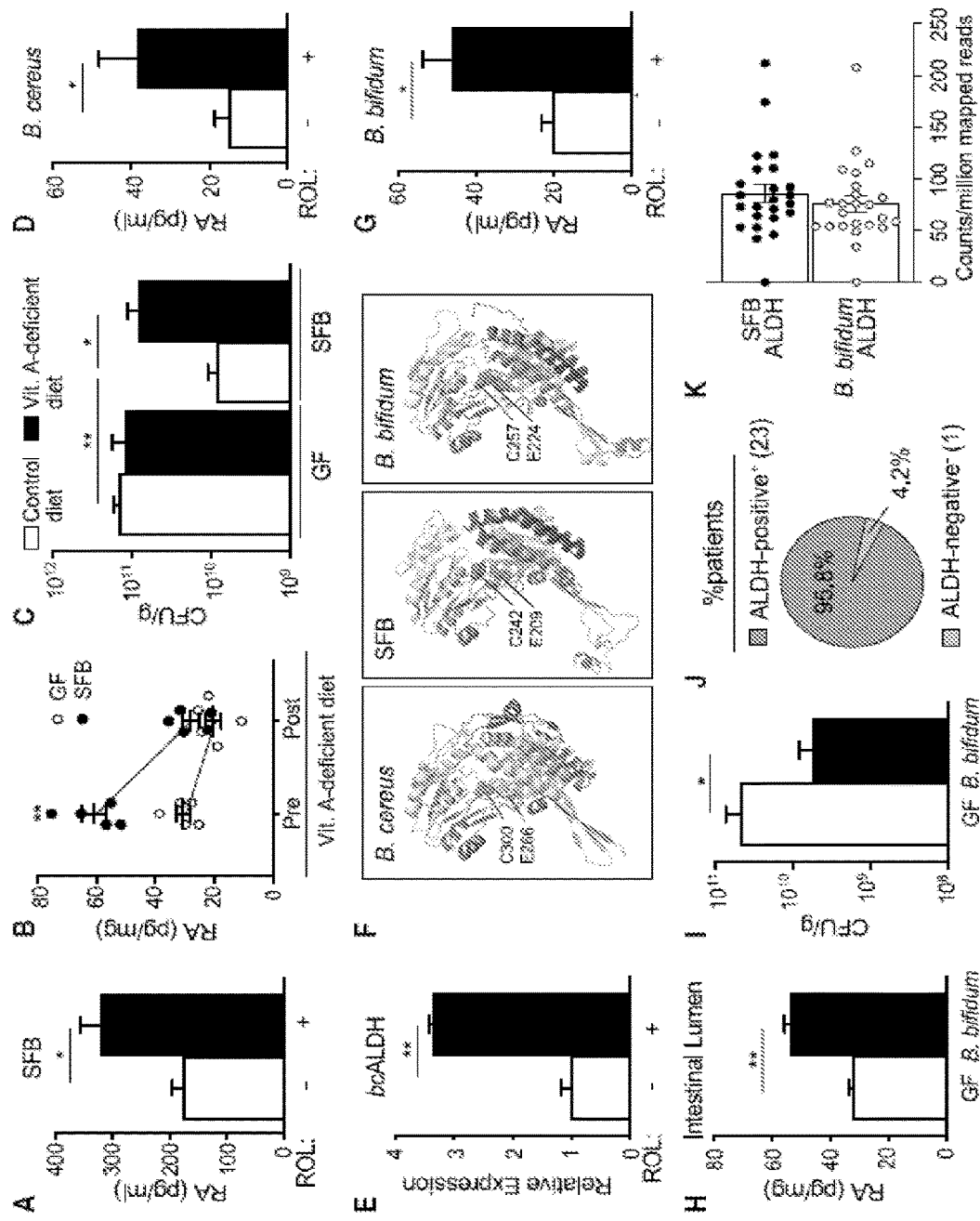
FIG. 5: Commensal bacteria provide a direct source of retinoic acid in the intestine. (A) Retinoic acid concentration in supernatants from intestinal explants from GF and SFB mice incubated with vehicle or all-trans retinol (ROL) (n=3). (B) Retinoic acid levels in intestinal lumen of mice pre and post vitamin A-deficient diet. (C) *C. rodentium* CFUs in stool, normalized to sample weight, day 6 p.i. (n=3) (D) Retinoic acid concentration in media from *B. cereus* cultured with ROL, per $10^8$ CFU of bacteria (n=3). (E) Expression of ALDH by *B. cereus* cultured−/+ ROL (n=3). (F) Protein structure of *B. cereus* ALDH1A1 (KFL74159.1), SFB ALDH (WP_007440235.1) and *B. bifidum* ALDH (WP_015438559.1). Conserved catalytic glutamate [E] and cysteine [C] residues shown as magenta-colored spheres. Root-mean-square deviation of atomic positions (RMSD) compared to bcALDH1A1 for SFB ALDH=2.059 Å; *B. bifidum* ALDH, RMSD=1.514 Å. (G) Retinoic acid concentration following incubation with ROL, per $10^8$ CFU of bacteria (n=3). (H) Retinoic acid concentration in intestinal contents of GF mice monoassociated with *B. bifidum*, normalized to sample weight (n=3). (I) *C. rodentium* CFUs in stool, normalized to sample weight, day 6 p.i. (n=4-5) (J) Percent of patients containing intestinal microbiome reads that align to SFB or *B. bifidum* ALDH. (K) ALDH counts per million reads. Results are mean±SEM. Data represent at least two independent experiments. *p<0.05, **p<0.01.

Commensal bacteria provide a direct source of retinoic acid in the intestine. Intestinal RA levels did not reflect altered mammalian RA synthesis in SFB-colonized mice (FIGS. 4F-4K), suggesting a distinct source of RA. Therefore, to investigate whether SFB directly generates RA by metabolizing vitamin A, explant cultures containing SFB were treated with vitamin A (retinol). Surprisingly, RA levels were significantly increased in supernatants following retinol supplementation of SFB explant cultures (FIG. 5A). To further examine vitamin A metabolism by SFB, RA levels were compared in GF and SFB mice fed vitamin A-deficient diet. Interestingly, removal of vitamin A from the diet decreased intestinal RA levels in SFB mice to the amount observed in GF mice (FIG. 5B). Furthermore, vitamin A-deficiency resulted in elevated *C. rodentium* infection burdens as compared to SFB-colonized mice fed vitamin A-sufficient diet (FIG. 5C), indicating that SFB requires dietary vitamin A to increase luminal RA and protect against *C. rodentium*.

The bacterial strain, *Bacillus cereus*, has been described to express a bacterial aldehyde dehydrogenase enzyme (bcALDH1A1, KFL74159.1) that produces RA from vitamin A in vitro (Hong et al., 2016). Consistent with this work, Applicant found that *B. cereus* produced RA when incubated with retinol (FIG. 5D), without altered growth (FIG. S5A). Furthermore, retinol increased bcALDH1A1 expression by *B. cereus* (FIG. 5E), supporting that this bacterial RA-producing enzyme is sensitive to local retinol levels. Therefore, to investigate whether SFB and potentially other bacterial species express similar aldehyde dehydrogenases that generate RA, Applicant compared protein sequences using bcALDH1A1 as reference. Glutamate-266 and Cysteine-300 are necessary for the catalytic activity of bcALDH1A1 (Hong et al., 2016). Interestingly, SFB, along with the well-known probiotic bacteria *Bifidobacterium bifidum*, encode bacterial ALDH enzymes that share these critical catalytic amino acid residues (FIG. 5F). Furthermore, the predicted protein structures of ALDH enzymes from SFB and *B. bifidum* both exhibited marked overlap with bcALDH1A1 (FIG. 5F).

Similar to SFB and *B. cereus*, *B. bifidum* cultured with retinol increased RA levels without impacting bacterial growth (FIGS. 5G and S5B). Therefore, to test whether *B. bifidum* generates RA in vivo, GF mice were colonized with *B. bifidum* (FIG. S5C) and compared to GF controls. Mice colonized with ALDH-expressing *B. bifidum* demonstrated increased luminal RA relative to GF mice (FIG. 5H) and enhanced protection against *C. rodentium* infection (FIG. 5I). Thus, *B. bifidum* mono-colonized mice exhibited early protection against *C. rodentium*, similar to SFB. These results indicate that a subset of commensal bacterial populations, including SFB and *B. bifidum*, can provide a direct source of RA in the intestine. Given that SFB and *B. bifidum* both convert retinol to RA and express ALDH enzymes, the prevalence of ALDHs in the human intestinal microbiota was evaluated by aligning SFB and *B. bifidum* ALDH genes against microbiome sequencing from healthy human patients (Lewis et al., 2015). Interestingly, these analyses revealed that both genes were detected in nearly all samples analyzed ($^{23}/_{24}$ patients) (FIG. 5J) with an average read count of approximately 80 counts per million reads (FIG. 5K), indicating broad prevalence of homologous genes in the human intestinal microbiota.

Figure 6:
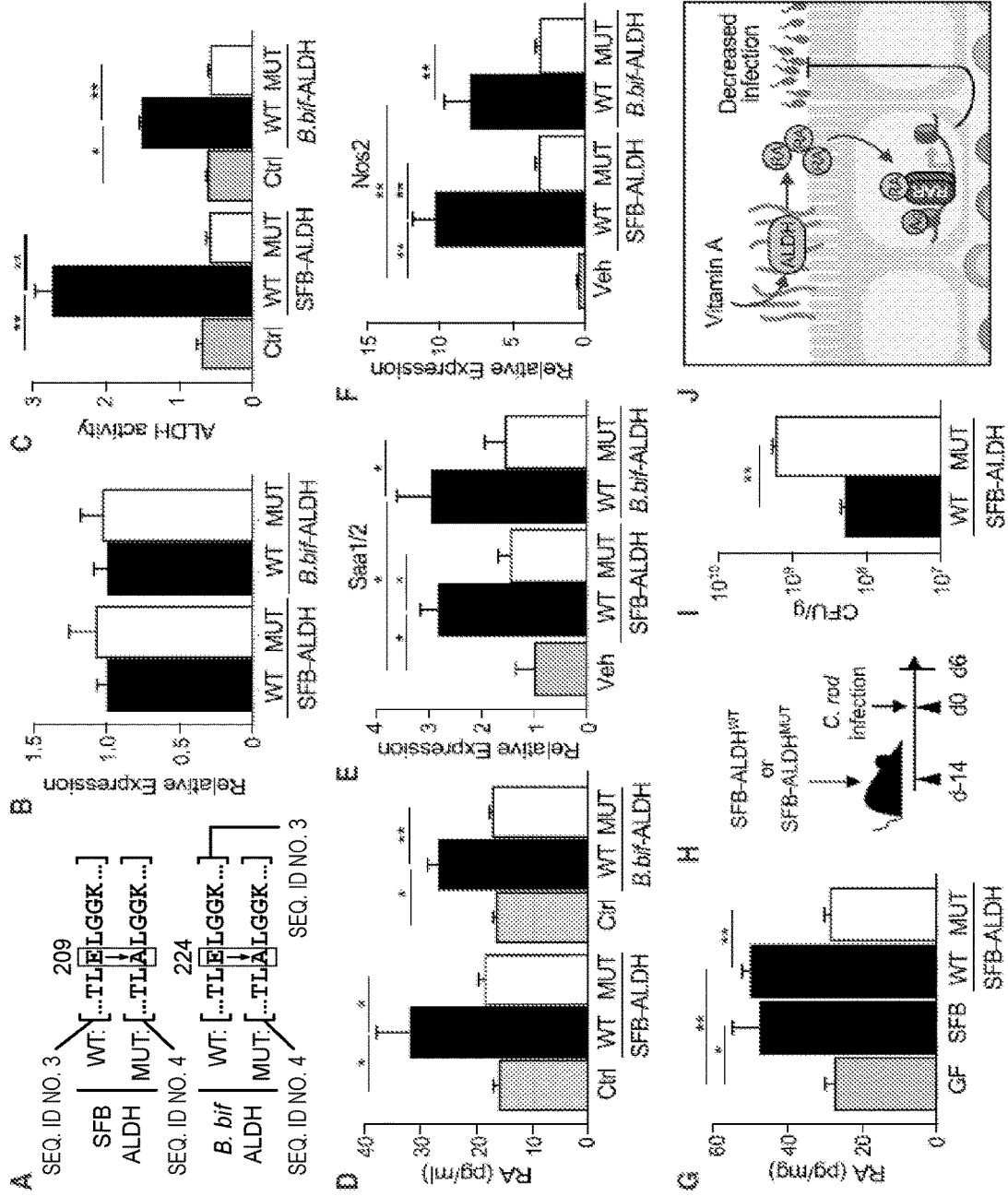
FIG. 6: SFB dehydrogenase activity produces retinoic acid and improves host defense. (A) Protein sequence for wildtype (WT) SFB and *B. bifidum* ALDH demonstrating conserved catalytic glutamate [E] that has been replaced by alanine [A] in the mutant (MUT). SFB and *B. bifidum* ALDH-pET-21a(+) plasmids were expressed in *E. Coli* (ALDH$^{WT}$ or ALDH$^{MUT}$). (B, C) ALDH (B) expression and (C) activity in ALDH$^{WT}$ or ALDH$^{MUT}$ strains (n=3). (D) Retinoic acid concentration of ALDH$^{WT}$ or ALDH$^{MUT}$ cultures incubated with retinol (ROL) (n=3). (E, F) mRNA expression in intestinal organoids stimulated with ALDH$^{WT}$ or ALDH$^{MUT}$ strains for 24 h in 1 μM retinol, normalized to vehicle control (n=3). (G) Retinoic acid concentration in intestinal contents of GF mice monoassociated with SFB, SFB-ALDH$^{WT}$ or SFB-ALDH$^{MUT}$ (n=3), normalized to sample weight. (H) Experimental design. (I) *C. rodentium* CFUs in stool, normalized to sample weight, day 6 p.i. (n=3). (J) Microbiota-derived retinoic acid in the intestine boosts host defense against enteric infection. Results are mean±SEM. Data are representative of at least two independent experiments. *p<0.05, **p<0.01.
Figure 7:
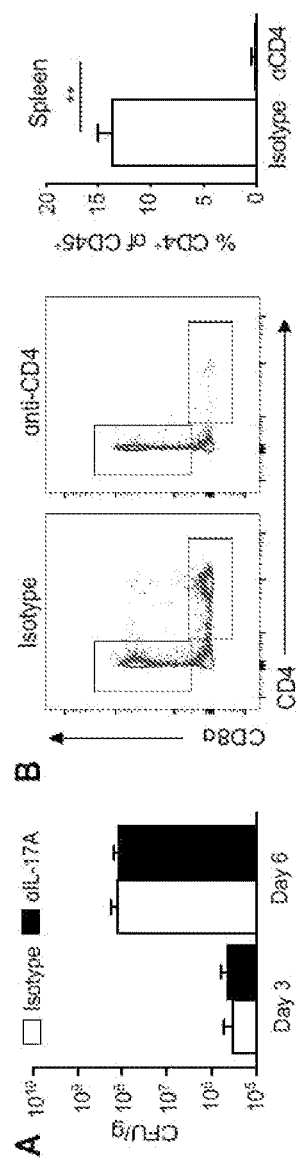
FIG. 7. CD4+ T cell and IL-17 depletion, related to FIG. 1. (A) CFUs of *C. rodentium* in mice treated with anti-IL-17A depleting antibodies, normalized to sample weight (n=4). (B) Representative flow cytometry plots from isotype or anti-CD4 antibody treated mice (n=3). Gated on CD45+ cells. Results are mean±SEM. Data are representative of two independent experiments. **p<0.01.
Figure 8:
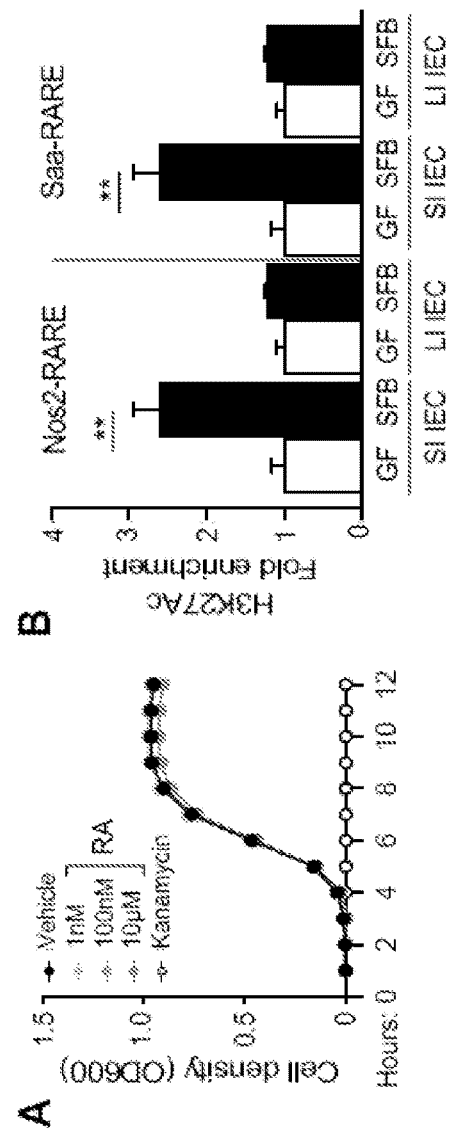
FIG. 8. SFB-sensitive histone acetylation at retinoic acid receptor targets is differentially regulated in small and large intestine IECs, related to FIG. 2. (A) Bacterial cell density measured as the optical density at 600 nm of *C. rodentium* during growth in indicated conditions (n=3). (B) H3K27Ac fold enrichment by ChIP-qPCR, normalized to control site (n=3). Results are mean±SEM. Data are representative of two independent experiments. **p<0.01.
Figure 9:
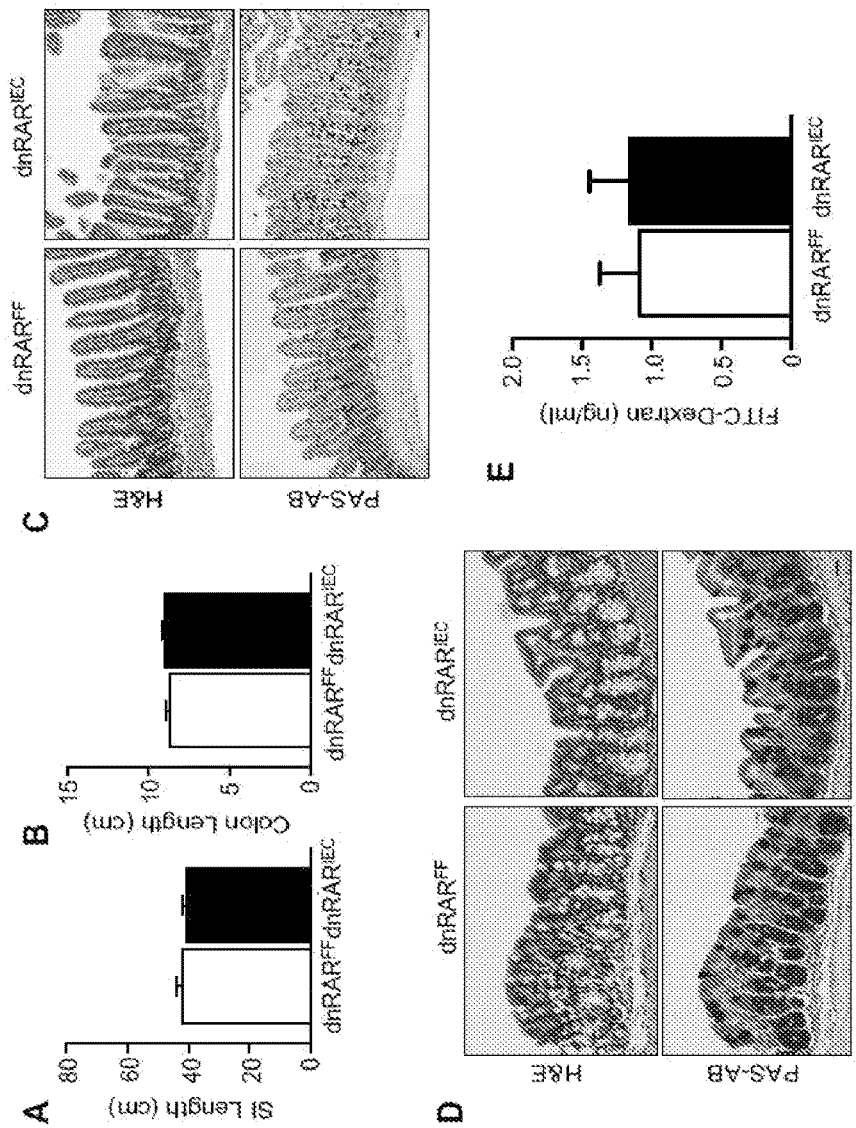
FIG. 9. Epithelial differentiation and permeability are intact in dnRAR$^{IEC}$ mice, related to FIG. 3. (A, B) Total length of (A) small intestine (SI) and (B) colon of dnRARFF and dnRAR$^{IEC}$ mice (n=4). (C, D) Histological staining of (C) ileum and (D) colon. Scale bars: 10 m. (E) FITC in serum of dnRARFF and dnRAR$^{IEC}$ mice following oral gavage with FITC-dextran (n=4). Results are mean±SEM. Data are representative of two independent experiments.
Figure 10:
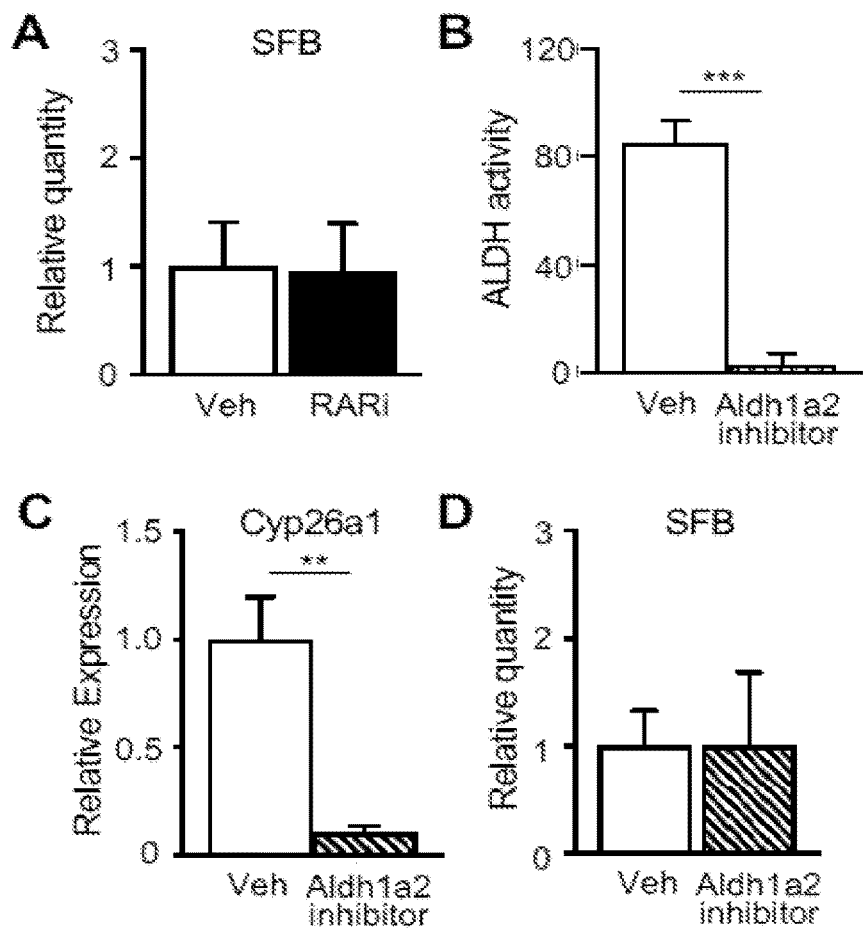
FIG. 10. Inhibition of host RA production does not affect intestinal SFB levels, related to FIG. 4. (A) SFB DNA in feces by qPCR (n=4). (B) ALDH activity in liver of mice treated with WIN18446. (C) Relative mRNA expression in liver. (D) SFB DNA in feces by qPCR. B-D are n=3 per group. Results are mean±SEM. Data are representative of two independent experiments. p<0.01, *p<0.001.
Figure 11:
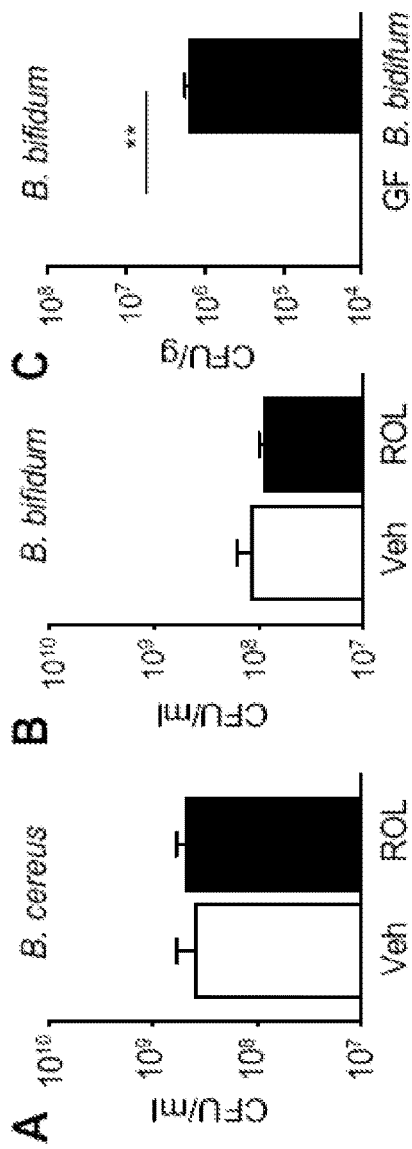
FIG. 11. Bacterial growth in vitro and in vivo, related to FIG. 6. (A, B) CFUs of (A) *B. cereus* or (B) *B. bifidum* grown in vitro (n=3). (C) *B. bifidum* CFUs colonized in GF mice (n=3). Results are mean±SEM. Data are representative of three independent experiments. **p<0.01.
Figure 12:
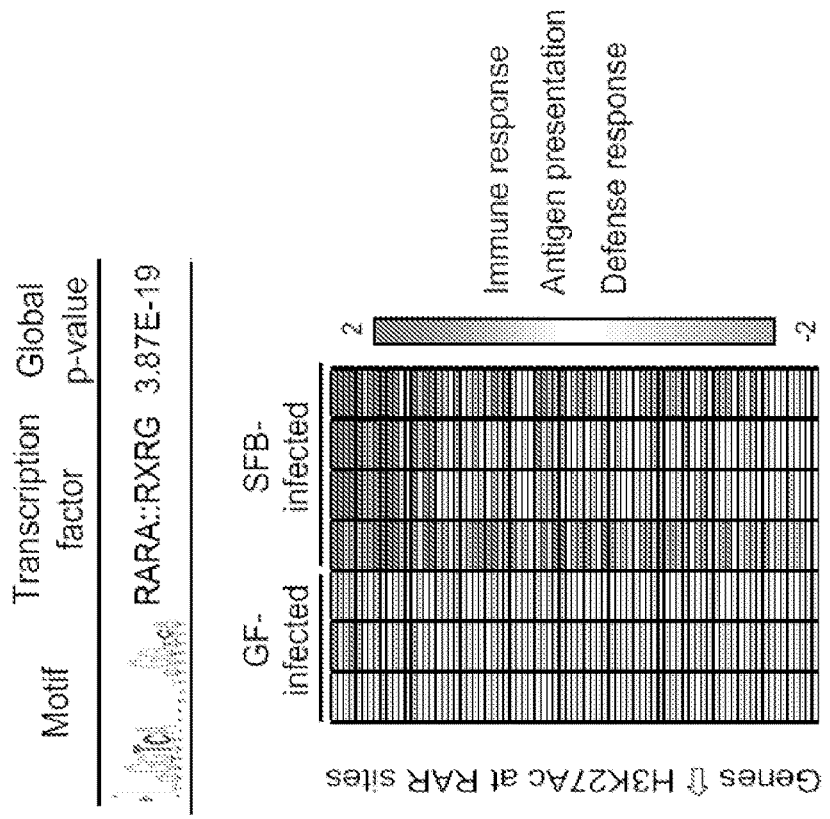
FIG. 12 demonstrates that intestinal epithelium is epigenetically primed by SFB at retinoic acid receptor targets.
Figure 12:
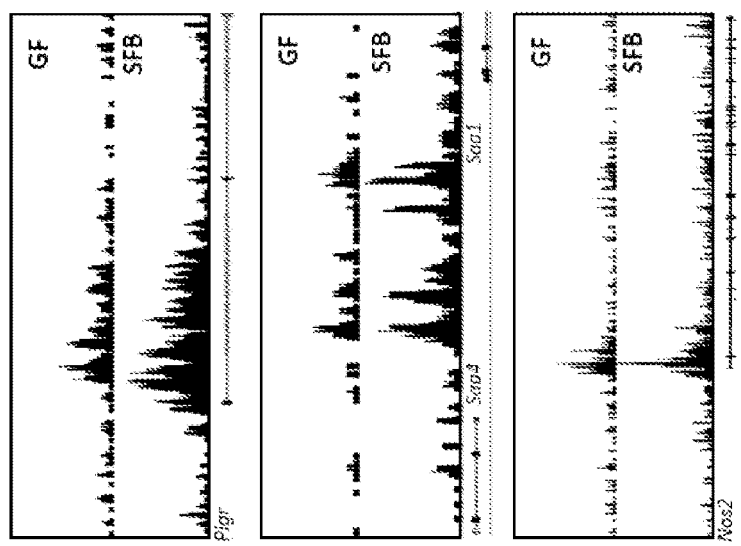
Figure 13:
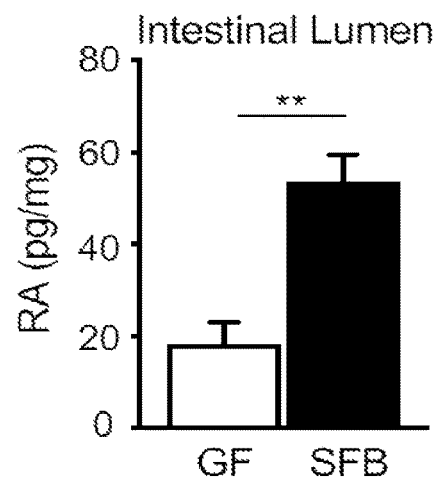
FIG. 13 demonstrates that SFB increases retinoic acid (RA) in the intestinal lumen FIG. 14 demonstrates that probiotic *B. bifidum* increases luminal RA and protects from infection.
Figure 14:
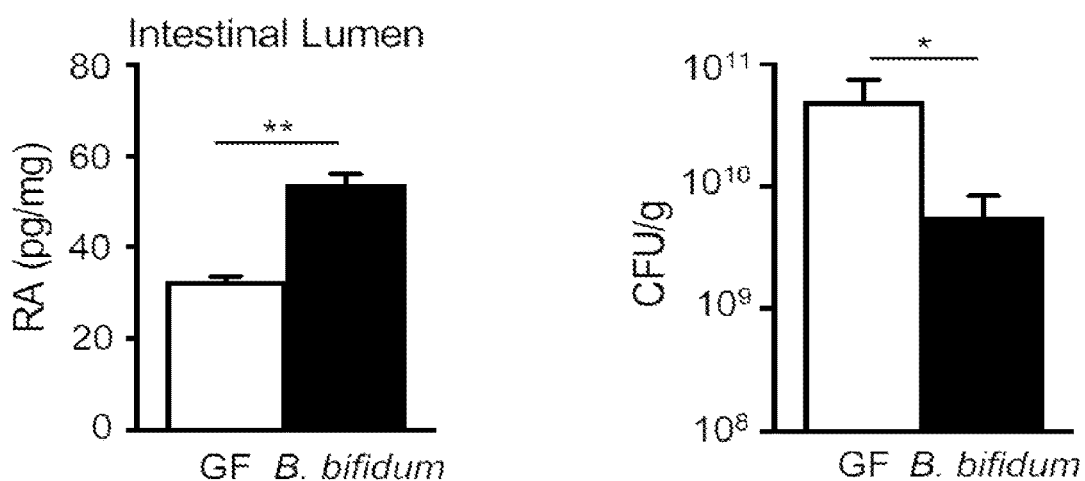
Figure 15:
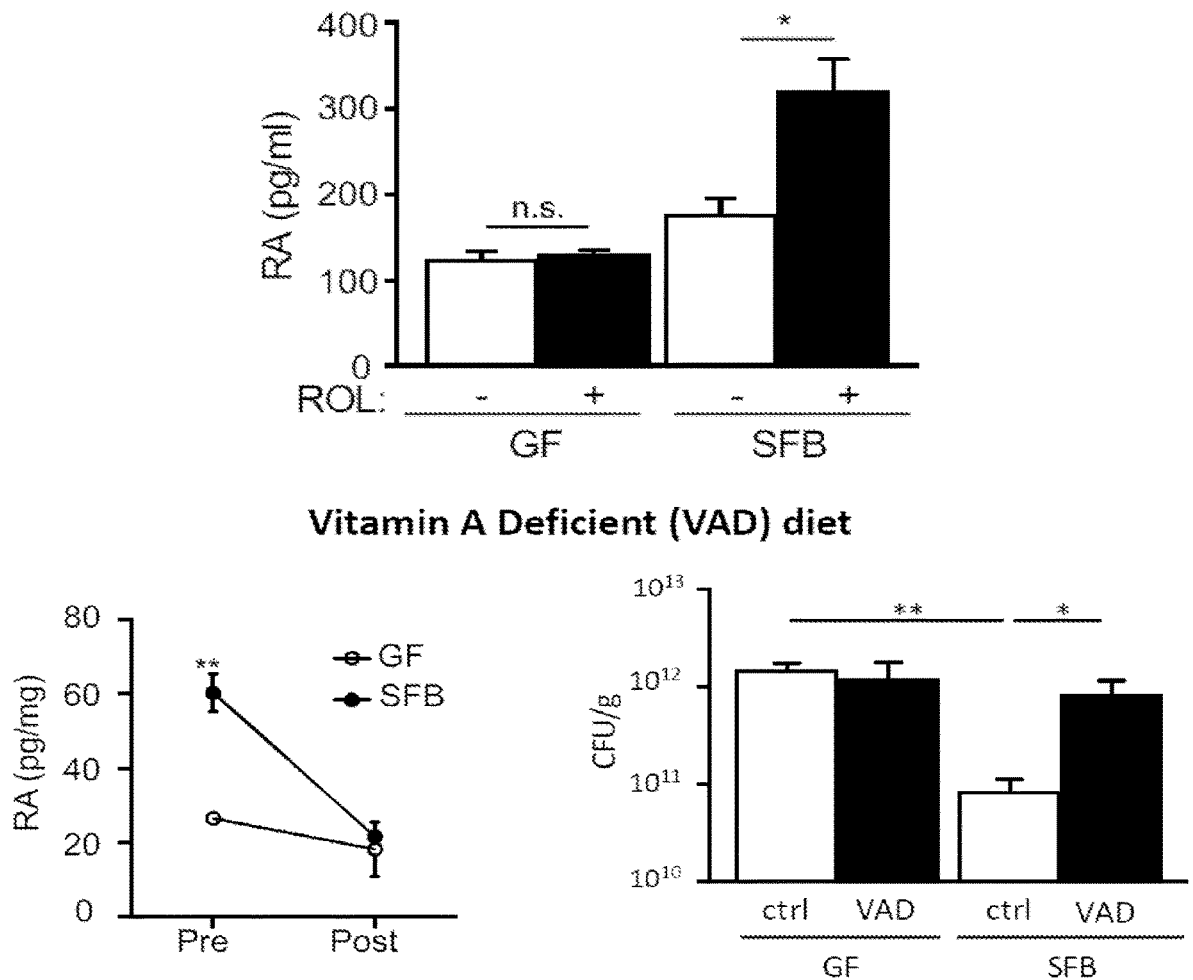
FIG. 15 demonstrates that commensal bacteria break down dietary vitamin A to produce retinoic acid.
Figure 16:
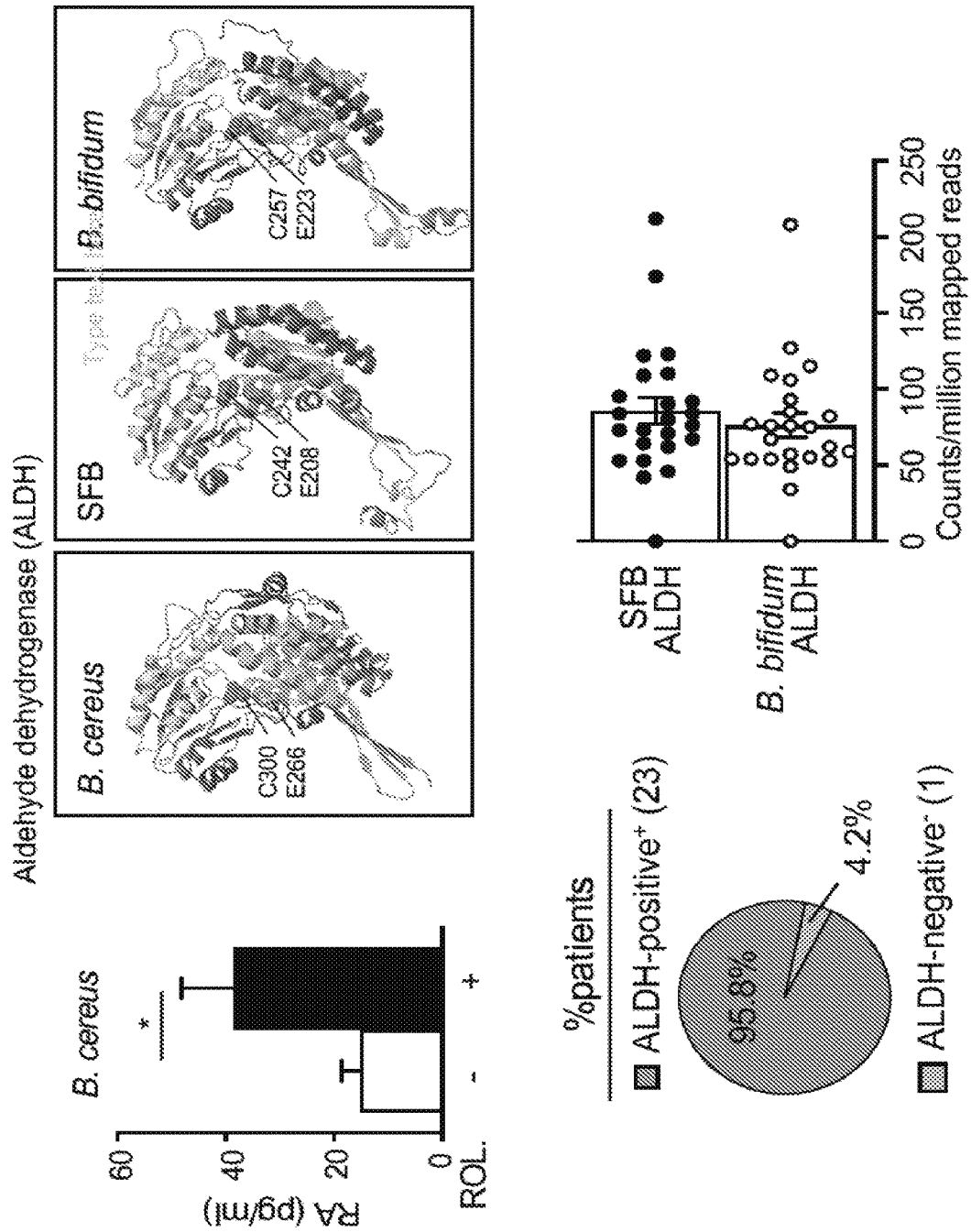
FIG. 16 demonstrates that commensal bacterial in humans express an Aldh gene that can produce retinoic acid.
Figure 17:
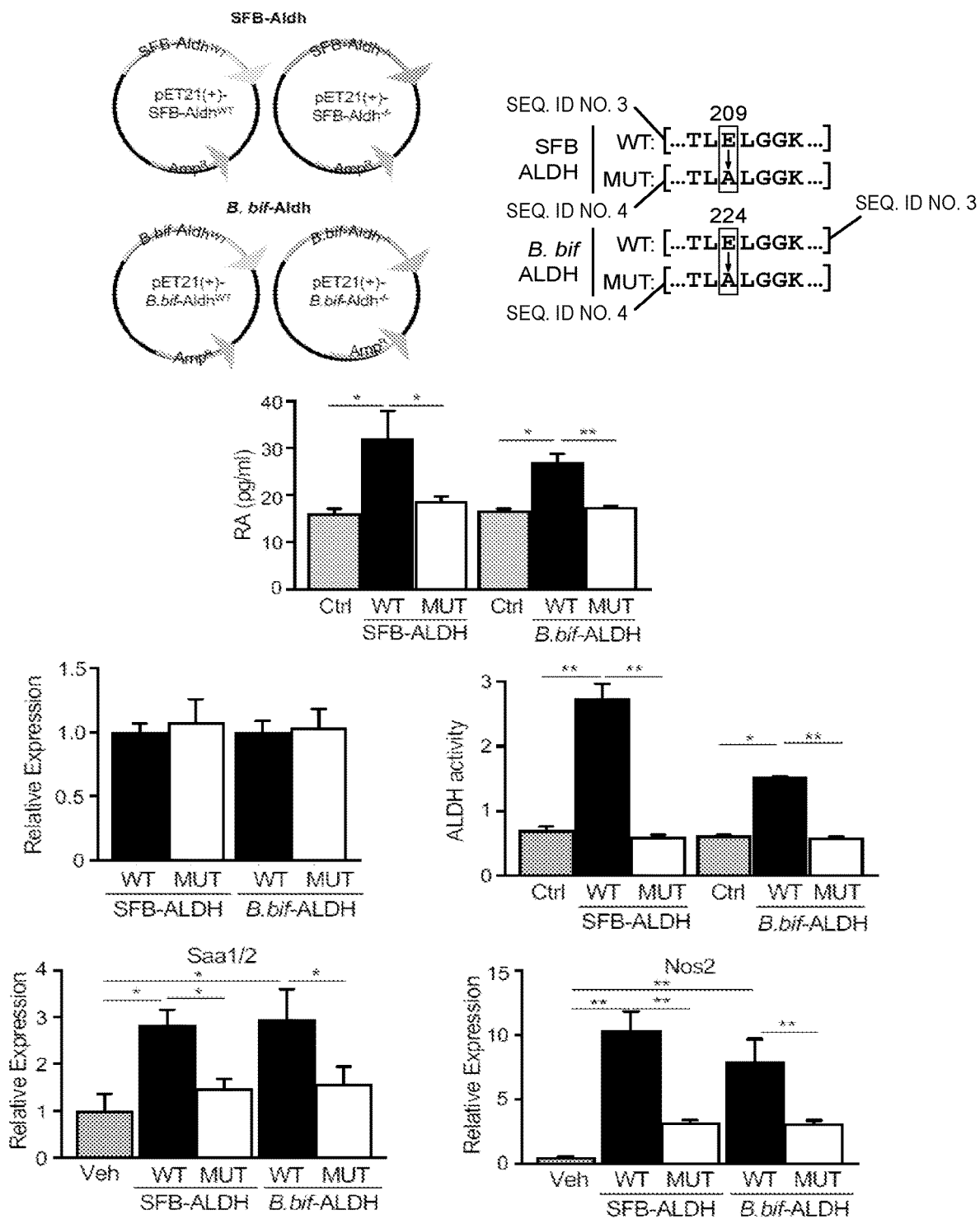
FIG. 17. Depicts bacteria that have been engineered to express the Aldh gene from SFB or *B. bifidum* (versus an inactive Aldh form) that can be administered to mice and the effect on host defense.
Figure 18:
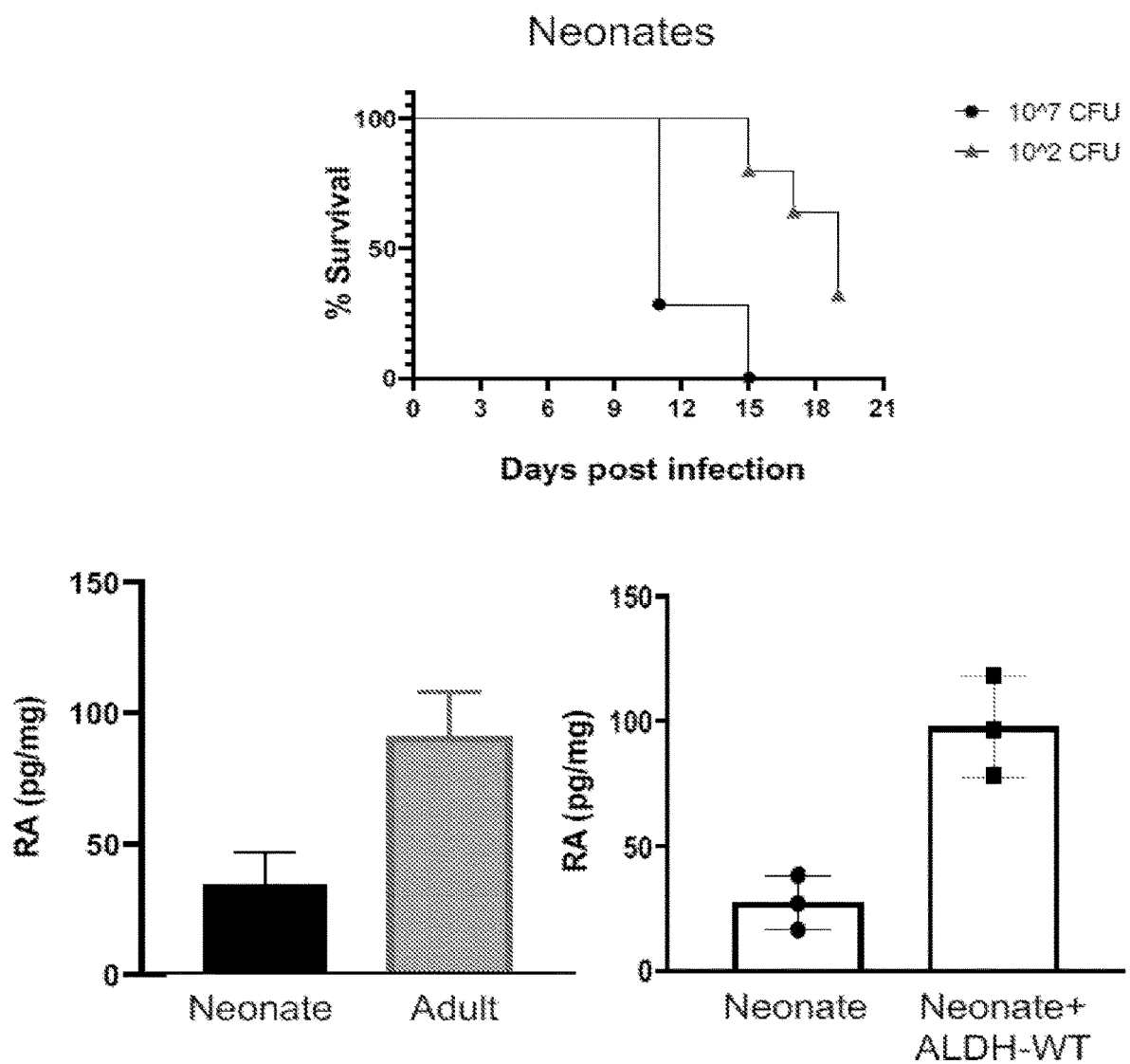
FIG. 18 demonstrates that administration of bacteria engineered to express RA protects can be administered to neonates to increase retinoic acid and protect against infection.
Figure 19:
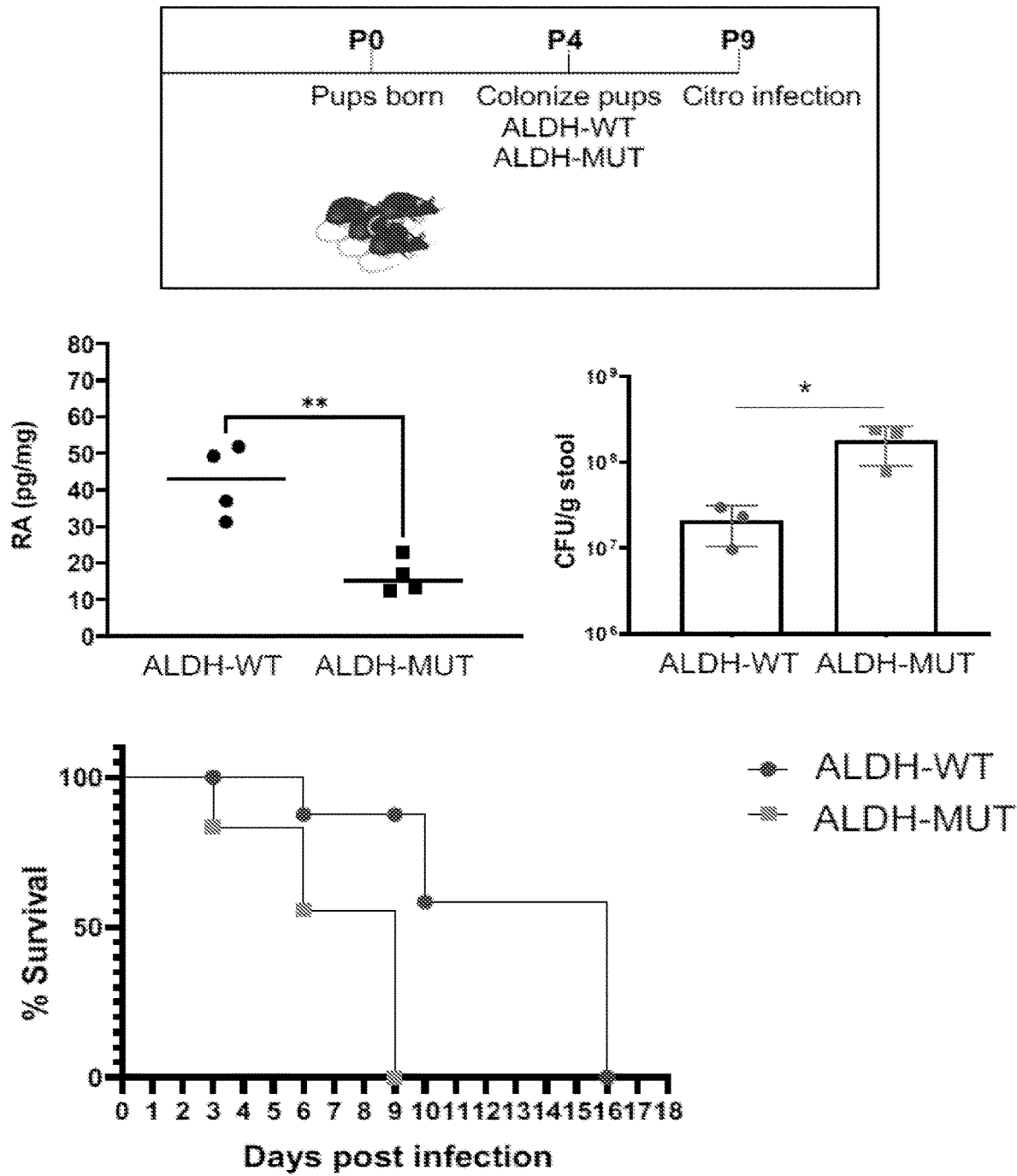
FIG. 19 demonstrates that administration of bacteria engineered to express RA decreases infection and improves survival in neonates.
Figure 20:
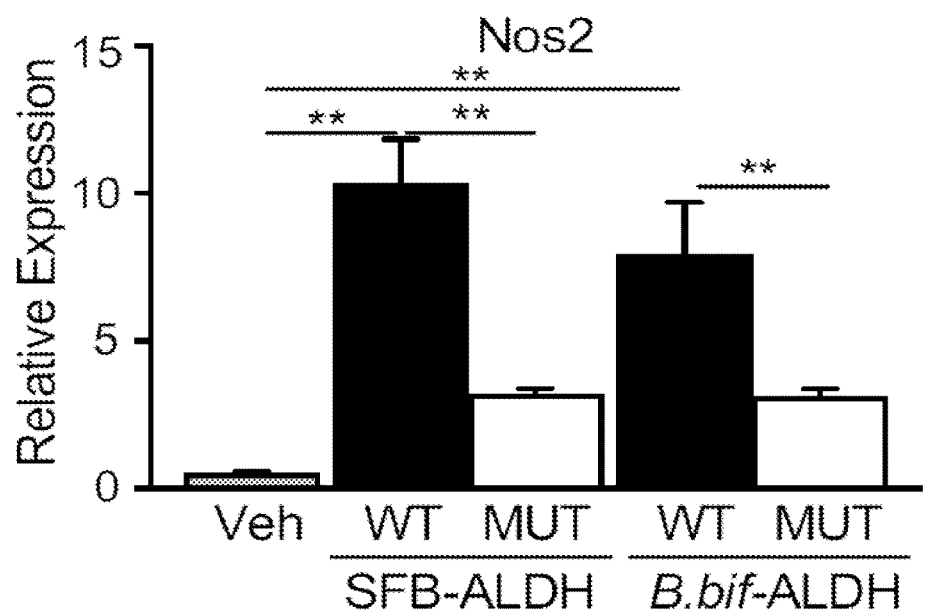
FIG. 20 demonstrates that bacteria engineered to express RA increases protective innate pathways in the intestine.
Figure 21:
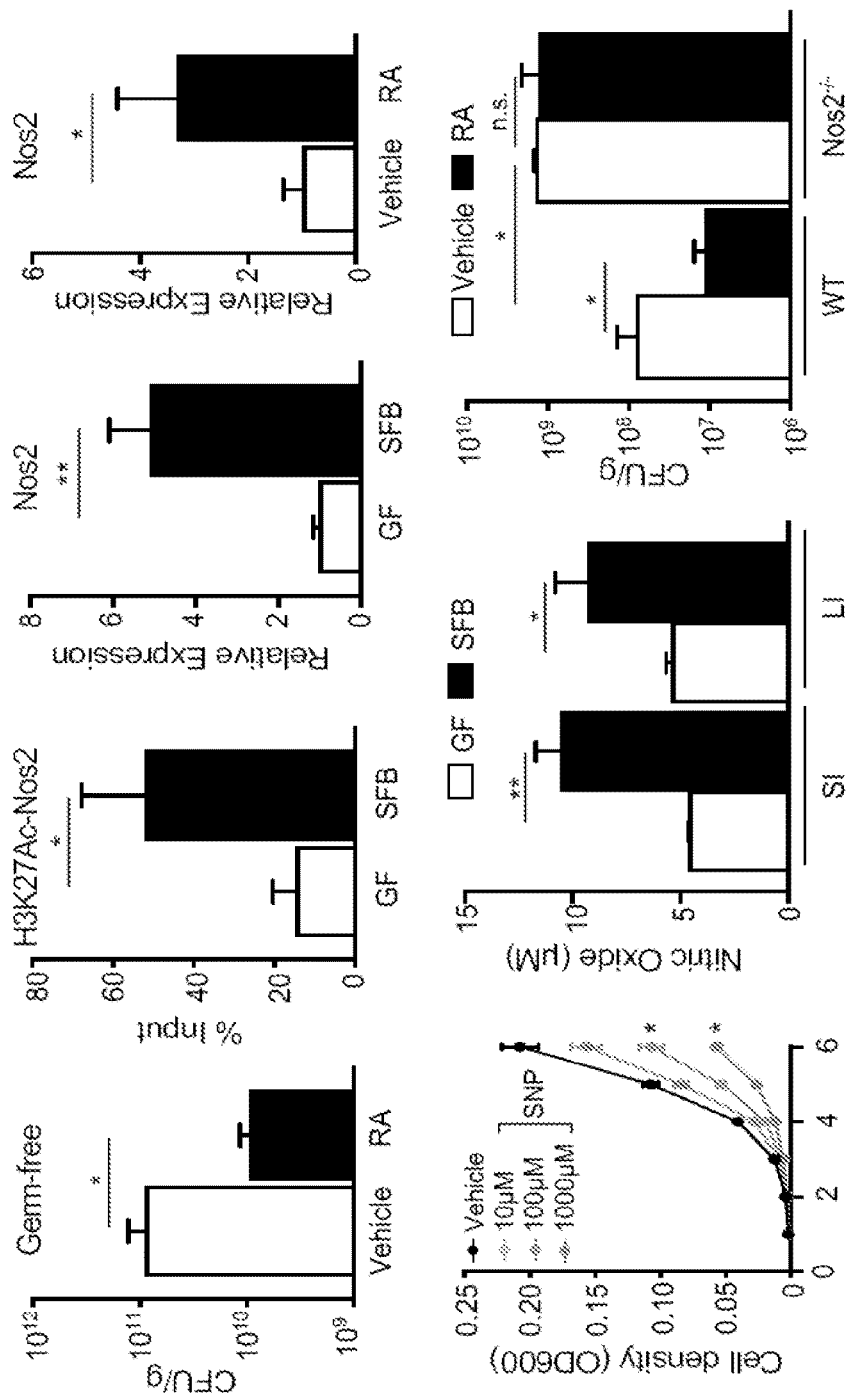
FIG. 21 demonstrates that retinoic acid improves defense in part through Nos2 regulation.
Figure 22:
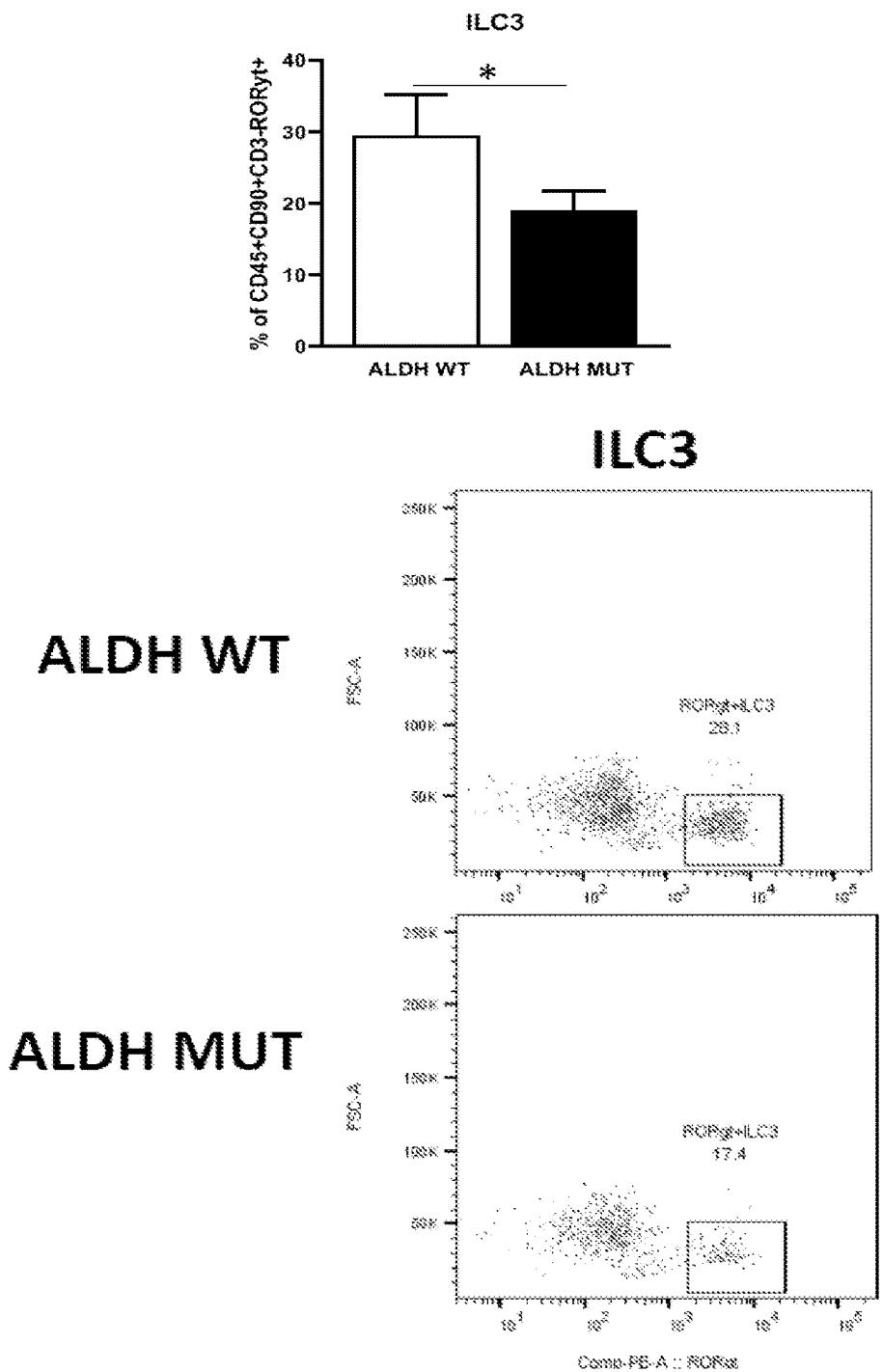
FIG. 22 demonstrates that administration of bacteria engineered to express RA also increases protective immune cells and decreases pro-inflammatory cells FIG. 23 demonstrates that giving bacteria engineered to express RA also increases protective immune cells and decreases pro-inflammatory cells as measured in the mesenteric lymph node.
Figure 23:
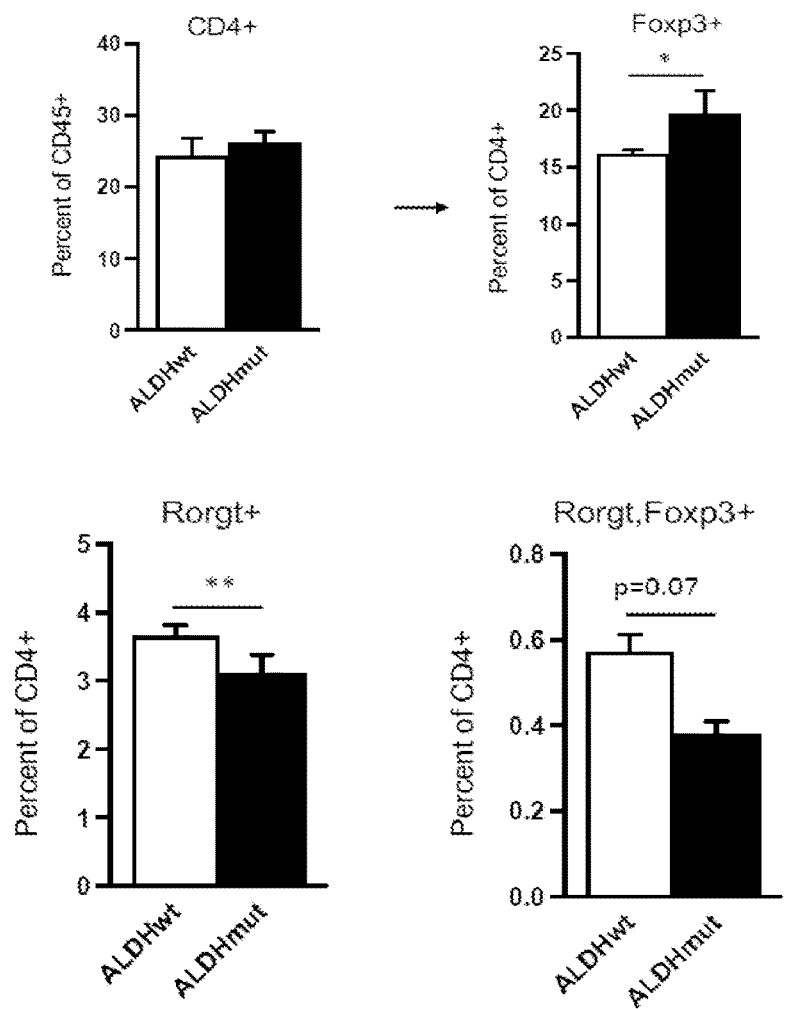
Figure 24:
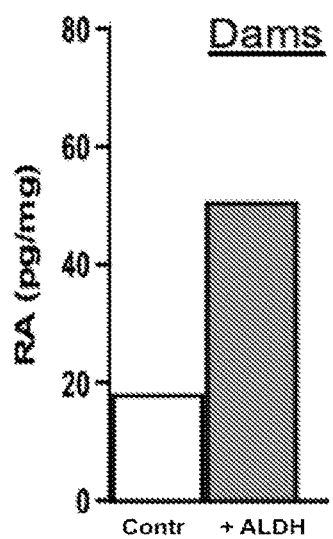
FIG. 24 demonstrates that administration of bacteria engineered to express SFB aldehyde dehydrogenase to pregnant mice increases retinoic acid.
Figure 25:
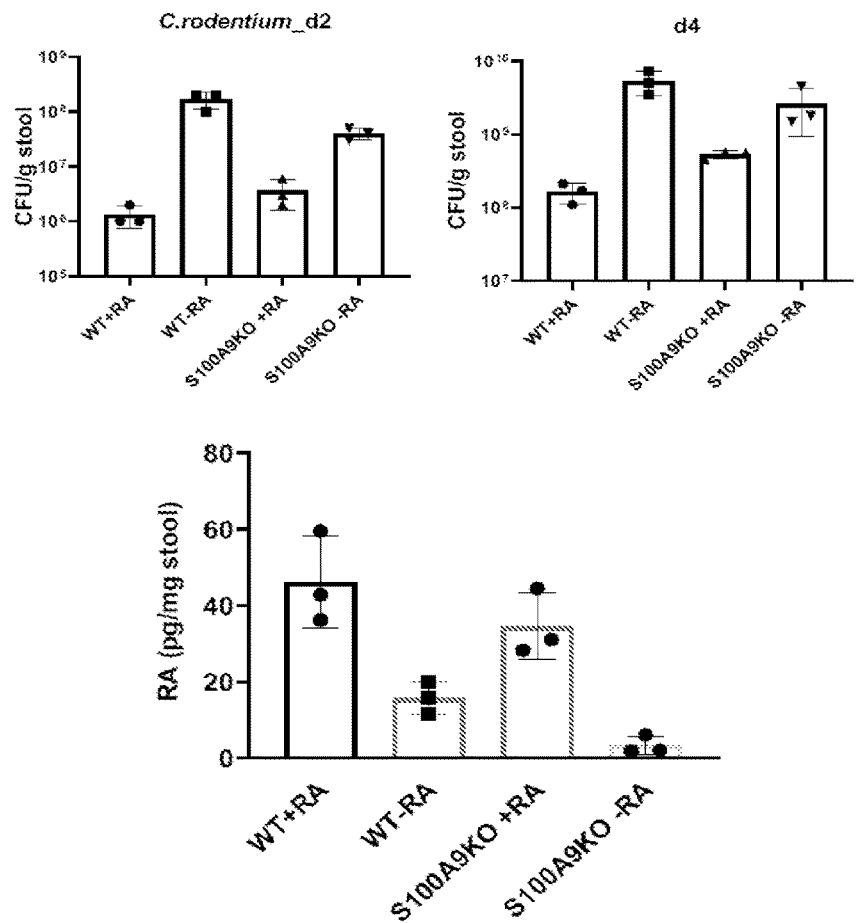
FIG. 25 shows that administering RA-producing bacteria decreases infection in genetically susceptible mice.
Figure 26:
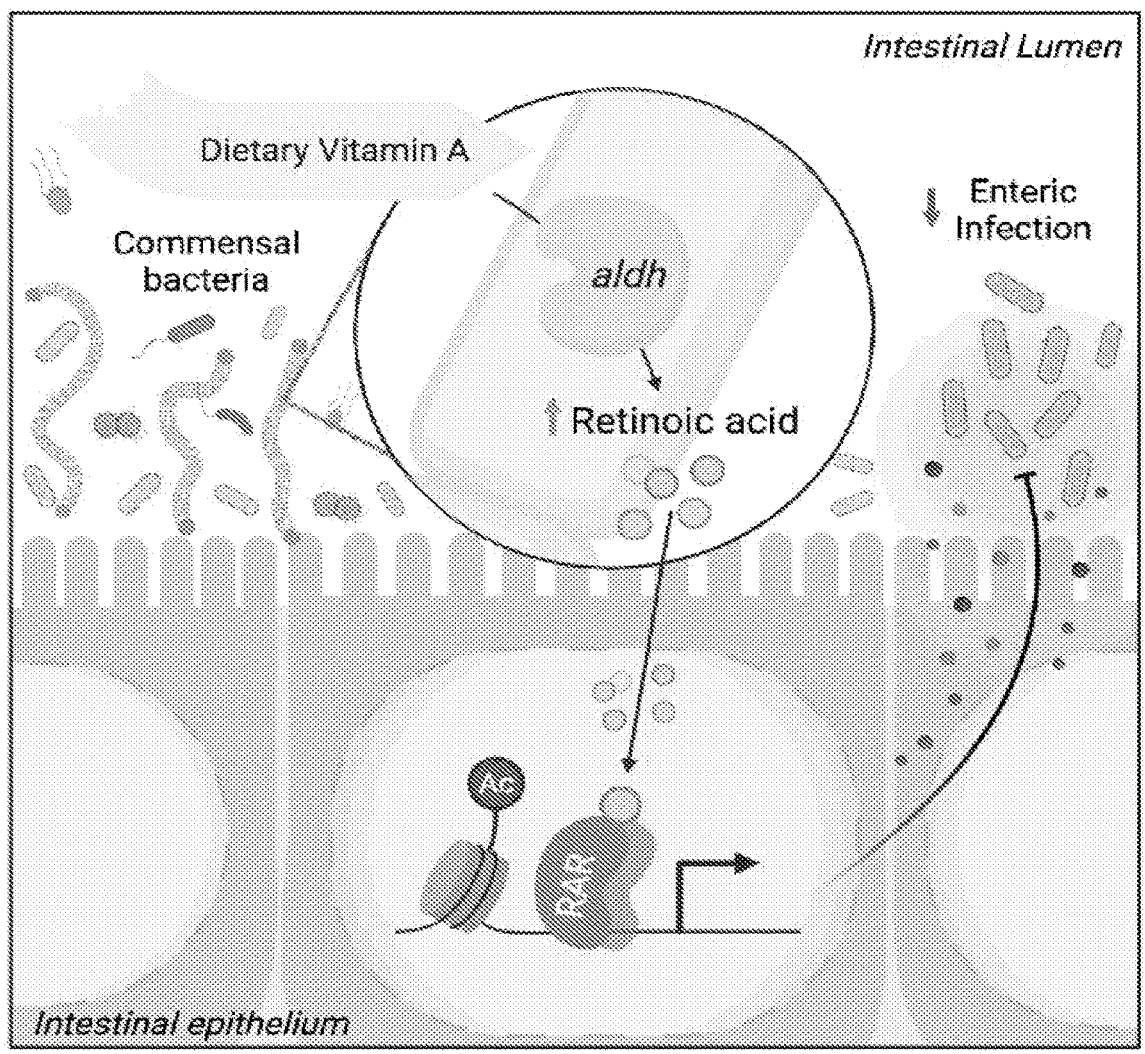
FIG. 26 is a schematic depicting administration of bacterial engineered to express retinoic acid to neonatal and adult mice improves innate immunity and decreases infection. Bacterial (SFB or *B. bifidum*) aldehyde dehydrogenase enzyme can be administered to increase retinoic acid in the intestine, improve innate immunity and decrease infection.
Figure 27:
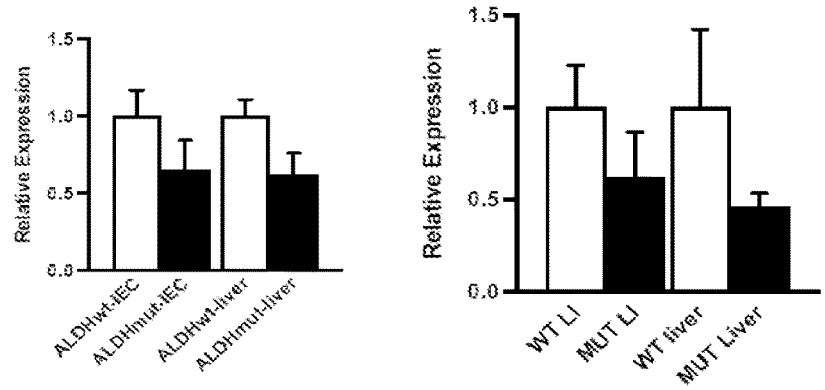
FIG. 27 demonstrates that mammalian immune and metabolic genes in the liver and intestine are sensitive to administration of bacteria engineered to express RA.
Figure 27:
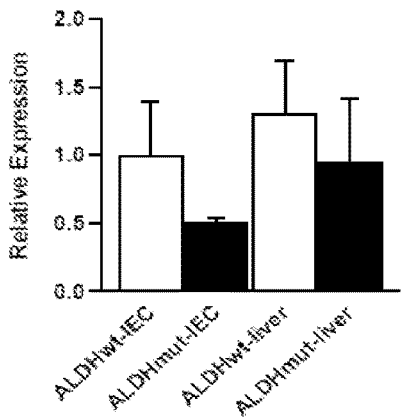
Figure 27:
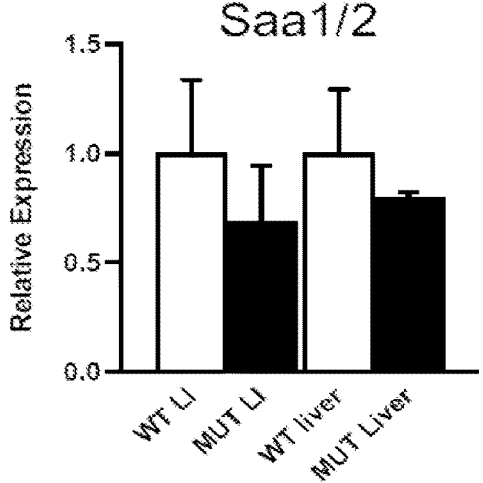

SFB dehydrogenase activity produces retinoic acid and improves host defense. While direct genetic manipulation in SFB or *B. bifidum* would be ideal to test the functional role of the microbial ALDH gene, this approach is technically limiting in both species. Therefore, to directly examine the contribution of bacterial ALDH enzymes in producing RA, ALDHs from SFB or *B. bifidum* were expressed in *E. coli* as the wild-type enzyme ($ALDH^{WT}$) or a catalytic domain mutant variant ($ALDH^{MUT}$) (FIG. 6A). $ALDH^{WT}$ and $ALDH^{MUT}$ enzymes were similarly expressed for both strains (FIG. 6B). Importantly, $ALDH^{WT}$ strains exhibit significant ALDH activity whereas $ALDH^{MUT}$ strains showed no enzymatic activity (FIG. 6C). When cultured with vitamin A, both SFB-$ALDH^{WT}$ and B. bif-$ALDH^{WT}$ strains produced elevated RA relative to non-ALDH expressing control (FIG. 6D). Importantly, this RA induction with $ALDH^{WT}$ bacteria was lost in $ALDH^{MUT}$ strains (FIG. 6D), demonstrating that RA levels are indeed dependent on the bacterial enzyme. In addition, intestinal organoid cultures containing retinol exposed to $ALDH^{WT}$ bacteria exhibited increased Saa1/2 (FIG. 6E) and Nos2 (FIG. 6F) expression relative to organoids incubated with $ALDH^{MUT}$ bacteria, demonstrating that microbial ALDH activity increases expression of RA-sensitive targets in mammalian epithelium.

To next test whether bacterial ALDH enzymes generate RA in vivo, GF mice were colonized with SFB-ALDH expressing strains. Interestingly, colonization of GF mice with the SFB-$ALDH^{WT}$ strain increased intestinal RA levels relative to GF mice, whereas RA levels in $ALDH^{MUT}$-colonized mice remained relatively unchanged (FIG. 6G). Furthermore, following *C. rodentium* infection, GF mice colonized with $ALDH^{WT}$ also exhibited lower pathogen levels relative to infected mice colonized with ALDH-inactive bacteria (FIGS. 6H and 6I). Collectively, these new data demonstrate a direct contribution of bacterial ALDH enzymes in the production of RA in the intestine, and that this microbial enzymatic activity enables improved pathogen control.

Discussion

In this study, Applicant discovered that SFB and other beneficial commensal bacteria generate RA in the intestine and regulate epithelial RAR signaling to enhance defense against a pathogen (FIG. 6J). RA is a fat-soluble metabolite derived from carotenes and vitamin A that is known for its immunomodulatory effects and role during infectious disease (Hall et al., 2011a). Vitamin A deficiency in humans is linked to increased susceptibility to numerous bacterial and viral pathogenic infections (Sommer, 2008; World Health Organization, 2009), whereas vitamin A supplementation reduces incidence and mortality of diarrheal diseases commonly caused by intestinal pathogens (Green and Mellanby, 1928; Huang et al., 2018; Semba, 1999). Although vitamin A has been used as a clinical health intervention for diarrheal disease and other health conditions, the reported outcomes have been inconsistent (Dibley et al., 1996; Long et al., 2007). This variability has been attributed to range of factors such as varying degrees of baseline vitamin A deficiencies and differences in vitamin A dosing strategies (Dibley et al., 1996; Long et al., 2007). In mice, vitamin A availability alters the severity of infection and regulates repair of infection-induced epithelial damage (McDaniel et al., 2015; Mielke et al., 2013; Snyder et al. 2019).

IECs in the small intestine express both RA-generating enzymes and RARs that are activated by RA, thereby playing a central role in vitamin A-dependent regulation. Our transcriptional analyses showed that induction of RAR targets during infection was higher with SFB-colonization and indicated RAR targets are enriched in host defense pathways. Consistent with this, recent studies have discovered that IEC-intrinsic RAR expression promotes defense by regulating antimicrobial peptide production (Gattu et al., 2019; Jijon et al., 2018). A potential increase in goblet cells has been described in the intestine of dnRAR$^{IEC}$ mice (Iyer et al., 2020). While Applicant did not observe significant differences in goblet cells, an increase in goblet cells would be expected to limit *C. rodentium* infection (Bhinder et al., 2014), as opposed to the elevated burden that occurs in dnRAR$^{IEC}$ mice. Furthermore, the ability of IECs to sense RA is necessary for defense against *Salmonella Typhimurium* (Gattu et al., 2019; Iyer et al., 2020). Using a transgenic mouse model where IECs are unable to respond to RA, Applicant observed that IEC-intrinsic activation of RAR by RA is necessary for defense against *C. rodentium*. Specifically, RA administration significantly lowered pathogen burdens in control mice compared to mice lacking the ability to activate RAR in IECs. Although Applicant did not observe significant early protection against *C. rodentium* from RA-administration in mice with defective RAR specifically in IECs, RA also likely activates mucosal immune cells, consistent with studies showing dendritic cells, macrophages and innate-lymphoid cells also respond to RA during infection (Erkelens and Mebius, 2017; Gundra et al., 2017; Kim et al., 2015; Zeng et al., 2016). Additionally, while our studies indicate Nos2 as one downstream target in IECs that mediates RA-induced protection against *C. rodentium*, Applicant cannot exclude that other factors, such as ILCs or IL-22, also contribute.

SFB-dependent defense initially occurred independently from CD4$^+$ T cells, however, both SFB and RA are known to regulate development and function of adaptive immune cells, particularly Th17 cells which promote *C. rodentium* clearance (Symonds et al., 2009). Th17 cell regulation by RA appears to be largely context and dose dependent. RA supplementation at pharmacological levels has been shown to suppress Th17 differentiation and promote regulatory T cells (Benson et al., 2007; Mucida et al., 2007). In contrast, others have found that physiological concentrations of RA stimulation instead promote Th17 skewing of CD4$^+$ T cells both in vitro and in vivo (Takahashi et al., 2012; Uematsu et al., 2008; Wang et al., 2010). Consistent with this evidence, RARα-deficient T cells are also unable to differentiate into Th17 cells in vitro under Th17-polarizing conditions (Hall et al., 201 Tb). Importantly, mice fed vitamin-A deficient diet are deficient in Th17 cells, further indicating that RA is required for in vivo development and/or maintenance of these cells (Cha et al., 2010; Wang et al., 2010). The presence of SFB in the intestinal microbiota of mice was shown to drive Th17 cell expansion by inducing epithelial expression of Serum Amyloid A (SAA) proteins (Ivanov et al., 2009; Sano et al., 2015). Intestinal SAA expression requires dietary vitamin A and is directly regulated by epithelial RARs (Gattu et al., 2019).

These findings, in combination with our current work, support a model in which increased RA levels and enhanced epithelial RAR activation by SFB promotes innate epithelial defense, and simultaneously drives Th17 cell differentiation, potentially through RA-dependent transcriptional regulation of SAAs. Considering that SFB directly interacts with IECs and even undergoes vesicle-mediated communication (Ladinsky et al., 2019), it is believed that SFB may provide a local dose of RA that transcriptionally primes host epithelial cells. Interestingly, SFB does not induce similar H3K27Ac levels within the Saa1/2 and Nos2 genes of colonic IECs, suggesting tissue site specificity. SFB colonizes the terminal ileum, however *C. rodentium* infects the colon. While Applicant cannot exclude that a subset of epigenetic changes will overlap at distinct locations, it is unlikely to be identical given the localization of SFB to the ileum. The spatial separation of SFB and *C. rodentium* colonization implies that SFB does not directly block the pathogen niche. Our mechanistic analyses identified Nos2 as an epigenetically modified SFB-sensitive RAR target in the ileum that is necessary for RA-induced protection against *C. rodentium*. Interestingly Applicant found that NO, the antimicrobial metabolite generated by Nos2, was increased in both ileum and colonic contents from SFB-colonized mice relative to GF mice. Thus, it is suspected that NO production through microbiota-dependent regulation of Nos2 and NO may affect the pathogen as it travels in the ileum or during colonic colonization.

Despite the abundance of evidence linking host immunity and RA, relatively little is known about how the microbiota regulates RA. It was recently shown that intestinal tissue RA levels were lower in conventionally-housed mice compared to GF mice due to decreased expression of Rdh7, an enzyme that oxidizes retinol to retinal (Grizotte-Lake et al., 2018). This downregulation was found to be driven primarily by Clostridial species. Furthermore, expansion of Proteobacteria following antibiotic depletion of Clostridia correlated with induction of host Rdh7 expression, suggesting that distinct commensal bacterial species may differentially regulate RA. Our data describe a mechanism in which epithelial expression of RA-sensitive factors in mice monocolonized with SFB, or intestinal organoids exposed to SFB, is largely bacterial-dependent. SFB induced RA-target genes Saa1/2 expression in organoids despite inhibition of mammalian Aldh1a2. Further, bacterial ALDH was necessary to produce RA, and mutation of this enzyme inhibited RA production. Taken together, these findings indicate a role for bacterial-derived RA in epithelial regulation. Thus, in addition to mammalian-produced RA, SFB also contributes RA in the intestinal environment and microbial generated RA is relevant to regulation of IECs and *C. rodentium*. However, the magnitude of induction in vitro was not as large as that observed in vivo, which supports that other factors not present in culture, such as IL-22, can also contribute to activation of RA-sensitive pathways in the host. Given this regulation, commensal bacterial species may differentially modulate intestinal RA levels through microbe intrinsic mechanisms and/or distinct host-dependent pathways.

Investigation of vitamin A metabolism has largely focused on mammalian enzymes, as RA production has generally been considered a mammal-specific reaction (Biesalski et al., 2007). Whether bacteria directly contribute to vitamin A metabolism has been largely unexplored. Prior studies demonstrated that *E. coli* were capable of generating retinal and retinyl acetate, and potentially retinoic acid, in culture (Jang et al., 2011, 2015). Genetic manipulation of putative endogenous genes in *E. coli* involved in converting retinol to retinal (ybbo) and RA (puuC, eutC) altered retinoid production by *E. coli* (Jang et al., 2011, 2015). Furthermore, a bacterial ALDH expressed in *B. cereus*, a gram-positive bacterium commonly found in the gastrointestinal tract of mammals, was able to directly convert retinal to RA in vitro (Hong et al., 2016). Applicant demonstrates that commensal SFB and *B. bifidum* express ALDH proteins that produce RA in vitro and in vivo, and that mammalian intestinal epithelial regulation is sensitive to the catalytic activity of these bacterial enzymes. In addition, dietary vitamin A and enzymatically active bacterial ALDH are required for SFB to increase luminal RA concentrations and protect against *C. rodentium*. Together, these findings indicate that bacteria inherently harbor retinoid metabolism pathways and revealed important dietary implications for bacterial metabolism of vitamin A in host defense.

In addition to the protective effects of bacterial RA on the host, we anticipate that there are likely bacterial-intrinsic benefits to metabolizing vitamin A. While Applicant did not observe obvious differences in cultured bacterial growth with short-term vitamin A exposure, it is possible that metabolizing vitamin A entails a competitive advantage in the intestine. Vitamin A availability affects cellular zinc absorption, and vice versa (Christian and West, 1998; Rahman et al., 2002; Smith, 1980). Zinc is an essential micronutrient for all organisms including bacteria and is required for normal cellular physiology. However, excess zinc is toxic to bacteria and thus must be tightly controlled (Hantke, 2005; McDevitt et al., 2011). Zinc is most abundant in the intestine, so it is plausible that bacterial metabolism of retinoids improves absorption of zinc to maintain non-bactericidal levels in the intestinal environment. Alternatively, oxidation of vitamin A to retinol may provide bacteria with important reducing equivalents in the form of NADH and NADPH that are needed for energy metabolism (Spaans et al., 2015; Sporer et al., 2017).

Mice

Germ-free (GF) C57BL/6 mice were maintained in sterile isolators (Class Biologically Clean) or sealed positive pressure IVC racks (Allentown) in the CCHMC Gnotobiotic Mouse Facility. For mono-association studies, GF mice were colonized with singular commensal species suspended in sterile PBS via oral gavage (Bifidobacterium bifidum ATCC 29521) or by pre-colonized bedding (SFB). For SFB ALDH-expressing strains, GF mice were orally gavaged with a single dose of $10^9$ CFU SFB-ALDH$^{WT}$ or SFB-ALDH$^{MUT}$ strains and maintained on water containing ampicillin (1 g/L) and isopropylthio-β-galactoside (IPTG, 1 mM) refreshed every 7 days. All GF and monoassociated mice were fed autoclaved food and water, and routinely monitored to ensure the absence of microbial contamination and/or assess level of colonization. C57BL/6 floxed dnRAR (Rajaii et al., 2008) mice were crossed to villin-Cre-recombinase expressing mice (Madison et al., 2002) to generate dnRARmc mice. For all experiments, mice were used at 8-16 weeks old, age- and sex-matched and paired with littermates when possible. Animals were housed in ventilated cages up to 4 per cage in 12 hr light/dark cycles with unrestricted access to food and water. Nos2−/− mice (Laubach et al., 1995) were bred on site. For FITC-dextran intestinal permeability studies, mice were fasted for 4 hr and gavaged with FITC-dextran (0.6 mg/g body weight) diluted in PBS. Serum was collected 4 hr post-gavage and fluorescence intensity was measured at 485/530 nm using a microplate reader (Biotek Synergy 2). For vitamin A-deficiency studies, mice were fed irradiated vitamin A-deficient (Teklad, TD.86143, 0 IU vitamin A/g diet) or control (Teklad, TD.91280, 20 IU vitamin A/g diet) purified diets for at least 4 weeks. All mouse experiments were conducted according to the Institutional Animal Care and Use Committee (IACUC). Animals were cared for by a licensed veterinarian and proper steps were taken to ensure the welfare and minimize the suffering of all animals in the conducted studies.

Bacterial strains and culture C. rodentium were cultured in vitro in 96-well round bottom plates with DMSO (Sigma), 1 nM-10 µM all-trans retinoic acid (RA, Sigma), 10-1000 µM sodium nitroprusside (SNP, Sigma) or 40 µg/ml Kanamycin (Gibco) at 37° C. shaking at medium speed in a microplate reader (Biotek Synergy 2). Bacterial density (OD600) was measured hourly over 16 hr. For bacterial retinol culture studies, bacteria were grown in liquid cultures (B. cereus: Brain-Heart Infusion broth (BHI, Sigma); B. bifidum: MRS broth (Sigma) with 0.05% cysteine (Sigma), in anaerobic chamber; ALDH-expressing E. coli BL21 (DE3) strains: LB with ampicillin (Sigma, 1 mg/ml)) overnight at 30° C. or 37° C. at 180 rpm for 16 hr. Bacterial suspensions were then washed in PBS and diluted 1:3 in fresh LB (Sigma) and incubated with 1 µM all-trans retinol (Sigma) for 3 hr in a 24-well plate at 37° C. with gentle shaking at 120 rpm under light-restricted conditions. To determine bacterial levels, fecal or cultured bacterial DNA was isolated using QIAamp Fast DNA Stool Mini Kit (Qiagen) following the kit protocol. Bacterial DNA was assessed by quantitative PCR (QuantStudio3; Applied Biosystems) using bacterial-specific or 16S primer pairs.

Intestinal Organoids Murine organoids were generated from ileal IECs isolated from male WT C57BL/6J mice as previously described (Woo et al., 2019; Wu et al., 2020). Dissected terminal ileums (12 cm) were opened longitudinally, scraped to remove intestinal contents and outer cells, washed repeatedly in ice-cold PBS, and cut into 1 cm pieces. Ileum pieces were incubated in Chelation Buffer (2 mM EDTA in PBS) for 30 min at 4° C. with rotation. Tissues were subsequently transferred into new tubes containing Shaking Buffer (PBS, 43.3 mM sucrose, 54.9 mM sorbitol) and gently shaken by hand for 2-4 mins. Ileal crypts were resuspended and plated in Matrigel (Corning) overlaid with 500 µl organoid culture media (60% Advanced DMEM/F12 media supplemented with 10 mM HEPES, 2 mM L-glutamate, 40% L-WRN conditioned media, 1×N2 supplement, 1×B27 supplement, 50 ng/mL murine EGF, and 10 µM Y-27632 ROCK inhibitor). Culture media was refreshed every 3-4 days. Organoid cultures were treated with 1 µM Aldh1a2 inhibitor WIN 18446 (Cayman Chemical) for 12 hours and then stimulated with 100 µl of SFB contents at 150 mg/ml PBS for 24 hours. For bacterial culture treatments in organoids, 100 µl of liquid cultures were directly added to organoids containing 1 µM retinol for 24 hours. After incubation, organoids were washed 3 times in PBS and lysed using the RNeasy kit (Qiagen).

METHOD DETAILS C. rodentium infections Mice were orally infected with 109 colony-forming units (CFUs) of C. rodentium suspended in sterile PBS. Post-infection CFUs were measured in stool homogenized in 500 µl PBS in a Tissue Lyser II at 30 Hz for 3 min. Homogenates were serially diluted 10-fold on MacConkey agar (BD) and CFUs were counted after 16 hr incubation at 37° C., normalized to fecal weight. For RA studies, mice were orally gavaged with 300 µg RA or vehicle (DMSO) in 100 µl corn oil q.d. 5 days prior to and during the infection. For RAR inhibitor (RARi) studies, 400 µg BMS493 (Torcis Bioscience) suspended in 10% DMSO/corn oil was administered to mice via oral gavage q.o.d. over 6 days pre-infection and 6 days post-infection. For Aldh1a2 inhibition, mice were orally gavaged with 400 mg/kg of WIN 18446 (Cayman Chemical) or vehicle (DMSO) in 100 µl corn oil for 8 days q.o.d.

CD4$^+$ T Cell Depletion and Flow Cytometry

CD4$^+$ cells were depleted using anti-CD4 monoclonal depletion antibody (clone: GK1.5) or matching isotype control (Rat IgG2B). IL-17A neutralization was performed using anti-IL-17A monoclonal antibody (clone: 17F3) or matching isotype control (Mouse IgG1). Antibodies were administered intraperitoneally, 500 µg per day every 3 days for a total of 3 doses. Efficacy of CD4$^+$ depletion was determined in colonic lamina propria and spleen by flow cytometry. For intestinal lamina propria lymphocytes isolation, tissue pieces were washed with cold PBS and incubated in RPMI with 1 mg/ml Collagenase/Dispase for 30 min at 37° C. with shaking at 200 rpm. Splenocytes were disrupted into single cell suspension by passing the organ through 70 µm filter and RBCs were lysed in ACK lysis buffer (Invitrogen) for 3 min. Cells were stained using the following monoclonal fluorescence-conjugated antibodies: BUV395 anti-CD45.2 (Clone: 104, BD Biosciences), APC-eFluor 780 anti-CD4 (Clone: RM4-5, eBioscience), and APC anti-CD8a (Clone: 53-6.7, eBioscience). All antibodies were diluted in FACS buffer (2% FBS, 0.01 Sodium Azide, PBS). Dead cells were gated out by using the Fixable Violet Dead Cell Stain Kit (Invitrogen). Samples were acquired on the BD LSRFortessa (BD Biosciences) and analyzed with FlowJo Software (Treestar).

IEC isolation and RNA analyses IECs were isolated from distal small intestine (12 cm) or large intestine by shaking tissue in 1 mM EDTA/1 mM DTT 5% FBS at 37° C. for 10 min as described previously (Alenghat et al., 2013). Bacteria were treated with RNAprotect Bacteria Reagent (Qiagen) for 5 min prior to RNA isolation. RNA was extracted from cells using the RNeasy Kit (Qiagen) according to manufacturer's instructions. For RT-qPCR, RNA was treated with DNase I (Invitrogen) and reverse-transcribed with Verso reverse transcriptase (Thermo Scientific). Expression was compared using SYBR (Applied Biosystems) and analyzed in the linear range of amplification. Target gene expression was normalized to an unaffected control gene. All primers used this study are found in Table S1. For global expression analyses, 3-4 biological replicates of IECs from *C. rodentium*-infected GF and SFB-monoassociated mice were compared. Following removal of primers and barcodes, raw reads were processed using Kallisto, which employs pseudo-alignment to assess compatibility between raw reads and genomic targets. Annotations were provided by UCSC with transcripts per million (TPM) as output, which were log 2-transformed and baselined to the median of all samples. Further, transcripts were filtered to include only those with TPM>3 in 100% of samples in at least one condition. Differential expression was assessed with a moderated t-test with p<0.05 and fold-change>1.5. For gene ontology analyses, differential gene lists were submitted to DAVID bioinformatics database (david.ncifcrf.gov)(Huang et al., 2009). Pathway enrichment significance are displayed as log 10-transformed p-values.

ChIP-seq ChIP-seq on IECs was performed as described previously (Wu et al., 2020) with a few modifications. Briefly, cells were fixed for 10 min in 1% formaldehyde at room temperature, followed by quenching with 125 mM glycine for 10 min. After a two-step wash with cold PBS, fixed cells were lysed, and nuclear extracts were washed in TE 0.10% SDS with protease inhibitors and sonicated using a S220 Focused-ultrasonicator (Covaris). Prior to immunoprecipitation, sheared chromatin was precleared for 20 min at 4° C. using Protein G Dynabeads (Thermo Fisher Scientific). Immunoprecipitations were performed using fresh beads and anti-Histone H3 acetyl K27 (H3K27Ac) antibody (Abcam: ab4729) using a SX-8G IP-STAR automated system (Diagenode) with the following wash buffers: (1) RIPA 150 mM NaCl, (2) RIPA 250 mM NaCl, (3) LiCl 250 mM, 0.5% sodium deoxycholate, NP40 0.5%, and (4) TE 0.2% Triton X-100. Immunoprecipitated chromatin were treated with Proteinase K (Thermo Fisher Scientific) at 42° C. for 30 min. 65° C. for 4 hr, and 15° C. for 10 min in elution buffer (TE 250 mM NaCl 0.3% SDS). Phenol:chloroform isoamyl alcohol with Tris-HCl (pH 8.0) and chloroform phase-separation were used to isolate DNA, followed by overnight ethanol precipitation. ChIP DNA was sequenced using Illumina HiSeq 2500 platform. ChIP-seq data were processed using analytic pipelines in galaxy (usegalaxy.org). Following raw read alignment to mm10, MACS2 was used for peak calling and differential peak detection. Peaks were visualized by the UCSC genome browser inBiowardrobe (Kartashov and Barski, 2015). Transcription factor-binding site motifs were identified within 150 bp of the center of the differential peaks using PscanChIP (JASPAR 2018 database) (Zambelli et al., 2013), displayed as the global p-value.

Nitric Oxide Quantification Dissected mouse ileum and colon tissues were opened longitudinally and scraped using a clean microscope slide to collect mucosal scrape. Samples were homogenized in Nitric Oxide (NO) Assay Buffer (Biovision, K262) and treated with perchloric acid (PCA) and potassium hydroxide (KOH) to precipitate interfering proteins. Deproteinized samples were run on a Nitric Oxide Assay kit (Biovision, K262) according to manufacturer instructions. Briefly, samples were added to a 96-well plate and incubated with Nitrate Reductase and enzyme cofactor for 1 hr at room temperature and incubated with enhancer for an additional 10 min. 50 µl of Griess Reagent R1 and R2 were sequentially added to each well. Color was developed for 10 min at room temperature and absorbance was read at 540 nm using a micro-plate reader (Biotek Synergy 2).

Histological tissue analyses Sections of intestine were fixed in 4% paraformaldehyde overnight at 4° C., paraffin embedded, sectioned, and stained with hematoxylin and eosin or periodic acid-Schiff/Alcian blue. For immunofluorescence, distal large intestine was fixed in 4% paraformaldehyde overnight at 4° C. and then placed in 30% sucrose for 24 hr. Tissues were embedded in OCT compound and cut as frozen sections (10 µm). Frozen sections were thawed and blocked with 1% BSA for 1 hr at room temperature. The following antibodies were diluted in 0.5% BSA and incubated with the tissue for 1.5 hr at room temperature: Alexa Fluor 488-anti-GFP (5.0 µg/ml, Invitrogen) and Alexa Fluor 594-Phalloidin (1:200, Invitrogen). Nuclei were stained with DAPI (4',6-Diamidino-2-Phenylindole, Dihydrochloride, 0.5 ug/ml, Life Technologies). Slides were washed and then mounted using Fluoromount-G (Invitrogen) and imaged on a Nikon AlR LUN-V inverted confocal microscope.

SFB and *B. bifidum* ALDH constructs SFB ALDH$^{WT}$ (WP_007440235.1) and *B. bifidum* ALDH$^{WT}$ (WP_013390136.1, WP_015438559.1) genes were codon-optimized for expression in *E. coli* and cloned into the NdeI/BamHI site of the inducible pET-21a(+) or constitutive pET-23a(+) plasmid (GenScript). ALDH$^{MUT}$ variants were generated by substituting the catalytic glutamate [E] with an alanine [A] residue at amino acid position 209 and 244 of SFB ALDH and *B. bifidum* ALDH, respectively. Plasmids were transformed into BL21(DE3) *E. coli* Competent Cells (Thermo Scientific) and positive transformants were selected using ampicillin (Sigma, 1 mg/ml) and screened by PCR. Successfully transformed clones were grown in LB broth (Sigma) containing Ampicillin (Sigma, 1 mg/ml) at 37° C. 180 rpm until optical density at 600 (OD600) reached 0.4-0.6, and further cultured in presence of 0.5 mM isopropylthio-β-galactoside (IPTG, Invitrogen) for 4 hours to induce protein expression.

Retinoic acid quantification Intestinal contents and IECs pellets were collected under dark conditions and homogenized in PBS. Extracts were run on a retinoic acid ELISA kit (My BioSource, MBS706971) according to manufacturer instructions. Briefly, samples were incubated with 50 µl HRP-conjugated antibody for 40 min at 37° C., washed 5 times with wash buffer, and incubated with TMB substrate for 20 min at 37° C. The reaction was quenched, and absorbance was measured of each well using a micro-plate reader (Biotek Synergy 2) set to 450 nm. For explant experiments, equal sections of terminal ileum were taken from GF and SFB-monoassociated mice and cultured in a 24-well plate with 1 µM all-trans retinol (Sigma) for 3 hr at 37° C. without light. RA was measured in culture supernatant or bacterial culture media after incubation. For RA quantification of ALDH$^{WT}$ and ALDH$^{MUT}$ strains, cultures were treated with 1p M all-trans retinol (Sigma) and IPTG for 4 hours.

Aldehyde dehydrogenase activity Samples were homogenized in ice-cold ALDH assay buffer (Sigma, MAK082) for 3 min at 30 Hz and spun down at 13,000×g for 10 min. ALDH activity was measured according to manufacturer's instructions (Sigma, MAK082). Briefly, 50 µl of supernatants with equal protein concentrations determined using Pierce BCA Protein Assay Kit (Thermo Scientific) were combined with ALDH substrate and acetaldehyde in 96-well plates. Background controls were performed in parallel by omitting acetaldehyde from the reaction. Reactions were incubated at room temperature for 5 min and absorbance at 450 nm was measured in 5 min intervals using a micro-plate reader (Biotek Synergy 2). Enzymatic activity was calculated as a function of amount NADH generated over time.

Protein modeling and sequence alignment to predict 3D structures, protein sequences were submitted to the Phyre2 server (www.sbg.bio.ic.ac.uk/phyre2) (Kelley et al., 2015) and modeled after existing Protein Data Bank templates (bcALDH1A1: PDB c4pt3C; SFB ALDH: PDB c6k0zA; *B. bifidum* ALDH: PDB c4f9iA). Figures were generated using the PyMOL Molecular Graphics System, Version 2.4 Schrodinger, LLC (pymol.org/). The superimpose function was used to determine structural similarity to bcALDH1A1, reported as the overall root-mean-square deviation (RMSD) value. Microbiome shotgun sequencing data obtained from the stool of 24 healthy patients that had not received antibiotics within 6 months prior to the study (Lewis et al., 2015) were aligned against the SFB ALDH (WP_007440235.1) and *B. bifidum* ALDH (WP_015438559.1) sequences using Bowtie2. Prevalence of these genes are expressed as ALDH counts per million mapped bacterial reads.

QUANTIFICATION AND STATISTICAL ANALYSIS All statistical analyses were performed using GraphPad Prism 8.0. Statistical significance was determined by Student's t-test or ANOVA. All data meet the assumptions of the statistical tests used. Results are shown as mean±SEM and considered significant at $p<0.05$ (\*); $p<0.01$ (\*\*); $p<0.001$ (\*\*\*). Additional quantification and statistical information (including exact value of n, and what n represents) are included in the figures or figure legends where appropriate.

DATA AND CODE AVAILABILITY Datasets from this study have been deposited in the NCBI Gene Expression Omnibus (GEO) database under the following accession identifiers: RNA-seq (GSE182630), ChIP-seq 789 (GSE182628).

Example 2. Gene Expression in Liver when Delivered RA Bacteria

Aldh-Expressing Bacteria Regulate Genes in Liver

| Fold change (MUT/WT) | |
|---|---|
| 0.126721 | Fgf21 → fibrosis |
| 0.377308 | Klf10 |
| 0.407687 | Gm6484 |
| 0.425114 | Epha2 |
| 0.440686 | G0s2 |
| 0.469042 | Efna1 |
| 0.485375 | Txnip |
| 0.511078 | Dusp6 |
| 0.54296 | Sox9 |
| 0.544202 | Irf2bp2 |
| 0.548584 | Bhlhe40 |
| 0.553748 | Ppp1r3c |

-continued

| Fold change (MUT/WT) | |
|---|---|
| 0.563863 | Cyr61 |
| 0.564013 | Sik1 |
| 0.570923 | Nuak2 |
| 0.639178 | Gse1 |
| 0.648123 | Kcnk5 |
| 0.658817 | Gm14493 |
| 0.660393 | Mid1ip1 |
| 1.636629 | Adh7 |
| 1.685296 | 1300015D01Rik |
| 1.80707 | Slc22a3 |
| 2.168162 | Hhex |
| 2.236167 | Cd44 |
| 2.274074 | Bmpr2 |
| 2.277543 | Malat1 |
| 2.450034 | Mmd2 |
| 2.540939 | Lnpep |
| 2.604397 | Glt25d2 |
| 2.742722 | Cd53 |
| 2.750367 | Arid5b |
| 2.764482 | Zfp871 |
| 2.836587 | Gm20417 |
| 3.219085 | Phlda1 |
| 3.887347 | A530084C06Rik |
| 3.954885 | Foxq1 |
| 4.224875 | F830016B08Rik |
| 4.274857 | Cyp26b1 |
| 5.030775 | Gm17414 |
| 5.26948 | Gm16348 |
| 8.606518 | Gm17041 |
| 9.189338 | Cish |
| 63.3135 | 4930565N06Rik |

Altered with Delivery of RA Bacteria

| Pathway | PValue |
|---|---|
| MAPK signaling pathway | 0.004522434 |
| PI3K-Akt signaling pathway | 0.01165463 |
| Axon guidance | 0.072093947 |
| Cytokine-cytokine receptor interaction | 0.001006 |
| Leishmaniasis | 0.003281 |
| Osteoclast differentiation | 0.005293 |
| Chemokine signaling pathway | 0.006753 |
| Regulation of pluripotency of stem cells | 0.007689 |
| Type II diabetes mellitus | 0.008538 |
| Fc gamma R-mediated phagocytosis | 0.008648 |
| Hematopoietic cell lineage | 0.009315 |
| TGF-beta signaling pathway | 0.00966 |
| Choline metabolism in cancer | 0.010747 |
| Epstein-Barr virus infection | 0.015869 |
| Inflammatory bowel disease | 0.017104 |
| Influenza A | 0.017973 |
| Asthma | 0.020125 |
| Tuberculosis | 0.020954 |
| Maturity onset diabetes of the young | 0.023282 |
| Sphingolipid signaling pathway | 0.023538 |
| myeloid leukemia | 0.029141 |
| Rheumatoid arthritis | 0.041046 |
| Gastric cancer | 0.042919 |
| Antigen processing and presentation | 0.044659 |
| Hippo signaling pathway | 0.049314 |

| Name | q-value (BF) |
|---|---|
| O-linked glycosylation of mucins | 2.41E−02 |
| Cholesterol biosynthesis pathway | 3.75E−02 |
| ECM regulators and secreted factors | 6.33E−02 |
| Extracellular matrix proteins | 6.48E−02 |

-continued

| Name | q-value (BF) |
|---|---|
| Steroid Biosynthesis | 1.55E−01 |
| Immunoregulatory interactions | 4.99E−03 |
| Chemokine receptors bind chemokines | 9.12E−02 |
| G alpha (i) signalling events | 9.76E−02 |
| Interleukin-10 signaling | 1.01E−01 |
| Interleukin-4 and 13 signaling | 1.03E−01 |
| Myometrial relaxation and contraction pathways | 1.25E−01 |
| Chemokine signaling pathway | 1,69E−01 |
| Staphylococcus aureus infection | 1.92E−01 |
| Network map of SARS-COV-2 signaling pathway | 2,42E−01 |
| Prostaglandin signaling | 2.74E−01 |

RA-Sensitive Gene Serum Amyloid A-1/2

| | Gene | P-value | FDR | FC (WT/MUT) |
|---|---|---|---|---|
| | Saa1 | 0.0066 | 0.6850 | 2.24 |
| | Saa2 | 0.0010 | 0.2420 | 3.12 |
| Liver | Saa3 | 0.3599 | 1.0000 | 1.49 |
| | Saa4 | 0.1596 | 1.0000 | 0.89 |

Example 3. Gene Expression in Intestine when Delivered RA Bacteria

Aldh-Expressing Bacteria Regulate Genes in Intestine

| FC (WT/MUT) | |
|---|---|
| 1.610305702 | Tsix |
| 1.392092269 | Xist |
| 0.663839646 | Ccdc21 |
| 0.476561528 | Csf1 |
| 0.427790471 | Alas2 |
| 0.404625423 | Hbb-b2 |
| 0.392729953 | Hbb-b1 |
| 0.379950281 | Hba-a1 |
| 0.360368808 | Serpina1e |
| 0.318197062 | Hba-a2 |
| 0.141198764 | Ang4 |
| 0.015563259 | Begain |

Altered with Delivery of RA Bacteria

| Name | q-value BF |
|---|---|
| response to organophosphorus | 2.86E−02 |
| circadian temperature homeostasis | 4.49E−02 |
| response to purine-containing compound | 6.59E−02 |
| response to cAMP | 9.18E−02 |
| response to lipid | 2.08E−01 |
| external encapsulating structure organization | 3.61E−22 |
| extracellular matrix organization | 2.13E−21 |
| extracellular structure organization | 2.33E−21 |
| cell adhesion | 1.15E−17 |
| vasculature development | 1.52E−12 |
| blood vessel development | 1.61E−11 |
| collagen fibril organization | 4.38E−10 |

REFERENCES

Abt, M. C., and Pamer, E. G. (2014). Commensal bacteria mediated defenses against pathogens. *Curr. Opin. Immunol.* 29, 16-22.

Alenghat, T., Osborne, L. C., Saenz, S. A., Kobuley, D., Ziegler, C. G. K., Mullican, S. E., Choi, I., Grunberg, S., Sinha, R., Wynosky-Dolfi, M., et al. (2013). Histone deacetylase 3 coordinates commensal-bacteria-dependent intestinal homeostasis. *Nature* 504, 153-157. 799

Amatullah, H., and Jeffrey, K. L. (2020). Epigenome-metabolome-microbiome axis in health and IBD. *Curr. Opin. Microbiol.* 56, 97-108.

Ansari, I., Raddatz, G., Gutekunst, J., Ridnik, M., Cohen, D., Abu-Remaileh, M., Tuganbaev, T., Shapiro, H., Pikarsky, E., Elinav, E., et al. (2020). The microbiota programs DNA methylation to control intestinal homeostasis and inflammation. *Nat. Microbiol.* 5, 610-619.

Arnold, S. L. M., Kent, T., Hogarth, C. A., Griswold, M. D., Amory, J. K., and Isoherranen, N. (2015). Pharmacological inhibition of ALDH1A in mice decreases all-trans retinoic acid concentrations in a tissue specific manner. *Biochem. Pharmacol.* 95, 177-192.

Arrowsmith, C. H., Bountra, C., Fish, P. V., Lee, K., and Schapira, M. (2012). Epigenetic protein families: A new frontier for drug discovery. *Nat. Rev. Drug Discov.* 11, 384-400.

Atarashi, K., Tanoue, T., Ando, M., Kamada, N., Nagano, Y., Narushima, S., Suda, W., Imaoka, A., Setoyama, H., Nagamori, T., et al. (2015). Th17 Cell Induction by Adhesion of Microbes to Intestinal Epithelial Cells. *Cell* 163, 367-380.

Benson, A., Pifer, R., Behrendt, C. L., Hooper, L. V., and Yarovinsky, F. (2009). Gut Commensal 813 Bacteria Direct a Protective Immune Response against Toxoplasma gondii. *Cell Host Microbe* 6, 814 187-196.

Benson, M. J., Pino-Lagos, K., Rosemblatt, M., and Noelle, R. J. (2007). All-trans retinoic acid mediates enhanced T reg cell growth, differentiation, and gut homing in the face of high levels of co-stimulation. *J. Exp. Med.* 204, 1765-1774.

Bhinder, G., Stahl, M., Sham, H. P., Crowley, S. M., Morampudi, V., Dalwadi, U., Ma, C., Jacobson, K., and Vallance, B. A. (2014). Intestinal epithelium-specific MyD88 signaling impacts host susceptibility to infectious colitis by promoting protective goblet cell and antimicrobial responses. *Infect. Immun.*

Biesalski, H. K., Chichili, G. R., Frank, J., von Lintig, J., and Nohr, D. (2007). Conversion of β-Carotene to Retinal Pigment. *Vitam. Horm.* 75, 117-130.

Cabrera, G., Femindez-Brando, R. J., Abrey-Recalde, M. J., Baschkier, A., Pinto, A., Goldstein, J., Zotta, E., Meiss, R., Rivas, M., and Palermo, M. S. (2014). Retinoid levels influence enterohemorrhagic *Escherichia coli* infection and shiga toxin 2 susceptibility in mice. *Infect. Immun.* 82, 3948-3957.

Cha, H.-R., Chang, S.-Y., Chang, J.-H., Kim, J.-O., Yang, J.-Y., Kim, C.-H., and Kweon, M.-N. (2010). Downregulation of Th17 Cells in the Small Intestine by Disruption of Gut Flora in the Absence of Retinoic Acid. *J. Immunol.* 184, 6799-6806.

Chang, P. V., Hao, L., Offermanns, S., and Medzhitov, R. (2014). The microbial metabolite butyrate regulates intestinal macrophage function via histone deacetylase inhibition. *Proc. Natl. Acad. Sci. U.S.A* 111, 2247-2252.

Christian, P., and West, K. P. (1998). Interactions between zinc and vitamin A: An update. *Am. J. Clin. Nutr.* 68, 435S-441S.

Chung, H., Pamp, S. J., Hill, J. A., Surana, N. K., Edelman, S. M., Troy, E. B., Reading, N. C., Villablanca, E. J., Wang, S., Mora, J. R., et al. (2012). Gut immune maturation depends on colonization with a host-specific microbiota. *Cell* 149, 1578-1593

Creyghton, M. P., Cheng, A. W., Welstead, G. G., Kooistra, T., Carey, B. W., Steine, E. J., Hanna, J., Lodato, M. A., Frampton, G. M., Sharp, P. A., et al. (2010). Histone H3K27ac separates active from poised enhancers and predicts developmental state. *Proc. Natl. Acad. Sci. U.S.A* 107, 21936-21936.

Dalile, B., Van Oudenhove, L., Vervliet, B., and Verbeke, K. (2019). The role of short-chain fatty acids in microbiota-gut-brain communication. *Nat. Rev. Gastroenterol. Hepatol.* 16, 461-845 473.

Dibley, M. J., Sadjimin, T., Kjolhede, C. L., and Moulton, L. H. (1996). Vitamin A supplementation fails to reduce incidence of acute respiratory illness and diarrhea in preschool-age Indonesian children. *J. Nutr.* 126, 434-442.

Erkelens, M. N., and Mebius, R. E. (2017). Retinoic Acid and Immune Homeostasis: A Balancing Act. *Trends Immunol.* 38, 168-180.

Fellows, R., Denizot, J., Stellato, C., Cuomo, A., Jain, P., Stoyanova, E., Balázsi, S., Hajnidy, Z., Liebert, A., Kazakevych, J., et al. (2018). Microbiota derived short chain fatty acids promote histone crotonylation in the colon through histone deacetylases. *Nat. Commun.* 9, 105.

Furusawa, Y., Obata, Y., Fukuda, S., Endo, T. A., Nakato, G., Takahashi, D., Nakanishi, Y., Uetake, C., Kato, K., Kato, T., et al. (2013). Commensal microbe-derived butyrate induces the differentiation of colonic regulatory T cells. *Nature* 504, 446-450.

Gallo, R. L., and Hooper, L. V. (2012). Epithelial antimicrobial defence of the skin and intestine. *Nat. Rev. Immunol.* 12, 503-516.

Ganal, S. C., Sanos, S. L., Kallfass, C., Oberle, K., Johner, C., Kirschning, C., Lienenklaus, S., Weiss, S., Staeheli, P., Aichele, P., et al. (2012). Priming of Natural Killer Cells by Nonmucosal Mononuclear Phagocytes Requires Instructive Signals from Commensal Microbiota. *Immunity* 37, 171-186.

Garland, C. D., Lee, A., and Dickson, M. R. (1982). Segmented filamentous bacteria in the rodent small intestine: Their colonization of growing animals and possible role in host resistance to Salmonella. *Microb. Ecol.* 8, 181-190.

Gattu, S., Bang, Y.-J., Pendse, M., Dende, C., Chara, A. L., Harris, T. A., Wang, Y., Ruhn, K. A., Kuang, Z., Sockanathan, S., et al. (2019). Epithelial retinoic acid receptor 3 regulates serum amyloid A expression and vitamin A-dependent intestinal immunity. *Proc. Natl. Acad. Sci.* 116, 2018-2069.

Goto, Y., Panea, C., Nakato, G., Cebula, A., Lee, C., Diez, M. G., Laufer, T. M., Ignatowicz, L., and Ivanov, I. I. (2014). Segmented filamentous bacteria antigens presented by intestinal dendritic cells drive mucosal Th17 cell differentiation. *Immunity* 40, 594-607.

Green, H. N., and Mellanby, E. (1928). Vitamin a as an anti-infective agent. *Br. Med. J.* 2, 691-696.

Grizotte-Lake, M., Zhong, G., Duncan, K., Kirkwood, J., Iyer, N., Smolenski, I., Isoherranen, N., and Vaishnava, S. (2018). Commensals Suppress Intestinal Epithelial Cell Retinoic Acid Synthesis to Regulate Interleukin-22 Activity and Prevent Microbial Dysbiosis. *Immunity* 49, 1103-1115.e6.

Gundra, U. M., Girgis, N. M., Gonzalez, M. A., Tang, M. S., Van Der Zande, H. J. P., Lin, J. Da, Ouimet, M., Ma, L. J., Poles, J., Vozhilla, N., et al. (2017). Vitamin A mediates conversion of monocyte-derived macrophages into tissue-resident macrophages during alternative activation. *Nat. Immunol.* 18, 642-653.

Hall, J. A., Grainger, J. R., Spencer, S. P., and Belkaid, Y. (2011a). The role of retinoic acid in tolerance and immunity. *Immunity* 35, 13-22.

Hall, J. A., Cannons, J. L., Grainger, J. R., Dos Santos, L. M., Hand, T. W., Naik, S., Wohlfert, E. A., Chou, D. B., Oldenhove, G., Robinson, M., et al. (2011b). Essential role for retinoic acid in the promotion of CD4+ T cell effector responses via retinoic acid receptor alpha. *Immunity* 34, 435-447.

Hantke, K. (2005). Bacterial zinc uptake and regulators. *Curr. Opin. Microbiol.* 8, 196-202.

Heczko, U., Abe, A., and Finlay, B. B. (2000). Segmented filamentous bacteria prevent colonization of enteropathogenic *Escherichia coli* 0103 in rabbits. *J. Infect. Dis.* 181, 1027-892.

Hong, S. H., Ngo, H. P. T., Nam, H. K., Kim, K. R., Kang, L. W., and Oh, D. K. (2016). Alternative biotransformation of retinal to retinoic acid or retinol by an aldehyde dehydrogenase from *Bacillus cereus*. *Appl. Environ. Microbiol.* 82, 3940-3946.

Huang, D. W., Sherman, B. T., and Lempicki, R. A. (2009). Systematic and integrative analysis of large gene lists using DAVID bioinformatics resources. *Nat. Protoc.* 4.

Huang, Z., Liu, Y., Q i, G., Brand, D., and Zheng, S. (2018). Role of Vitamin A in the Immune 899 System. *J. Clin. Med.* 7, 258.

Ivanov, I. I., Atarashi, K., Manel, N., Brodie, E. L., Shima, T., Karaoz, U., Wei, D., Goldfarb, K. C., Santee, C. A., Lynch, S. V, et al. (2009). Induction of intestinal Th17 cells by segmented filamentous bacteria. *Cell* 139, 485-498.

Iyer, N., Grizotte-Lake, M., Duncan, K., Gordon, S. R., Palmer, A. C. S., Calvin, C., Zhong, G., Isoherranen, N., and Vaishnava, S. (2020). Epithelium intrinsic Vitamin A signaling coordinates pathogen clearance in the gut via IL-18. *PLoS Pathog.* 16, e1008360.

Jang, H. J., Yoon, S. H., Ryu, H. K., Kim, J. H., Wang, C. L., Kim, J. Y., Oh, D. K., and Kim, S. W. (2011). Retinoid production using metabolically engineered *Escherichia coli* with a two-phase culture system. *Microb. Cell Fact.* 10.

Jang, H. J., Ha, B. K., Zhou, J., Ahn, J., Yoon, S. H., and Kim, S. W. (2015). Selective retinol production by modulating the composition of retinoids from metabolically engineered *E. coli*. *Biotechnol. Bioeng.* 112, 1604-1612.

Jijon, H. B., Suarez-Lopez, L., Diaz, O. E., Das, S., De Calisto, J., Yaffe, M. B., Pittet, M. J., Mora, J. R., Belkaid, Y., Xavier, R. J., et al. (2018). Intestinal epithelial cell-specific RARa depletion results in aberrant epithelial cell homeostasis and underdeveloped immune system. *Mucosal Immunol.* 11, 703-715.

Jonsson, H., Hugerth, L. W., Sundh, J., Lundin, E., and Andersson, A. F. (2020). Genome sequence of segmented filamentous bacteria present in the human intestine. *Commun. Biol.* 3.

Kaiko, G. E., Ryu, S. H., Koues, O. I., Collins, P. L., Solnica-Krezel, L., Pearce, E. J., Pearce, E. L., Oltz, E. M., and Stappenbeck, T. S. (2016). The Colonic Crypt Protects Stem Cells from Microbiota-Derived Metabolites. *Cell* 165, 1708-1720.

Kamada, N., Kim, Y. G., Sham, H. P., Vallance, B. A., Puente, J. L., Martens, E. C., and Ntnez, G. (2012). Regulated virulence controls the ability of a pathogen to compete with the gut microbiota. *Science* (80). 336, 1325-1329.

Kartashov, A. V., and Barski, A. (2015). BioWardrobe: An integrated platform for analysis of epigenomics and transcriptomics data. *Genome Biol.* 16, 158.

Kelley, L. A., Mezulis, S., Yates, C. M., Wass, M. N., and Sternberg, M. J. E. (2015). The Phyre2 web portal for protein modeling, prediction and analysis. *Nat. Protoc.* 10, 845-858.

Kelly, D., Kotliar, M., Woo, V., Jagannathan, S., Whitt, J., Moncivaiz, J., Aronow, B. J., Dubinsky, M. C., Hyams, J. S., Markowitz, J. F., et al. (2018). Microbiota-sensitive epigenetic signature predicts inflammation in Crohn's disease. *JCI Insight* 3.

Kim, M. H., Taparowsky, E. J., and Kim, C. H. (2015). Retinoic Acid Differentially Regulates The Migration Of Innate Lymphoid Cell Subsets To The Gut. *Immunity* 43, 107-119.

Ladinsky, M. S., Araujo, L. P., Zhang, X., Veltri, J., Galan-Diez, M., Soualhi, S., Lee, C., Irie, K., Pinker, E. Y., Narushima, S., et al. (2019). Endocytosis of commensal antigens by intestinal epithelial cells regulates mucosal T cell homeostasis. *Science* (80). 363, eaat4042.

Laubach, V. E., Shesely, E. G., Smithies, O., and Sherman, P. A. (1995). Mice lacking inducible nitric oxide synthase are not resistant to lipopolysaccharide-induced death. *Proc. Natl. Acad. Sci. U.S.A*

Lavelle, A., and Sokol, H. (2020). Gut microbiota-derived metabolites as key actors in inflammatory bowel disease. *Nat. Rev. Gastroenterol. Hepatol.* 17, 223-237. 941

Lewis, J. D., Chen, E. Z., Baldassano, R. N., Otley, A. R., Griffiths, A. M., Lee, D., Bittinger, K., Bailey, A., Friedman, E. S., Hoffmann, C., et al. (2015). Inflammation, Antibiotics, and Diet as Environmental Stressors of the Gut Microbiome in Pediatric Crohn's Disease. *Cell Host Microbe.*

Long, K. Z., Garcia, C., Santos, J. I., Rosado, J. L., Hertzmark, E., DuPont, H. L., and Ko, G. P. 946 (2007). Vitamin A supplementation has divergent effects on norovirus infections and clinical symptoms among Mexican children. *J. Infect. Dis.* 196, 978-985.

Madison, B. B., Dunbar, L., Qiao, X. T., Braunstein, K., Braunstein, E., and Gumucio, D. L. (2002). Cis elements of the villin gene control expression in restricted domains of the vertical (crypt) and horizontal (duodenum, cecum) axes of the intestine. J. *Biol. Chem.* 277, 33275-951 33283.

Matsumoto, M., Kunisawa, A., Hattori, T., Kawana, S., Kitada, Y., Tamada, H., Kawano, S., Hayakawa, Y., Iida, J., and Fukusaki, E. (2018). Free D-amino acids produced by commensal bacteria in the colonic lumen. *Sci. Rep.* 8, 17915.

McCarville, J. L., Chen, G. Y., Cuevas, V. D., Troha, K., and Ayres, J. S. (2020). Microbiota Metabolites in Health and Disease. *Annu. Rev. Immunol.* 38, 147-170.

McDaniel, K. L., Restori, K. H., Dodds, J. W., Kennett, M. J., Ross, A. C., and Cantornaa, M. T. (2015). Vitamin A-deficient hosts become nonsymptomatic reservoirs of *Escherichia coli*-like enteric infections. *Infect. Immun.* 83, 2984-2991.

McDevitt, C. A., Ogunniyi, A. D., Valkov, E., Lawrence, M. C., Kobe, B., McEwan, A. G., and Paton, J. C. (2011). A molecular mechanism for bacterial susceptibility to Zinc. *PLoS Pathog.* 7, e1002357.

Metzler, M. A., Raja, S., Elliott, K. H., Friedl, R. M., Tran, N. Q. H., Brugmann, S. A., Larsen, M., and Sandell, L. L. (2018). RDH10-mediated retinol metabolism and RARa-mediated retinoic acid signaling are required for submandibular salivary gland initiation. *Dev.* 145, dev164822.

Mielke, L. A., Jones, S. A., Raverdeau, M., Higgs, R., Stefanska, A., Groom, J. R., Misiak, A., Dungan, L. S., Sutton, C. E., Streubel, G., et al. (2013). Retinoic acid expression associates with enhanced IL-22 production by γδ T cells and innate lymphoid cells and attenuation of intestinal inflammation. *J. Exp. Med.* 210, 1117-1124.

Mucida, D., Park, Y., Kim, G., Turovskaya, O., Scott, I., Kronenberg, M., and Cheroutre, H. (2007). Reciprocal TH17 and regulatory T cell differentiation mediated by retinoic acid. *Science* (80-.). 317, 256-260.

Mundy, R., MacDonald, T. T., Dougan, G., Frankel, G., and Wiles, S. (2005). Citrobacterrodentium of mice and man. *Cell. Microbiol.* 7, 1697-1706.

Navabi, N., Whitt, J., Wu, S. en, Woo, V., Moncivaiz, J., Jordan, M. B., Vallance, B. A., Way, S. S., and Alenghat, T. (2017). Epithelial Histone Deacetylase 3 Instructs Intestinal Immunity by Coordinating Local Lymphocyte Activation. *Cell Rep.* 19, 1165-1175.

Omenetti, S., Bussi, C., Metidji, A., Iseppon, A., Lee, S., Tolaini, M., Li, Y., Kelly, G., Chakravarty, P., Shoaie, S., et al. (2019). The Intestine Harbors Functionally Distinct Homeostatic Tissue-Resident and Inflammatory Th17 Cells. *Immunity* 51, 77-89.

Osbelt, L., Thiemann, S., Smit, N., Lesker, T. R., Schroter, M., Gilvez, E. J. C., Schmidt-Hohagen, K., Pils, M. C., Muhlen, S., Dersch, P., et al. (2020). Variations in microbiota composition of laboratory mice influence *Citrobacter rodentium* infection via variable short-chain fatty acid production. *PLoS Pathog.* 16, e1008448.

Paik, J., Haenisch, M., Muller, C. H., Goldstein, A. S., Arnold, S., Isoherranen, N., Brabb, T., Treuting, P. M., and Amory, J. K. (2014). Inhibition of retinoic acid biosynthesis by the bisdichloroacetyldiamine WIN 18,446 markedly suppresses spermatogenesis and alters retinoid metabolism in mice. *J. Biol. Chem.* 289, 15104-15117.

Peterson, L. W., and Artis, D. (2014). Intestinal epithelial cells: Regulators of barrier function and immune homeostasis. *Nat. Rev. Immunol.* 14, 141-153.

Price, A. E., Shamardani, K., Lugo, K. A., Deguine, J., Roberts, A. W., Lee, B. L., and Barton, G. M. (2018). A Map of Toll-like Receptor Expression in the Intestinal Epithelium Reveals Distinct Spatial, Cell Type-Specific, and Temporal Patterns. *Immunity* 49, 560-575.

Rada-Iglesias, A., Bajpai, R., Swigut, T., Brugmann, S. A., Flynn, R. A., and Wysocka, J. (2011). A unique chromatin signature uncovers early developmental enhancers in humans. *Nature* 470, 279-283.

Rahman, M. M., Wahed, M. A., Fuchs, G. J., Baqui, A. H., and Alvarez, J. O. (2002). Synergistic effect of zinc and vitamin A on the biochemical indexes of vitamin A nutrition in children. *Am. J. Clin. Nutr.* 75, 92-98.

Rajaii, F., Bitzer, Z. T., Xu, Q., and Sockanathan, S. (2008). Expression of the dominant negative retinoid receptor, RAR403, alters telencephalic progenitor proliferation, survival, and cell fate specification. *Dev. Biol.* 316, 371-382.

Ramanan, D., and Cadwell, K. (2016). Intrinsic Defense Mechanisms of the Intestinal Epithelium. *Cell Host Microbe* 19, 434-441.

Rooks, M. G., and Garrett, W. S. (2016). Gut microbiota, metabolites and host immunity. *Nat. Rev. Immunol.* 16, 341-352.

Sano, T., Huang, W., Hall, J. A., Yang, Y., Chen, A., Gavzy, S. J., Lee, J. Y., Ziel, J. W., Miraldi, E. R., Domingos, A. I., et al. (2015). An IL-23R/IL-22 Circuit Regulates Epithelial Serum Amyloid A to Promote Local Effector Th17 Responses. *Cell* 163, 381-393.

Seamons, A., Haenisch, M., Meeker, S., Pershutkina, O., Brabb, T., Treuting, P. M., and Paik, J. (2020). Protective effects of aldh1a enzyme inhibition on *helicobacter*-induced colitis in smad3−/− mice are associated with altered a4B7 integrin expression on activated t cells. Nutrients 12, 1-13.

Semba, R. D. (1999). Vitamin A and immunity to viral, bacterial and protozoan infections. *Proc. Nutr. Soc.* 58, 719-727.

Shi, Z., Zou, J., Zhang, Z., Zhao, X., Noriega, J., Zhang, B., Zhao, C., Ingle, H., Bittinger, K., Mattei, L. M., et al. (2019). Segmented Filamentous Bacteria Prevent and Cure Rotavirus Infection. *Cell* 179, 644-658.e13.

Smith, J. C. (1980). THE VITAMIN A-ZINC CONNECTION: A REVIEW. *Ann. N. Y. Acad. Sci.* 355, 62-75.

Snyder, L. M., McDaniel, K. L., Tian, Y., Wei, C. H., Kennett, M. J., Patterson, A. D., Catharine Ross, A., and Cantorna, M. T. (2019). Retinoic acid mediated clearance of *Citrobacter rodentium* in vitamin A deficient mice requires CD11b+ and T cells. Front. *Immunol.* 9, 3090.

Sommer, A. (2008). Vitamin A deficiency and clinical disease: An historical overview. *J. Nutr.* 138, 1835-1839.

Spaans, S. K., Weusthuis, R. A., van der Oost, J., and Kengen, S. W. M. (2015). NADPH-generating systems in bacteria and archaea. *Front. Microbiol.* 6, 742.

Sporer, A. J., Kahl, L. J., Price-Whelan, A., and Dietrich, L. E. P. (2017). Redox-based regulation of bacterial development and behavior. *Annu. Rev. Biochem.* 86, 777-797.

Symonds, E. L., Riedel, C. U., O'Mahony, D., Lapthome, S., O'Mahony, L., and Shanahan, F. (2009). Involvement of T helper type 17 and regulatory T cell activity in *Citrobacter rodentium* invasion and inflammatory damage. *Clin. Exp. Immunol.* 157, 148-154.

Takahashi, H., Kanno, T., Nakayamada, S., Hirahara, K., Sciume, G., Muljo, S. A., Kuchen, S., Casellas, R., Wei, L., Kanno, Y., et al. (2012). TGF-β and retinoic acid induce the microRNA miR-10a, which targets Bcl-6 and constrains the plasticity of helper T cells. *Nat. Immunol.* 29, 587-595.

Takahashi, K., Sugi, Y., Hosono, A., and Kaminogawa, S. (2009). Epigenetic Regulation of TLR4 Gene Expression in Intestinal Epithelial Cells for the Maintenance of Intestinal Homeostasis. *J. Immunol.* 183, 6522-6529.

Uematsu, S., Fujimoto, K., Jang, M. H., Yang, B. G., Jung, Y. J., Nishiyama, M., Sato, S., Tsujimura, T., Yamamoto, M., Yokota, Y., et al. (2008). Regulation of humoral and cellular gut immunity by lamina propria dendritic cells expressing Toll-like receptor 5. *Nat. Immunol.* 9, 769-776.

Vallance, B. A., Deng, W., De Grado, M., Chan, C., Jacobson, K., and Finlay, B. B. (2002). Modulation of inducible nitric oxide synthase expression by the attaching and effacing bacterial pathogen *Citrobacter rodentium* in infected mice. *Infect. Immun.*

Wang, C., Kang, S. G., HogenEsch, H., Love, P. E., and Kim, C. H. (2010). Retinoic Acid Determines the Precise Tissue Tropism of Inflammatory Th17 Cells in the Intestine. *J. Immunol.* 184, 5519-5526.

Wikoff, W. R., Anfora, A. T., Liu, J., Schultz, P. G., Lesley, S. A., Peters, E. C., and Siuzdak, G. (2009). Metabolomics analysis reveals large effects of gut microflora on mammalian blood metabolites. *Proc. Natl. Acad. Sci. U.S.A* 106, 3698-3703.

Woo, V., and Alenghat, T. (2017). Host-microbiota interactions: epigenomic regulation. *Curr. Opin. Immunol.* 44, 52-60.

Woo, V., Eshleman, E. M., Rice, T., Whitt, J., Vallance, B. A., and Alenghat, T. (2019). Microbiota Inhibit Epithelial Pathogen Adherence by Epigenetically Regulating C-Type Lectin Expression. *Front. Immunol.* 10, 1-10.

World Health Organization (2009). Global prevalence of vitamin A deficiency in populations at risk 1995-2005: WHO global database on vitamin A deficiency. *WHO Iris* 55.

Wu, S. en, Hashimoto-Hill, S., Woo, V., Eshleman, E. M., Whitt, J., Engleman, L., Karns, R., Denson, L. A., Haslam, D. B., and Alenghat, T. (2020). Microbiota-derived metabolite promotes HDAC3 activity in the gut. *Nature* 586, 108-112.

Yang, W., Yu, T., Huang, X., Bilotta, A. J., Xu, L., Lu, Y., Sun, J., Pan, F., Zhou, J., Zhang, W., et al. (2020). Intestinal microbiota-derived short-chain fatty acids regulation of immune cell IL-22 production and gut immunity. *Nat. Commun.* 11, 4457.

Zambelli, F., Pesole, G., and Pavesi, G. (2013). PscanChIP: Finding over-represented transcription factor-binding site motifs and their correlations in sequences from ChIP-Seq experiments. *Nucleic Acids Res.*

Zeng, R., Bscheider, M., Lahl, K., Lee, M., and Butcher, E. C. (2016). Generation and transcriptional programming of intestinal dendritic cells: Essential role of retinoic acid. *Mucosal Immunol.* 9, 183-193.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. All accessioned information (e.g., as identified by PUBMED, PUBCHEM, NCBI, UNIPROT, or EBI accession numbers) and publications in their entireties are incorporated into this disclosure by reference in order to more fully describe the state of the art as known to those skilled therein as of the date of this disclosure. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

SEQUENCE LISTING

```
Sequence total quantity: 4
SEQ ID NO: 1            moltype = AA   length = 456
FEATURE                 Location/Qualifiers
source                  1..456
                        mol_type = protein
                        organism = Segmented Filamentous Bacteria
SEQUENCE: 1
MSIKSIFYSQ KEFFNEEATL PINFRMVNLI KLKKELLKNE NEIYTALYED LGKSKEDAFI    60
SEFSHCLNEI NYFIKNLRSL SKPKKVKTSF INFKSKAYIY KKPYGVCLII SCWNYPLYLS   120
LMPLIGAIAS GNTCILKLHP LSHNTNKLIE KILREIFEKC YIFSTYGDEN ELNELLDLNF   180
DYIFGTGNPN FGKLIYEKSS KNLIPITLEL GGKNPCIVHD DCKIDVSCKR IVHGKFLNSG   240
QTCLAPDIIY INHKIKDEFI RKIIFYIEHF YSEDPLNFKH YSKIINEPHF MRLIKILENH   300
RDNIIFGGES SKEKLKIAPT IIDKNEIIPC EIFGPILQIK TYDILDDIIY SLKCTPPPLA   360
LYLFTTNKTI INRFLNVPFG GGCINDTIVH VCENNLPFGG LKNSGIGAYH GRYSFDTFTH   420
KKSILIKSVK VDIKSRYPNS KNYNLKFIKP LFSKNK                             456

SEQ ID NO: 2            moltype = AA   length = 483
FEATURE                 Location/Qualifiers
source                  1..483
                        mol_type = protein
                        organism = B. bifidum
SEQUENCE: 2
MTTKETAAAT TTKQAAARQR AFAQLDATFR SGVTRPLRWR KAQLDAMARM LRQNATVIAR    60
AVRADLGKPA AETALMEIGL VLDEIRFIKP RLGRWAARHP KPMHYLLQPA VGWTVAEPKG   120
VALIISPWNY PVLLSFEPMA DAIAAGNCVC MKPSELSPHT SGVMADLIAR YMDPQAFRVV   180
QGGPQETTKL LEQPFNHIFY TGGGKVGSIV MAAAAKHLTP VTLELGGKSP VFVDRTANLD   240
VAARRIAWGR FINAGQTCVA PDYVLATSDV IEPLAGKIAK AITRFFGSDP QHSDSFGRII   300
NARHFDRLTA LLPDPKNPAN GRTVCGGNTR RDGLYIAPTV LLGVKPDAPV MQEEIFGPIL   360
PILEVADAKA AVEFINARPR PLAAYAFTGS KRVRRMFERE VSCGALGFNL PLGHLISSRL   420
PFGGVGASGM GSYHGKAGFL EFSHVKTVVG KPAVPDTLSL VYPPYDGLKK ILISAVSHTP   480
RVR                                                                 483

SEQ ID NO: 3            moltype = AA   length = 7
FEATURE                 Location/Qualifiers
source                  1..7
                        mol_type = protein
                        organism = Segmented Filamentous Bacteria
SEQUENCE: 3
TLELGGK                                                               7

SEQ ID NO: 4            moltype = AA   length = 7
FEATURE                 Location/Qualifiers
source                  1..7
                        mol_type = protein
                        organism = Segmented Filamentous Bacteria
SEQUENCE: 4
TLALGGK                                                               7
```

What is claimed is:

1. A method of enhancing an immune response in an individual in need thereof, comprising administering:
   [1] bacterial aldehyde dehydrogenase having at least 90% sequence identity to SEQ ID NO: 1 or SEQ ID NO: 2, a bacteria that produces said bacterial aldehyde dehydrogenase, or combinations thereof; and
   [2] one or both of vitamin A and retinol at a concentration of from about 0.5 to 10 micromolar, or from about 0.75 to about 7.7 micromolar, or from about 1 to about 5 micromolar,
   wherein said bacteria is selected from *Candidatus Arthromitus, Bacillus bifidum, Bacillus cereus, Enterococcus faecalis, Bacillus subtilis, Clostridium perfringes, Escherichia Coli K*-12, *Staphylococcus warni, Lactobacillus acidophilus, Tissierellia bacterium, Bacteroidales bacterium, Caloranaerobacter azorensis, Keratinibaculum paraultunense, Aneurinibacillus* sp., *Bacteroidetes bacterium, Tissierella* sp., *Thermohalobacter berrensis, Clostridium* sp., *Syntrophomonadaceae bacterium, Clostridiales bacterium, Bacteroidales bacterium, Tenericutes bacterium, Paenibacillus assamensis, Bacillus kexueae, Saliterribacillus persicus, Margalitia camelliae, Senegalia massiliensis, Aquisalibacillus elongatus, Sporanaerobacter, Syntrophomonadaceae bacterium, Aquibacillus sediminis, Paludibacteraceae bacterium, Cytobacillus oceanisediminis, Robertmurraya spiralis, Peribacillus saganii, Gottschalkia purinilytica, Anaerostipes faecalis, Lederbergia citrisecundus, Cytobacillus firmus, Paenibacillus alvei, Margalitia shackletonii, Sporotomaculum syntrophicum, Paenibacillus arenosi, Tenericutes bacterium zrk*29, *Neobacillus mesonae, Romboutsia* sp., *Flavobacteriaceae bacterium Ap*0902, *Romboutsia, Neobacillus mesonae, Cytobacillus, oceanisediminis, Lederbergia citrisecundus, Neobacillus* bataviensis, Halolactibacillus, alkaliphilus, Alkalihalobacillus wakoensis, Neobacillus massiliamazoniensis, Piscibacillus halophilus, Romboutsia, Bacillus dafuensis, Piscibacillus halophilus, Paenibacillus alvei, Gallicola sp., Saliterribacillus persicus, Arthrobacter citreus, Neobacillus vireti, Cytophagales bacterium, Anaerosalibacter massiliensis, Mollicutes bacterium, Neobacillus novalis, Methanosarcinaceae archaeon, and combinations thereof.

2. The method of claim 1, wherein said bacteria is selected from *Escherichia coli*, *Lactobacillus* (Lactic acid bacteria), and combinations thereof.

3. The method of claim 1, wherein said enhanced immune response is a decrease in susceptibility to a pathogenic infection compared to an individual without the administration, a decrease in pathogen activity following infection compared to an individual without the administration, a shortened period of infection by a pathogen compared to an individual without the administration, or combinations thereof.

4. The method of claim 3, wherein said pathogen is an intestinal pathogen selected from *Cirobacter*, *Escherichia*, and combinations thereof.

5. The method of claim 1, wherein said individual is an antibiotic-treated individual.

6. The method of claim 1, wherein said administration is enteral administration.

7. The method of claim 1, wherein said administration is oral administration.

8. The method of claim 1, wherein said bacteria is administered as a unit dose comprising from about $10^3$ colony forming units to about $10^8$ colony forming units.

9. The method of claim 1, wherein said bacteria is administered in a food product.

10. The method of claim 1, wherein said bacteria is formulated in a composition selected from a liquid, an emulsion, a solution, a suspension, a syrup, a slurry, a dispersion, a colloid, a dissolving tablet, a dissolving wafer, a capsule, a gel capsule, a semi-solid, a solid forma gel, a gel matrix a cream, or a paste.

11. A nutritional composition for enhancing an immune response comprising:
   [1] bacterial aldehyde dehydrogenase having at least 90% sequence identity to SEQ ID NO: 1 or SEQ ID NO: 2, a bacteria that produces said bacterial aldehyde dehydrogenase, or combinations thereof; and
   [2] one or both of vitamin A and retinol at a concentration of from about 0.5 to 10 micromolar, or from about 0.75 to about 7.7 micromolar, or from about 1 to about 5 micromolar,
   wherein said bacteria is selected from *Candidatus Arthromitus*, *Bacillus bifidum*, *Bacillus cereus*, *Enterococcus faecalis*, *Bacillus subtilis*, *Clostridium perfringes*, *Escherichia Coli K-12*, *Staphylococcus warni*, *Lactobacillus acidophilus*, *Tissierellia bacterium*, *Bacteroidales bacterium*, *Caloranaerobacter azorensis*, *Keratinibaculum paraultunense*, *Aneurinibacillus* sp., *Bacteroidetes bacterium*, *Tissierella* sp., *Thermohalobacter berrensis*, *Clostridium* sp., *Syntrophomonadaceae bacterium*, *Clostridiales bacterium*, *Bacteroidales bacterium*, *Tenericutes bacterium*, *Paenibacillus assamensis*, *Bacillus kexueae*, *Saliterribacillus persicus*, *Margalitia camelliae*, *Senegalia massiliensis*, *Aquisalibacillus elongatus*, *Sporanaerobacter*, *Syntrophomonadaceae bacterium*, *Aquibacillus sediminis*, *Paludibacteraceae bacterium*, *Cytobacillus oceanisediminis*, *Robertmurraya spiralis*, *Peribacillus saganii*, *Gottschalkia purinilytica*, *Anaerostipes faecalis*, *Lederbergia citrisecundus*, *Cytobacillus firmus*, *Paenibacillus alvei*, *Margalitia shackletonii*, *Sporotomaculum syntrophicum*, *Paenibacillus arenosi*, *Tenericutes bacterium zrk29*, *Neobacillus mesonae*, *Romboutsia* sp., *Flavobacteriaceae bacterium Ap0902*, *Romboutsia*, *Neobacillus mesonae*, *Cytobacillus*, *oceanisediminis*, *Lederbergia citrisecundus*, *Neobacillus bataviensis*, *Halolactibacillus*, *alkaliphilus*, *Alkalihalobacillus wakoensis*, *Neobacillus massiliamazoniensis*, *Piscibacillus halophilus*, *Romboutsia*, *Bacillus dafuensis*, *Piscibacillus halophilus*, *Paenibacillus alvei*, *Gallicola* sp., *Saliterribacillus persicus*, *Arthrobacter citreus*, *Neobacillus vireti*, *Cytophagales bacterium*, *Anaerosalibacter massiliensis*, *Mollicutes bacterium*, *Neobacillus novalis*, *Methanosarcinaceae archaeon*, and combinations thereof.

12. The nutritional composition of claim 11, wherein said bacteria is selected from *Escherichia coli*, *Lactobacillus* (Lactic acid bacteria), and combinations thereof.

13. The nutritional composition of claim 11, wherein said enhanced immune response is a decrease in susceptibility to a pathogenic infection compared to an individual without the administration, a decrease in pathogen activity following infection compared to an individual without the administration, a shortened period of infection by a pathogen compared to an individual without the administration, or combinations thereof.

14. The nutritional composition of claim 13, wherein said pathogenic infection is caused by an intestinal pathogen.

15. The nutritional composition of claim 14, wherein said pathogen is an intestinal pathogen selected from *Cirobacter*, *Escherichia*, and combinations thereof.

16. The nutritional composition of claim 11, wherein said composition is formulated for enteral administration.

17. The nutritional composition of claim 11, wherein said composition is formulated for oral administration.

18. The nutritional composition of claim 11, wherein said composition provides a unit dose of from about $10^3$ colony forming units to about $10^8$ colony forming units.

* * * * *